(12) United States Patent
Bethge et al.

(10) Patent No.: US 11,873,489 B2
(45) Date of Patent: Jan. 16, 2024

(54) NUCLEIC ACIDS FOR INHIBITING EXPRESSION OF A TARGET GENE COMPRISING PHOSPHORODITHIOATE LINKAGES

(71) Applicant: SILENCE THERAPEUTICS GMBH, Berlin (DE)

(72) Inventors: Lucas Bethge, Potsdam (DE); Judith Hauptmann, Berlin (DE); Christian Frauendorf, Berlin (DE); Adrien Weingärtner, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 588 days.

(21) Appl. No.: 16/763,399

(22) PCT Filed: Nov. 13, 2018

(86) PCT No.: PCT/EP2018/081101
§ 371 (c)(1),
(2) Date: May 12, 2020

(87) PCT Pub. No.: WO2019/092280
PCT Pub. Date: May 16, 2019

(65) Prior Publication Data
US 2020/0392495 A1    Dec. 17, 2020

(30) Foreign Application Priority Data

Nov. 13, 2017  (EP) .................................... 17201408
Jan. 16, 2018  (GB) .................................... 1800679
Apr. 5, 2018   (EP) .................................... 18165913

(51) Int. Cl.
*C07H 21/02*       (2006.01)
*C12N 15/113*      (2010.01)

(52) U.S. Cl.
CPC ...... *C12N 15/113* (2013.01); *C12N 2310/141* (2013.01); *C12N 2310/313* (2013.01); *C12N 2310/315* (2013.01); *C12N 2310/344* (2013.01); *C12N 2310/351* (2013.01); *C12N 2330/30* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 5,885,968 A | 3/1999 | Biessen et al. | |
| 7,452,987 B2 * | 11/2008 | Giese | ................ A61P 3/00 536/23.1 |
| 9,982,257 B2 * | 5/2018 | Butler | ............ C07H 21/00 |
| 2014/0316121 A1 * | 10/2014 | Prakash | ........ C12N 15/113 536/23.1 |

FOREIGN PATENT DOCUMENTS

| | | | |
|---|---|---|---|
| EP | 2853597 A1 | 4/2015 | |
| EP | 3228326 A1 | 10/2017 | |
| RU | 2430740 C2 | 10/2011 | |
| WO | WO-1999032619 A1 | 7/1999 | |
| WO | WO-2003/070910 A2 | 8/2003 | |
| WO | WO 2004/090105 A2 * | 10/2004 | .......... C12N 15/113 |
| WO | WO 2008/011431 A2 * | 1/2008 | .......... C12N 15/113 |
| WO | WO-2008/022309 A2 | 2/2008 | |
| WO | WO-2009/073809 A2 | 6/2009 | |
| WO | WO-2011/123621 A2 | 10/2011 | |
| WO | WO-2013176477 A1 | 11/2013 | |
| WO | 2017/174657 A1 | 10/2017 | |

OTHER PUBLICATIONS

Elbashir et al. (The EMBO Journal, vol. 20, No. 23, pp. 6877-6888, 2001).*
Parmar et al. (ChemBioChem, 2016, 17, 985-989).*
Akinc et al., Targeted delivery of RNAi therapeutics with endogenous and exogenous ligand-based mechanisms, Mol. Ther., 18(7):1357-64 (2010).
Biessen et al., Synthesis of cluster galactosides with high affinity for the hepatic asialoglycoprotein receptor, J. Med. Chem., 38(9):1538-46 (1995).
Dubber et al., Solid-phase synthesis of multivalent glycoconjugates on a DNA synthesizer, Bioconjug. Chem., 14(1):239-46 (2003).
Elbashir et al., Duplexes of 21-nucleotide RNAs mediate RNA interference in cultured mammalian cells, Nature, 411(6836):494-8 (2001).
Elbashir et al., RNA interference is mediated by 21- and 22-nucleotide RNAs, Genes & Development, 15(2):188-200 (2001).
Fire et al., Potent and specific genetic interference by double-stranded RNA in Caenorhabditis elegans, Nature, 391(6669):806-11 (1998).
International Application No. PCT/EP2018/081101, International Search Report and Written Opinion, dated Jan. 18, 2019.
International Application No. PCT/EP2018/081101, International Preliminary Report on Patentability, dated May 28, 2020.
Ishibashi et al., Asialoglycoprotein receptor deficiency in mice lacking the minor receptor subunit, J. Biol. Chem., 269(45):27803-6 (1994).
Nair et al., Multivalent N-Acetylgalactosamine-Conjugated siRNA Localizes in Hepatocytes and Elicits Robust RNAi-Mediated Gene Silencing, J. Am. Chem. Soc., 136(49):16958-16961 (2014).
Prakash et al., Solid-phase synthesis of 5'-triantennaryN-acetylgalactosamine conjugated antisense oligonucleotides using phosphoramidite chemistry, Bio. Med. Chem. Lett, 25(19):4127-4130 (2015).

(Continued)

*Primary Examiner* — Amy H Bowman
(74) *Attorney, Agent, or Firm* — MARSHALL, GERSTEIN & BORUN LLP

(57) ABSTRACT

The present invention relates to products and compositions and their uses. In particular the invention relates to nucleic acid products that interfere with target gene expression or inhibit target gene expression and therapeutic uses of such products.

14 Claims, 12 Drawing Sheets
Specification includes a Sequence Listing.

(56) References Cited

OTHER PUBLICATIONS

Takei et al., 5'-,3'-inverted thymidine-modified antisense oligodeoxynucleotide targeting midkine. Its design and application for cancer therapy, J. Biol. Chem., 277(26):23800-06 (2002).
Watts et al., Silencing disease genes in the laboratory and the clinic, Journal of Pathology, 226(2):365-379 (2012).
Weigel et al., Glycans as endocytosis signals: the cases of the asialoglycoprotein and hyaluronan/chondroitin sulfate receptors, Biochim. Biophys. Acta., 1572(2-3):341-63 (2002).
Czajkowski et al., "Encoding and storage of spatial information in the retrospenial cortex", Proceedings of the National Academy of Sciences, vol. 111, No. 23, pp. 8661-8666 (2014).

* cited by examiner

Figure 7

| duplex ID | sequence and chemistry<br>(top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>[ST23(ps)]3 ST41(ps) fUmCfAmCfCmUfGmCfUmUfCmUfUmCfUmGfG(ps)mU(ps)fU |
| STS12009V54L50 | mA(ps)fA(ps)mCfCmAfGmAfAmGfAmAfGmCfAmGfGmUfG(ps2)mA<br>[ST23]3 ST41 fU(ps2)mCfAmCfCmUfGmCfUmUfCmUfUmCfUmGfGmU(ps2)fU |
| STS12009V55L50 | mA(ps)fA(ps)mCfCmAfGmAfAmGfAmAfGmCfAmGfGmUfG(ps2)mA<br>[ST23]3 ST41 fUmCfAmCfCmUfGmCfUmUfCmUfUmCfUmGfGmU(ps2)fU |
| STS12009V56L50 | mAfAmCfCmAfGmAfAmGfAmAfGmCfAmGfGmUfGmA<br>[ST23]3 ST41 fUmCfAmCfCmUfGmCfUmUfCmUfUmCfUmGfGmU(ps2)fU |
| STS12009V57L50 | mAfAmCfCmAfGmAfAmGfAmAfGmCfAmGfGmUfG(ps2)mA<br>[ST23]3 ST41 fUmCfAmCfCmUfGmCfUmUfCmUfUmCfUmGfGmU(ps2)fU | mA, mU, mC, mG – 2'-OMe RNA
fA, fU, fC, fG – 2'-F RNA
(ps) – phosphorothioate
(ps2) – phosphorodithioate

Figure 8

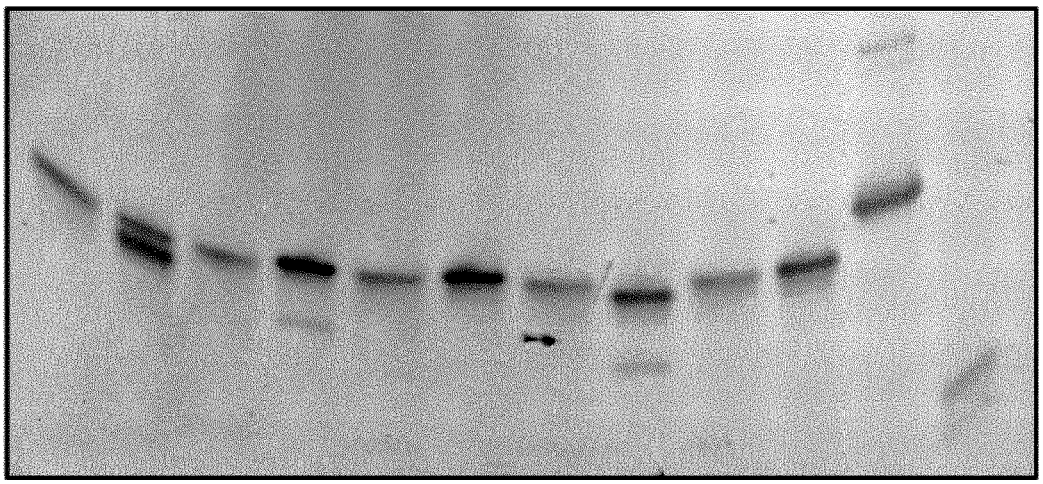

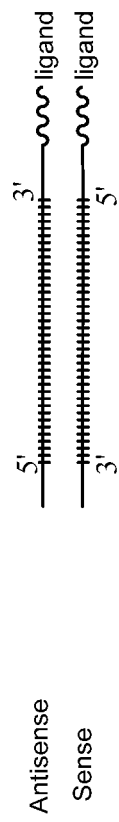
Figure 16A
Antisense
Sense
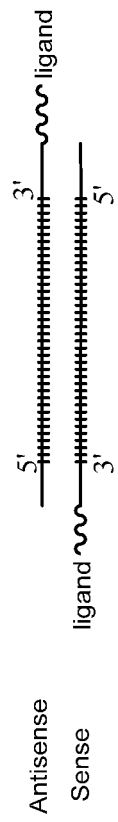
Figure 16B
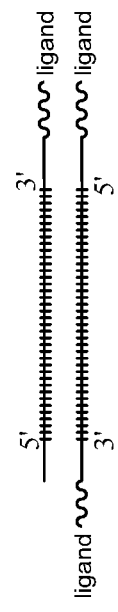
Figure 16C
Antisense
Sense
Figure 16D
Antisense
Sense
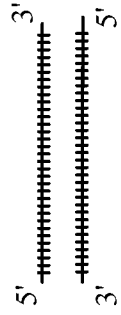
Figure 16E

NUCLEIC ACIDS FOR INHIBITING EXPRESSION OF A TARGET GENE COMPRISING PHOSPHORODITHIOATE LINKAGES

The present invention relates to products and compositions and their uses. In particular the invention relates to nucleic acid products that interfere with target gene expression or inhibit target gene expression and therapeutic uses of such products.

BACKGROUND

Double-stranded RNA (dsRNA) able to complementarily bind expressed mRNA has been shown to be able to block gene expression (Fire et al, 1998 and Elbashir et al, 2001) by a mechanism that has been termed RNA interference (RNAi). Short dsRNAs direct gene-specific, post-transcriptional silencing in many organisms, including vertebrates, and have become a useful tool for studying gene function. RNAi is mediated by the RNA-induced silencing complex (RISC), a sequence-specific, multi-component nuclease that destroys messenger RNAs homologous to the silencing trigger loaded into the RISC complex. Interfering RNA (iRNA) such as siRNAs, antisense RNA, and micro-RNA are oligonucleotides that prevent the formation of proteins by gene-silencing i.e. inhibiting gene translation of the protein through degradation of mRNA molecules. Gene-silencing agents are becoming increasingly important for therapeutic applications in medicine.

According to Watts and Corey in the Journal of Pathology (2012; Vol 226, p 365-379) there are algorithms that can be used to design nucleic acids but none is perfect. It may take various experimental methods to identify potent siRNAs, as algorithms do not take into account factors such as tertiary structure or the involvement of RNA binding proteins. Therefore the discovery of a potent nucleic acid with minimal off-target effects is a complex process. For the pharmaceutical development of these highly charged molecules it is necessary that they can be synthesised economically, distributed to target tissues, enter cells and function within acceptable limits of toxicity.

However, delivery of nucleic acids, such as RNA, to cells avoiding degradation by cellular nucleases, whilst maintaining efficacy and target specificity has proved challenging to those in the field of developing nucleic acid molecules for therapeutic use.

Thus, means for efficient delivery of oligonucleotides, in particular double stranded siRNAs, to cells in vivo is becoming increasingly important and requires specific targeting and substantial protection from the extracellular environment, particularly serum proteins. One method of achieving specific targeting is to conjugate a targeting moiety to the iRNA duplex agent. The targeting moiety helps in targeting the iRNA duplex agent to the required target site and there is a need to design appropriate targeting moieties for the desired receptor sites for the conjugated molecules to be taken up by the cells such as by endocytosis.

However, targeting ligands developed so far do not always translate to in vivo settings and there is a clear need for more efficacious receptor specific ligand conjugated iRNA duplex agents and methods for their preparation for the in vivo delivery of oligonucleotide therapeutics, nucleic acids and double stranded siRNAs.

Rather than a lipid delivery system alone, the present invention addresses the structure of the nucleic acid itself. It has been unexpectedly found that a nucleic acid in accordance with the present invention has increased stability, which prevents degradation of the nucleic acid before entry into a cell.

SUMMARY OF INVENTION

The present invention provides a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first and/or second strand includes a phosphorodithioate linkage between at least two nucleotides. The first strand may not comprise a phosphorodithioate linkage between any of the two, three or four terminal nucleotides at the 5' end.

The first and/or second strand may include a phosphorodithioate linkage between the at least two terminal 3' nucleotides and/or the second strand may include a phosphorodithioate linkage between the at least two terminal 5' nucleotides.

The nucleic acid may comprise a phosphorodithioate linkage between each of the two, three or four terminal nucleotides at the 3' end of the first strand. The nucleic acid may comprise a phosphorodithioate linkage between each of the two, three or four terminal nucleotides at the 3' end of the second strand. The nucleic acid may comprise a phosphorothioate or a phosphorodithioate linkage between each of the two, three or four terminal nucleotides at the 5' end of the second strand.

The nucleic acid of the invention may also comprise a phosphorothioate linkage between each of the three terminal 3' nucleotides and/or between each of the three terminal 5' nucleotides on the first strand, and/or between each of the three terminal 3' nucleotides and/or between each of the three 5' nucleotides of the second strand when there is no phosphorodithioate linkage present at that end.

The first strand and second strand of the nucleic acid may be separate strands. The nucleic acid may comprise a single strand that comprises the first strand and the second strand.

The first strand and/or said second strand may be each from 17-35 nucleotides in length and the at least one duplex region may consist of 17-25 nucleotide base pairs.

The nucleic acid may: a) be blunt ended at both ends; b) have an overhang at one end and a blunt end at the other; or c) have an overhang at both ends.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more odd numbered nucleotides. At least one of the one or more modified even numbered nucleotides may be adjacent to at least one of the one or more modified odd numbered nucleotides.

A plurality of odd numbered nucleotides may be modified in the nucleic acid of the invention. A plurality of even numbered nucleotides may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification on the odd nucleotides of the first strand and/or one or more of the even numbered nucleotides of the second strand may be modified by the same modification on the odd nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first strand odd numbered nucleotides. A plurality of odd numbered nucleotides may be modified by a second modification, wherein the second modification is different to the modification on the first strand odd numbered nucleotides.

The second strand may comprise adjacent nucleotides that are modified by a common modification, which may be a second modification that is different from the modification on the odd numbered nucleotides of the first strand.

In the nucleic acid of the invention, each of the odd numbered nucleotides in the first strand and each of the even numbered nucleotides in the second strand may be modified with a common modification, and each of the even numbered nucleotides may be modified in the first strand with a second modification and each of the odd numbered nucleotides may be modified in the second strand with a second modification.

The nucleic acid of the invention may have the modified nucleotides of the first strand shifted by at least one nucleotide relative to the unmodified or differently modified nucleotides of the second strand.

The first strand may comprise a sequence of SEQ ID NO: 1 and/or the second strand may comprise a sequence of SEQ ID NO: 2.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide. At least one modification may be 2'-O-methyl and/or at least one modification may be 2'-F.

The nucleic acid of the invention may be conjugated with a ligand.

A nucleic acid of the invention may comprise a phosphorothioate linkage between the terminal one, two or three 3' nucleotides and/or 5' nucleotides of the first and/or the second strand, in addition to a phosphorodithioate linkage at the same or at a different end or strand.

The present invention provides as a second aspect, a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first and/or second strand includes a phosphorodithioate linkage between the at least two terminal 3' nucleotides and/or the second strand includes a phosphorodithioate linkage between the at least two terminal 5' nucleotides, and wherein the nucleic acid molecule is conjugated to a ligand.

A ligand for use in the present invention may therefore comprise (i) one or more N-acetyl galactosamine (GalNAc) moieties and derivatives thereof, and (ii) a linker, wherein the linker conjugates the GalNAc moieties to a sequence as defined in any preceding aspects. The linker may be a bivalent or trivalent or tetravalent branched structure. The nucleotides may be modified as defined herein.

The ligand may comprise the formula I:

$$[S—X^1—P—X^2]_3\text{-}A\text{-}X^3— \quad (I)$$

wherein:
S represents a saccharide, wherein the saccharide is N-acetyl galactosamine;
$X^1$ represents $C_3$-$C_6$ alkylene or $(—CH_2—CH_2—O)_m(—CH_2)_2—$ wherein m is 1, 2, or 3;
P is a phosphate or modified phosphate (preferably a thiophosphate);
$X^2$ is alkylene or an alkylene ether of the formula $(—CH_2)_n—O—CH_2—$ where n=1-6;
A is a branching unit;
$X^3$ represents a bridging unit;
wherein a nucleic acid according to the present invention is conjugated to $X^3$ via a phosphate or modified phosphate (preferably a thiophosphate).

The present invention therefore additionally provides a conjugated nucleic acid having one of the following structures:

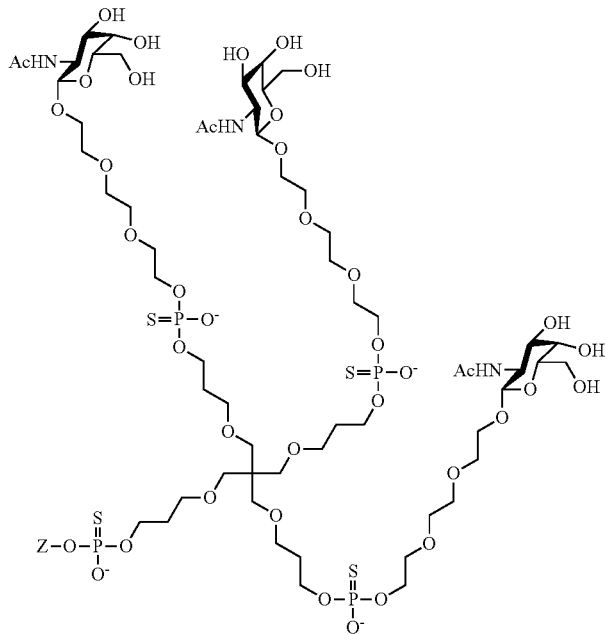

-continued
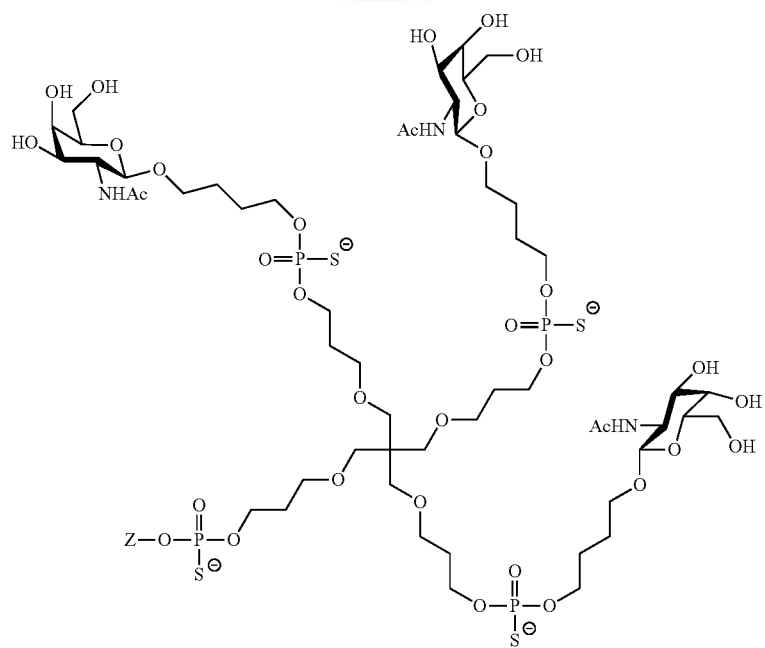
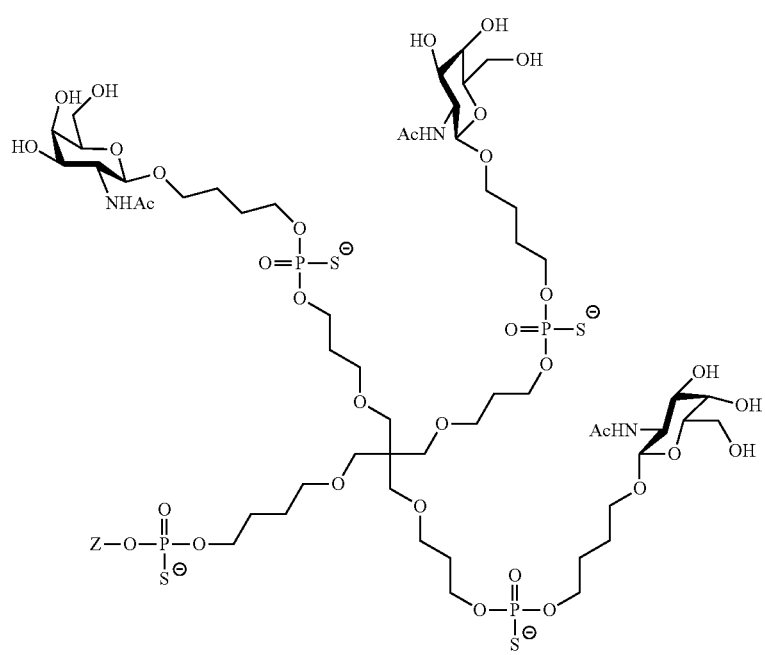

-continued
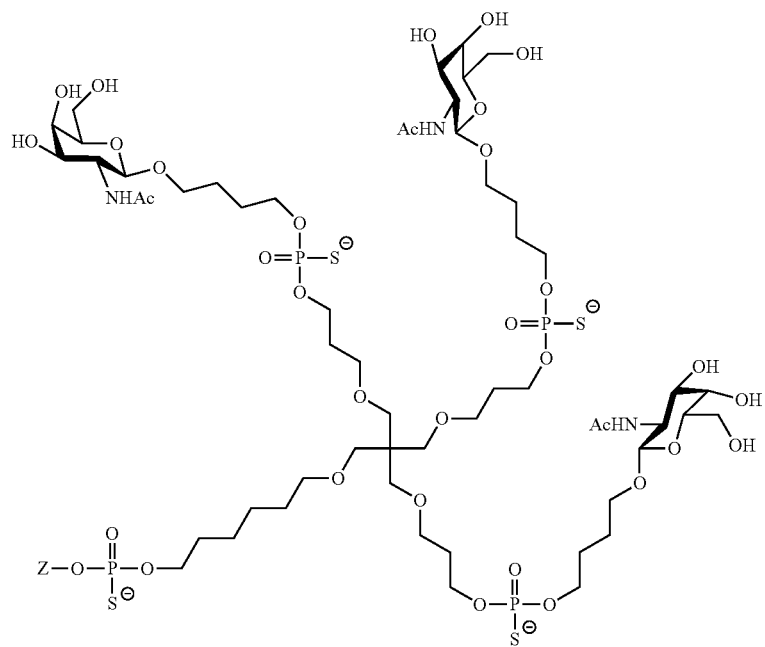
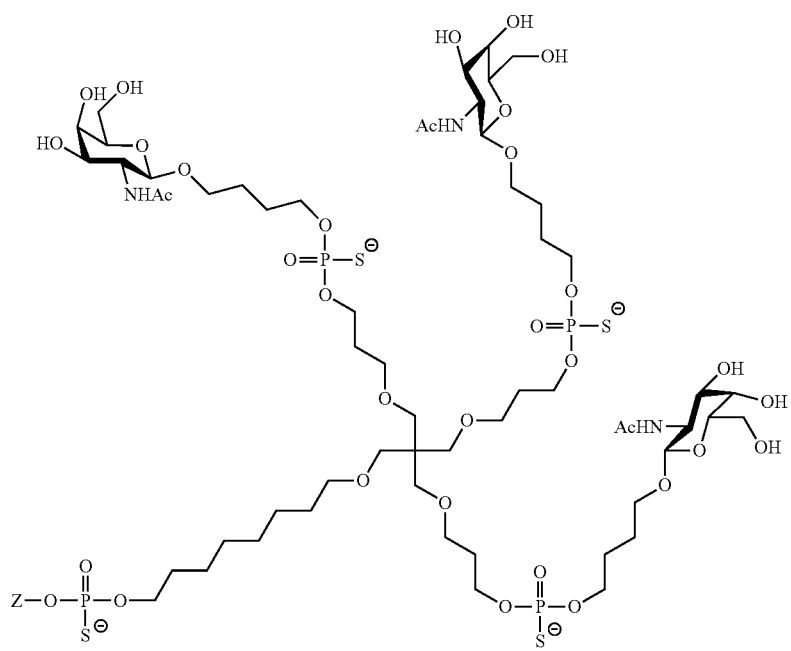

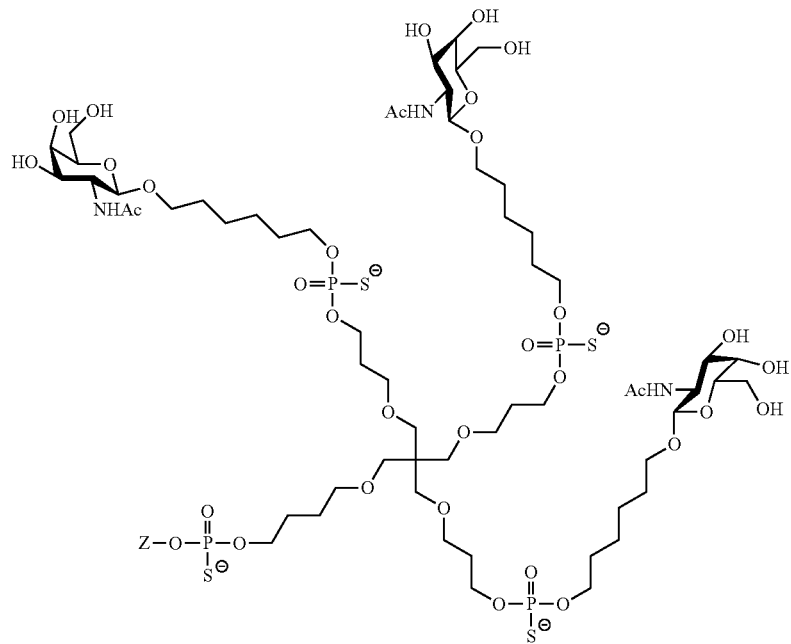
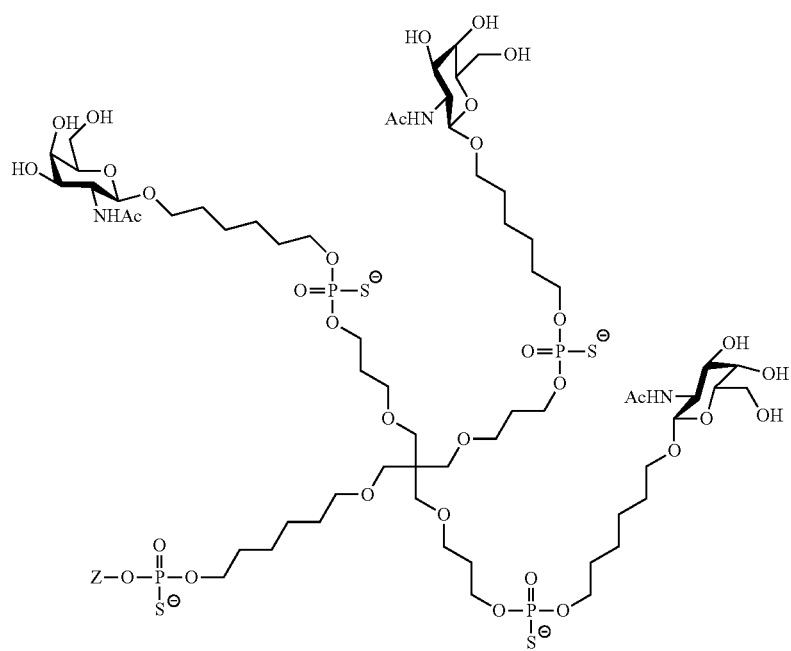

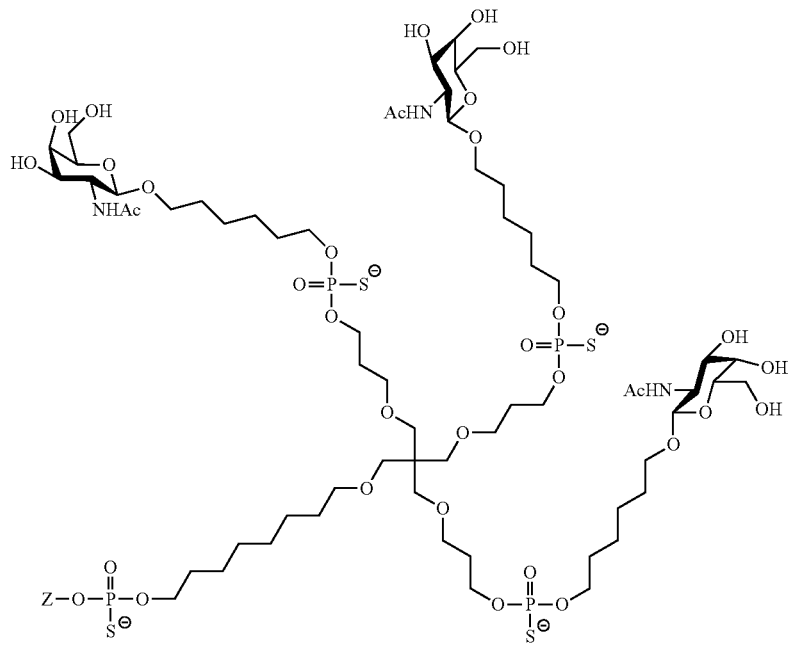

wherein Z represents a nucleic acid as defined herein before.

The ligand may comprise:

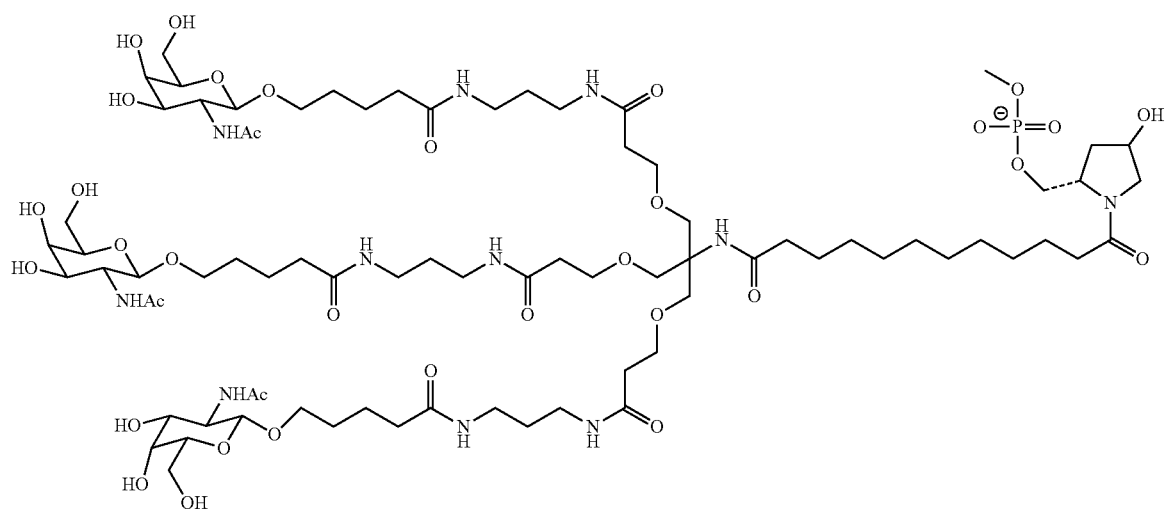

The invention also provides a composition comprising a nucleic acid or conjugated nucleic acid as defined herein and one or more physiologically acceptable excipients. The excipient(s) can be:

i) a cationic lipid, or a pharmaceutically acceptable salt thereof;
ii) a steroid;
iii) a phosphatidylethanolamine phospholipid;
iv) a PEGylated lipid.

The content of the cationic lipid component in the composition may be from about 55 mol % to about 65 mol % of the overall lipid content of the lipid formulation, preferably about 59 mol % of the overall lipid content of the lipid composition.

The composition may comprise;
a cationic lipid having the structure;
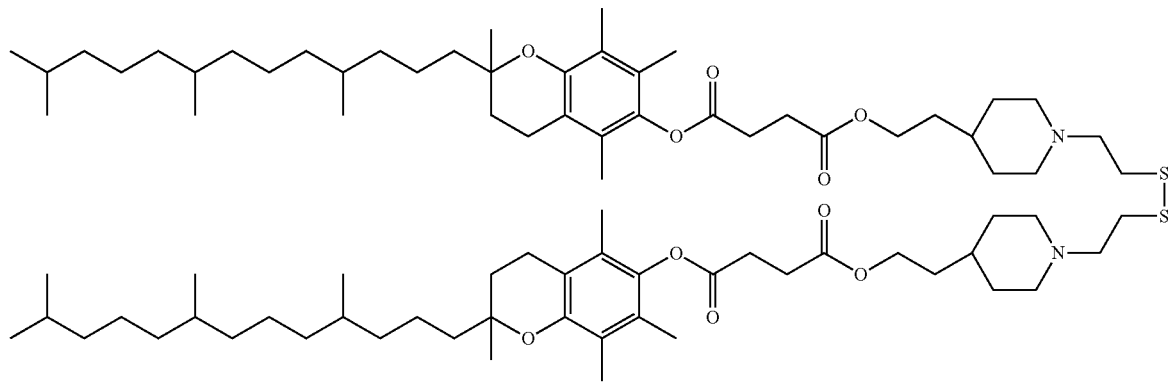 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]
a steroid having the structure;
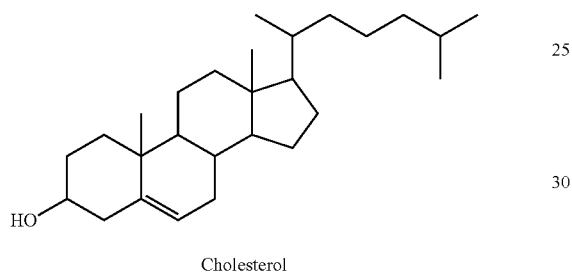
Cholesterol
a phosphatidylethanolamine phospholipid having the structure;
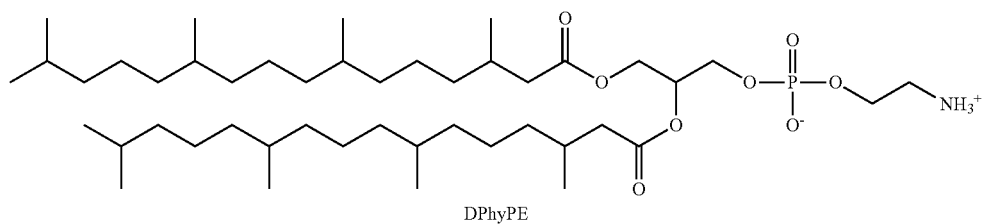 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]
DPhyPE
and a PEGylated lipid having the structure;
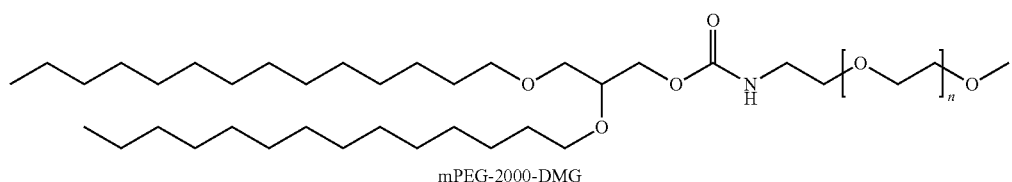
mPEG-2000-DMG Also provided is a nucleic acid or conjugated nucleic acid according to any aspect of the invention for use in the treatment or prevention of a disease or disorder and/or in the manufacture of a medicament for treating or preventing a disease or disorder.

The invention provides a method of treating or preventing a disease or disorder comprising administration of a composition comprising a nucleic acid or conjugated nucleic acid according to any aspect of the invention to an individual in need of treatment. The nucleic acid or conjugated nucleic acid may be administered to the subject subcutaneously, intravenously or using any other application routes such as oral, rectal or intraperitoneal. A method of making the nucleic acid or conjugated nucleic acid according to the invention is also included.

DETAILED DESCRIPTION OF INVENTION

The present invention relates to a nucleic acid which is double stranded and directed to an expressed RNA transcript of a target gene and compositions thereof. These nucleic acids can be used in the treatment of a variety of diseases and disorders where reduced expression of target gene products is desirable.

A first aspect of the invention relates to a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene to be inhibited and wherein the said first and/or second strand includes a phosphorodithioate linkage between at least two nucleotides.

Optionally, the first and/or second strand may include a phosphorodithioate linkage between the at least two terminal 3' nucleotides and/or the second strand may include a phosphorodithioate linkage between the at least two terminal 5' nucleotides.

Optionally, the first strand does not comprise a phosphorodithioate linkage between any of the two, three or four terminal nucleotides at the 5' end, in other words, it comprises a linkage other than a phosphorodithioate linkage between any of the two, three or four terminal nucleotides at the 5' end.

A related aspect is a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein the nucleic acid comprises a phosphorodithioate linkages between the two terminal nucleotides at the 3' end of the first strand, wherein the nucleic acid comprises a phosphorodithioate linkage each between the two terminal nucleotides at the 3' end and between the two terminal nucleotides at the 5' end of the second strand, and wherein the first strand comprise a linkage other than a phosphorodithioate between the two, three or four terminal nucleotides at the 5' end.

Preferably this linkage other than a phosphorodithioate is a phosphate or a phosphorothioate, more preferably a (unsubstituted) phosphate. Preferably, all the linkages between the nucleotides of both strands other than the linkage between the two terminal nucleotides at the 3' end of the first strand and the linkages between the two terminal nucleotides at the 3' end and at the 5' end of the second strand are unsubstituted phosphate linkages.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self complementary which 'folds' to form a double stranded molecule. The nucleic acid may be an siRNA molecule.

The nucleic acid may comprise ribonucleotides, modified ribonucleotides, deoxynucleotides, deoxyribonucleotides, or nucleotide analogues. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for the formation of a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and are at least partially complementary to each other.

Depending on the length of a nucleic acid, a perfect match in terms of base complementarity between the first strand and second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be at least 70%, 75%, 80%, 85%, 90% or 95%.

The first strand and the second strand may each comprise a region of complementarity which comprises at least 15 contiguous nucleotides.

The nucleic acid involves the formation of a duplex region between all or a portion of the first strand and a portion of the target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence however, the first strand must be able to form a duplex structure with both the second strand and the target sequence.

The complementarity between the first strand and the target sequence may be perfect (no nucleotide mismatches or additional/deleted nucleotides in either nucleic acid).

The complementarity between the first strand and the target sequence may not be perfect. The complementarity may be from about 70% to about 100%. More specifically, the complementarity may be at least 70%, 80%, 85%, 90% or 95%, or an intermediate value.

The identity between the first strand and the complementary sequence of the target sequence may be from about 75% to about 100%. More specifically, the complementarity may be at least 75%, 80%, 85%, 90% or 95%, or an intermediate value, provided a nucleic acid is capable of reducing or inhibiting the expression of a target gene.

A nucleic acid with less than 100% complementarity between the first strand and the target sequence may be able to reduce the expression of a target gene to the same level as a nucleic acid with perfect complementarity between the first strand and the target sequence. Alternatively, it may be able to reduce expression of a target gene to a level that is 20%, 30%, 40%, 50%, 60%, 70%, 80%, 90% or 100% of the level of expression achieved by the nucleic acid with perfect complementarity.

In a further aspect the nucleic acid as described herein may reduce the expression of a target gene in a cell by at least 10% compared to the level observed in the absence of an inhibitor, which may be the nucleic acid. All preferred features of any of the previous aspects also apply to this aspect. In particular, the expression of a target gene in a cell may be reduced to 90%, 80%, 70%, 60%, 50%, 40%, 30%, 20%, 15% or less, and intermediate values, than that observed in the absence of an inhibitor (which may be the nucleic acid).

The nucleic acid may comprise a first strand and a second strand that are each from 19-25 nucleotides in length. The first strand and the second strand may be of different lengths.

The nucleic acid may be 15-25 nucleotide pairs in length. The nucleic acid may be 17-23 nucleotide pairs in length. The nucleic acid may be 17-25 nucleotide pairs in length. The nucleic acid may be 23-24 nucleotide pairs in length. The nucleic acid may be 19-21 nucleotide pairs in length. The nucleic acid may be 21-23 nucleotide pairs in length. The nucleic acid may comprise a duplex region that consists of 19-25 nucleotide base pairs. The duplex region may consist of 17, 18, 19, 20, 21, 22, 23, 24 or 25 base pairs which may be contiguous.

Preferably, the nucleic acid mediates RNA interference.

In a further aspect the nucleic acid or conjugated nucleic acid as described may reduce the expression of its target transcript by at least 15% compared to the expression observed in the absence of the nucleic acid or conjugated nucleic acid. All preferred features of any of the previous aspects also apply to this aspect. In particular, the expression of the target transcript may be reduced to at least the following given % or less than 90%, 80%, 70%, 60%, 50%, 40%, 30%, 20%, 15% or less, and intermediate values, than that observed in the absence of the nucleic acid or conjugated nucleic acid or in the presence of a non-silencing control.

The use of a phosphorodithioate linkage in the nucleic acid of the invention reduces the variation in the stereochemistry of a population of nucleic acid molecules, which can be caused by a phosphorothioate linkage having a chiral centre and being unable to control which non-linking oxygen is substituted for sulphur. The use of phosphorodithioate ensures that no chiral centre exists in that linkage and thus reduces or eliminates any variation in the population of nucleic acid molecules, depending on the number of phosphorodithioate and phosphorothioate linkages used in the nucleic acid molecule.

Furthermore, without being bound by theory, it may be that a single phosphorodithioate linkage can be used in place of two phosphorothioate linkages, and thus reducing the number of "non-natural" linkages within the nucleic acid of the invention.

The nucleic acid may comprise a phosphorodithioate linkage between each of the two, three or four terminal nucleotides at the 3' end of the first strand. The nucleic acid may comprise a phosphorodithioate linkage between each of the two, three or four terminal nucleotides at the 3' end of the second strand. The nucleic acid may comprise a phosphorothioate or a phosphorodithioate linkage between each of the two, three or four terminal nucleotides at the 5' end of the second strand.

The nucleic acid of the invention may also comprise a phosphorothioate linkage between each of the three terminal 3' nucleotides and/or between each of the three terminal 5' nucleotides on the first strand, and/or between each of the three 3' terminal nucleotides and/or between each of the three 5' terminal nucleotides of the second strand when there is no phosphorodithioate linkage present at that end.

The nucleic acid of the invention may comprise a mixture of phosphorothioate and phosphorodithioate linkages, examples of which are set out herein. The nucleic acid of the invention may comprise a phosphorodithioate at the 3' end of each of the first strand and the second strand.

The nucleic acid may be blunt ended at both ends; have an overhang at one end and a blunt end at the other end; or have an overhang at both ends.

An "overhang" as used herein has its normal and customary meaning in the art, i.e. a single stranded portion of a nucleic acid that extends beyond the terminal nucleotide of a complementary strand in a double strand nucleic acid. The term "blunt end" includes double stranded nucleic acids whereby both strands terminate at the same position, regardless of whether the terminal nucleotide(s) are base paired. The terminal nucleotide of a first strand and a second strand at a blunt end may be base paired. The terminal nucleotide of a first strand and a second strand at a blunt end may not be paired. The terminal two nucleotides of an first strand and a second strand at a blunt end may be base paired. The terminal two nucleotides of an first strand and a second strand at a blunt end may not be paired.

An "unsubstituted phosphate" as used herein designates a normal phosphate as is usually found between two nucleotides in nature, for example in natural DNA or RNA molecules. Such a phosphate can be designated herein simply as "phosphate", "unsubstituted phosphate" or "phosphodiester".

The nucleic acid may have an overhang at one end and a blunt end at the other. The nucleic acid may have an overhang at both ends. The nucleic acid may be blunt ended at both ends. The nucleic acid may be blunt ended at the end with the 5'-end of the first strand and the 3'-end of the second strand or at the 3'-end of the first strand and the 5'-end of the second strand.

The nucleic acid may comprise an overhang at a 3'- or 5'-end. The nucleic acid may have a 3'-overhang on the first strand. The nucleic acid may have a 3'-overhang on the second strand. The nucleic acid may have a 5'-overhang on the first strand. The nucleic acid may have a 5'-overhang on the second strand. The nucleic acid may have an overhang at both the 5'-end and 3'-end of the first strand. The nucleic acid may have an overhang at both the 5'-end and 3'-end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3'-end or 5' end of the second strand or the first strand may be selected from 1, 2, 3, 4 and 5 nucleotides in length. Optionally, an overhang may consist of 1 or 2 nucleotides, which may or may not be modified.

Unmodified polynucleotides, particularly ribonucleotides, may be prone to degradation by cellular nucleases, and, as such, modifications/modified nucleotides may be included in the nucleic acid of the invention. Such modifications may help to stabilise the nucleic acid by making them more resistant against nucleases. This improved resistance allows nucleic acids to be active in mediating RNA interference for longer time periods and is especially desirable when the nucleic acids are to be used for treatment.

One or more nucleotides on the second and/or first strand of the nucleic acid of the invention may be modified.

Modifications of the nucleic acid of the present invention generally provide a powerful tool in overcoming potential limitations including, but not limited to, in vitro and in vivo stability and bioavailability inherent to native RNA molecules. The nucleic acid according to the invention may be modified by chemical modifications. Modified nucleic acid can also minimise the possibility of inducing interferon activity in humans. Modification can further enhance the functional delivery of a nucleic acid to a target cell. The modified nucleic acid of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleic acids or bases.

One or more nucleotides of a nucleic acid of the present invention may be modified. The nucleic acid may comprise at least one modified nucleotide. The modified nucleotide may be on the first strand. The modified nucleotide may be in the second strand. The modified nucleotide may be in the duplex region. The modified nucleotide may be outside the duplex region, i.e., in a single stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5-terminal nucleotide of the second strand may be a modified nucleotide.

An nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides. The nucleic acid may retain 55%, 60%, 65%, 70%, 75%, 80%, 85%, 90%, 95% or 100% or an intermediate value of its activity as compared to the same nucleic acid but without said modified nucleotides, or may have more than 100% of the activity of the same nucleotide without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3'-terminal deoxy-thymine (dT) nucleotide, a 2'-O-methyl modified nucleotide, a 2' modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified nucleotide, wherein the base is selected from 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine. The base may be 2,6-diaminopurine riboside, pyridin-4-one riboside, pyridin-2-one riboside, phenyl riboside, 2,4,6-trimethoxy benzene riboside, aminophenyl riboside, 6-azapyrimidine riboside, propyne riboside.

Nucleic acids discussed herein include unmodified RNA as well as RNA which has been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. Modified nucleotide as used herein refers to a nucleotide in which one or more of the components of the nucleotides, namely sugars, bases, and phosphate moieties, are different from that which occur in nature. While they are referred to as modified nucleotides they will of course, because of the modification, include molecules which are not nucleotides, for example a polynucleotide molecules in which the ribophosphate backbone is replaced with a non-ribophosphate construct that allows hybridisation between strands i.e. the modified nucleotides mimic the ribophosphate backbone.

Many of the modifications described below that occur within a nucleic acid will be repeated within a polynucleotide molecule, such as a modification of a base, or a phosphate moiety, or a non-linking O of a phosphate moiety. In some cases the modification will occur at all of the possible positions/nucleotides in the polynucleotide but in many cases it will not. A modification may only occur at a 3' or 5' terminal position, may only occur in a terminal regions, such as at a position on a terminal nucleotide or in the last 2, 3, 4, 5, or 10 nucleotides of a strand. A modification may occur in a double strand region, a single strand region, or in both. A modification may occur only in the double strand region of a nucleic acid of the invention or may only occur in a single strand region of an nucleic acid of the invention. A phosphorothioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single strand regions, particularly at termini. The 5' end or 3' ends may be phosphorylated.

Stability of an nucleic acid of the invention may be increased by including particular bases in overhangs, or by including modified nucleotides, in single strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphorothioate modifications. Overhangs need not be homologous with the target sequence.

The 5'- or 3'-overhangs at the sense strand, antisense strand or both strands of the dsRNA agent of the invention may be phosphorylated. In some embodiments, the overhang region contains two nucleotides having a phosphorothioate between the two nucleotides, where the two nucleotides can be the same or different. In one embodiment, the overhang is present at the 3'-end of the sense strand, antisense strand or both strands. In one embodiment, this 3'-overhang is present in the antisense strand. In one embodiment, this 3'-overhang is present in the sense strand.

Nucleases can hydrolyse nucleic acid phosphodiester bonds. However, chemical modifications to nucleic acids can confer improved properties, and, can render oligoribonucleotides more stable to nucleases.

Modified nucleic acids, as used herein, can include one or more of:
(i) alteration, e.g., replacement, of one or both of the non-linking phosphate oxygens and/or of one or more of the linking phosphate oxygens (referred to as linking even if at the 5' and 3' terminus of the nucleic acid of the invention);
(ii) alteration, e.g., replacement, of a constituent of the ribose sugar, e.g., of the 2' hydroxyl on the ribose sugar;
(iii) replacement of the phosphate moiety with "dephospho" linkers;
(iv) modification or replacement of a naturally occurring base;
(v) replacement or modification of the ribose-phosphate backbone;
(vi) modification of the 3' end or 5' end of the RNA, e.g., removal, modification or replacement of a terminal phosphate group or conjugation of a moiety, e.g., a fluorescently labelled moiety, to either the 3' or 5' end of RNA.

The terms replacement, modification, alteration, indicates a difference from a naturally occurring molecule.

Specific modifications are discussed in more detail below.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

A modified nucleotide can include modification of the sugar groups. The 2' hydroxyl group (OH) can be modified or replaced with a number of different "oxy" or "deoxy" substituents.

Examples of "oxy"-2'hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=NH2; alkylamino, dialkylamino, heterocyclyl, arylamino, diaryl amino, heteroaryl amino, or diheteroaryl amino, ethylene diamine, polyamino) and aminoalkoxy, O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino).

"Deoxy" modifications include hydrogen halo; amino (e.g., NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substituents of certain embodiments include 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified nucleotides may contain a sugar such as arabinose.

Modified nucleotides can also include "abasic" sugars, which lack a nucleobase at C-1'.

These abasic sugars can further contain modifications at one or more of the constituent sugar atoms.

The 2' modifications may be used in combination with one or more phosphate linker modifications (e.g., phosphorothioate).

The phosphate groups can individually be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethyliminogroups.

The phosphate linker and ribose sugar may be replaced by nuclease resistant nucleotides.

Examples include the morpholino, cyclobutyl, pyrrolidine and peptide nucleic acid (PNA) nucleoside surrogates. In certain embodiments, PNA surrogates may be used.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labelling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5'O, N, S or C group of the sugar. Alternatively, the linker can connect to or replace the terminal atom of a nucleotide surrogate (e.g., PNAs). These spacers or linkers can include e.g., —($CH_2$)$_n$—, —($CH_2$)$_n$N—, —($CH_2$)$_n$O—, —($CH_2$)$_n$S—, —O($CH_2CH_2$)$CH_2CH_2$O— (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases, EDTA, lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5'terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH$_2$—), 5'vinylphosphonate, 5'-alkyletherphosphonates (R=alkylether=methoxymethyl (MeOCH$_2$—), ethoxymethyl, etc., e.g., RP(OH)(O)—O-5'-).

The nucleic acid of the present invention may include one or more phosphorothioate modifications on one or more of the terminal ends of the first and/or the second strand. Optionally, each or either end of the first strand may comprise one or two or three phosphorothioate modified nucleotides. Optionally, each or either end of the second strand may comprise one or two or three phosphorothioate modified nucleotides. Optionally, both ends of the first strand and the 5' end of the second strand may comprise two phosphorothioate modified nucleotides. By phosphorothioate modified nucleotide it is meant that the linkage between the nucleotide and the adjacent nucleotide comprises a phosphorothioate group instead of a standard phosphate group.

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Adenine, guanine, cytosine and uracil are the most common bases found in RNA. These bases can be modified or replaced to provide RNAs having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogues of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyluracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand and includes abasic ribose moiety, abasic deoxyribose moiety, modifications abasic ribose and abasic deoxyribose moieties including 2'O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogues including 4',5'-methylene nucleotide; 1-(3-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non-bridging methylphosphonate and 5'-mercapto moieties.

The nucleic acids of the invention may be included as one or more inverted nucleotides, for example inverted thymidine or inverted adenine (for example see Takei, et al., 2002. JBC 277 (26):23800-06).

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits or peptides, is reduced below that observed in the absence of a nucleic acid of the invention or in reference to an siRNA molecule with no known homology to human transcripts (herein termed non-silencing control). Such control may be conjugated and modified in an analogous manner to the molecule of the invention and delivered into the target cell by the same route; for example the expression may be reduced to 90%, 80%, 70%, 60%, 50%, 40%, 30%, 20%, 15% or less than that observed in the absence of an inhibitor (which may be the nucleic acid) or in the presence of a non-silencing control (which may be a nucleic acid that is non-complementary to the target sequence).

The nucleic acid of the present invention may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid of the invention may be modified wherein the first strand is numbered 5' to 3', the 5'-most nucleotide being nucleotide number 1 of the first strand. The term "odd numbered" as described herein means a number not divisible by two. Examples of odd numbers are 1, 3, 5, 7, 9, 11 and so on. One or more of the even numbered nucleotides of the first strand of the nucleic acid of the invention may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid of the invention may be modified wherein the second strand is numbered 3' to 5', the 3'-most nucleotide being nucleotide number 1 of the second strand. One or more of the even numbered nucleotides of the second strand of the nucleic acid of the invention may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid of the invention may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

The nucleic acid of the invention may comprise single or double stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd numbered nucleotides of the first strand. One or more nucleotides of second strand may also be modified with the second modification. One or more nucleotides with the second modification may be adjacent to each other and to nucleotides having a modification that is the same as the modification of the odd numbered nucleotides of the first strand. The first strand may also comprise phosphorothioate linkages between the two nucleotides at the 3' end and at the 5' end. The second strand may comprise a phosphorothioate linkage between the two nucleotides at 5' end. The second strand may also be conjugated to a ligand at the 5' end.

The nucleic acid of the invention may comprise a first strand comprising adjacent nucleotides that are modified with a common modification. One or more of such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of second strand may also be modified with the second modification. One or more nucleotides with the second modification may be adjacent. The first strand may also comprise phosphorothioate linkages between the two nucleotides at the 5' end and at the 3' end. The second strand may comprise a phosphorothioate linkage between the two nucleotides at the 3' end. The second strand may also be conjugated to a ligand at the 5' end.

The nucleotides numbered (from 5' to 3' on the first strand and 3' to 5' on the second strand) 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present invention from 5' to 3' on the first strand and 3' to 5' on the second strand The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F. Further modifications as described herein may be present on the first and/or second strand.

The nucleic acid of the invention may comprise an inverted RNA nucleotide at one or several of the strand ends. Such inverted nucleotides provide stability to the nucleic acid. Preferably, the nucleic acid comprises at least an inverted nucleotide at one or several of the 3' end of at least one of the strands and/or at the 5' end of the of the second strand. More preferably, the nucleic acid comprises an inverted nucleotide at the 3' end of the second strand. Most preferably, the nucleic acid comprises an inverted RNA nucleotide at the 3' end of the second strand and this nucleotide is preferably an inverted A. The inverted nucleotide is preferably present at an end of a strand not as an overhang but opposite a corresponding nucleotide in the other strand. A nucleic acid with such a modification is stable and easy to synthesise.

Throughout the description of the invention, "same or common modification" means the same modification to any nucleotide, be that A, G, C or U modified with a group such as such as a methyl group or a fluoro group. Is it not taken to mean the same addition on the same nucleotide. For example, 2'F-dU, 2'F-dA, 2'F-dC, 2'F-dG are all considered to be the same or common modification, as are 2'-OMe-rU, 2'-OMe-rA; 2'-OMe-rC; 2'-OMe-rG. A 2'F modification is a different modification to a 2'OMe modification.

Some representative modified nucleic acid sequences of the present invention are shown in the examples. These examples are meant to be representative and not limiting.

Preferably, the nucleic acid may comprise a modification and the second or further modification which are each and individually selected from the group comprising 2'-O-methyl modification and 2'-F modification. The nucleic acid may comprise a modification that is 2'-O-methyl (2'OMe) that may be a first modification, and a second modification that is 2'-F. The nucleic acid of the invention may also include a phosphorothioate modification and/or a deoxy modification which may be present in or between the terminal 1, 2 or 3 nucleotides of each or any end of each or both strands.

The nucleic acid of the invention may be conjugated to a ligand, to form a conjugate.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. The endosomolytic component may contain a chemical group which undergoes a change in charge or protonation in response to a change in pH. The endosomolytic component may be linear or branched.

Ligands can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics. Ligands can include a naturally occurring substance, such as a protein, carbohydrate, or lipid. The ligand may be a recombinant or synthetic molecule.

Ligands can also include targeting groups, e.g. a cell or tissue targeting agent. The targeting ligand may be a lectin, glycoprotein, lipid or protein.

Other examples of ligands include dyes, intercalating agents, cross-linkers, porphyrins, polycyclic aromatic hydrocarbons, artificial endonucleases or a chelator, lipophilic molecules, alkylating agents, phosphate, amino, mercapto, PEG, MPEG, alkyl, substituted alkyl, radiolabelled markers, enzymes, haptens, transport/absorption facilitators, synthetic ribonucleases, or imidazole clusters.

Ligands can be proteins, e.g. glycoproteins or peptides. Ligands may also be hormones or hormone receptors. They may also include non-peptidic species, such as lipids, lectins, carbohydrates, vitamins, or cofactors.

The ligand may be a substance such as a drug which can increase the uptake of the nucleic acid into a cell, for example, by disrupting the cell's cytoskeleton.

The ligand may increase uptake of the nucleic acid into the cell by activating an inflammatory response. Such ligands include tumour necrosis factor alpha (TNF-alpha), interleukin-1 beta, or gamma interferon.

The ligand may be a lipid or lipid-based molecule. The lipid or lipid-based molecule preferably binds a serum protein. Preferably, the lipid-based ligand binds human serum albumin (HSA). A lipid or lipid-based molecule can increase resistance to degradation of the conjugate, increase targeting or transport into target cell, and/or can adjust binding to a serum protein. A lipid-based ligand can be used to modulate binding of the conjugate to a target tissue.

The ligand may be a steroid. Preferably, the ligand is cholesterol or a cholesterol derivative.

The ligand may be a moiety e.g. a vitamin, which is taken up by a target cell. Exemplary vitamins include vitamin A, E, K, and the B vitamins. Vitamins may be taken up by a proliferating cell, which may be useful for delivering the nucleic acid to cells such as malignant or non-malignant tumour cells.

The ligand may be a cell-permeation agent, such as a helical cell-permeation agent. Preferably such an agent is amphipathic.

The ligand may be a peptide or peptidomimetic. A peptidomimetic is a molecule capable of folding into a defined three-dimensional structure similar to a natural peptide. The peptide or peptidomimetic ligand may include naturally occurring or modified peptides, or both. A peptide or peptidomimetic can be a cell permeation peptide, cationic peptide, amphipathic peptide, or hydrophobic peptide. The peptide moiety can be a dendrimer peptide, constrained peptide, or crosslinked peptide. The peptide moiety can include a hydrophobic membrane translocation sequence. The peptide moiety can be a peptide capable of carrying large polar molecules such as peptides, oligonucleotides, and proteins across cell membranes, e.g. sequences from the HIV Tat protein (GRKKRRQRRRPPQ) and the Drosophila Antennapedia protein (RQIKIWFQNRRMKWKK). Preferably the peptide or peptidomimetic is a cell targeting peptide, e.g. arginine-glycine-aspartic acid (RGD)-peptide.

The ligand may be a cell permeation peptide that is capable of permeating, for example, a microbial cell or a mammalian cell.

The ligand may be a pharmacokinetic modulator. The pharmacokinetic modulator may be lipophiles, bile acids, steroids, phospholipid analogues, peptides, protein binding agents, PEG, vitamins, etc.

When two or more ligands are present, the ligands can all have the same properties, all have different properties, or some ligands have the same properties while others have different properties. For example, a ligand can have targeting properties, have endosomolytic activity or have PK modulating properties. In a preferred embodiment, all the ligands have different properties.

Ligands can be coupled to the nucleic acid at the 3'-end, 5'-end, and/or at an internal position. Preferably the ligand is coupled to the nucleic acid via an intervening tether or linker.

In some embodiments the nucleic acid is a double-stranded nucleic acid. In a double-stranded nucleic acid the ligand may be attached to one or both strands. In some embodiments, a double-stranded nucleic acid contains a ligand conjugated to the sense strand. In other embodiments, a double-stranded nucleic acid contains a ligand conjugated to the antisense strand.

Ligands can be conjugated to nucleobases, sugar moieties, or internucleosidic linkages of nucleic acid molecules. Conjugation to purine nucleobases or derivatives thereof can occur at any position including endocyclic and exocyclic atoms. Conjugation to pyrimidine nucleotides or derivatives thereof can also occur at any position. Conjugation to sugar moieties of nucleosides can occur at any carbon atom. Conjugation to internucleosidic linkages may occur at the phosphorus atom of a phosphorus-containing linkage or at an oxygen, nitrogen, or sulphur atom bonded to the phosphorus atom. For amine- or amide-containing internucleosidic linkages, conjugation may occur at the nitrogen atom of the amine or amide or to an adjacent carbon atom.

The ligand is typically a carbohydrate, e.g. a monosaccharide, disaccharide, trisaccharide, tetrasaccharide or polysaccharide. The ligand may be conjugated to the nucleic acid by a linker. The linker may be a monovalent, bivalent, or trivalent branched linker.

Means for efficient delivery of oligonucleotides, in particular double stranded nucleic acids of the invention, to cells in vivo is important and requires specific targeting and substantial protection from the extracellular environment, particularly serum proteins. One method of achieving specific targeting is to conjugate a targeting moiety or ligand to the nucleic acid. The targeting moiety helps in targeting the nucleic acid to the required target site and there is a need to conjugate appropriate targeting moieties for the desired receptor sites for the conjugated molecules to be taken up by the cells such as by endocytosis. The targeting moiety or ligand can be any moiety or ligand that is capable of targeting a specific receptor.

For example, the asialoglycoprotein receptor (ASGP-R) is a high capacity receptor, which is highly abundant on hepatocytes. One of the first disclosures of triantennary cluster glycosides was in U.S. Pat. No. 5,885,968. Conjugates having three GalNAc ligands and comprising phosphate groups are known and are described in Dubber et al. (2003). The ASGP-R shows a 50-fold higher affinity for N-Acetyl-D-Galactosylamine (GalNAc) than D-Gal.

Hepatocytes expressing the lectin (asialoglycoprotein receptor; ASGPR), which recognizes specifically terminal β-galactosyl subunits of glycosylated proteins or other oligosaccharides (P. H. Weigel et. al., 2002) can be used for targeting a drug to the liver by covalent coupling of galactose or galactosamine to the drug substance (Ishibashi, S.; et. al., J Biol. Chem. 1994 Nov. 11; 269(45):27803-6). Furthermore the binding affinity can be significantly increased by the multi-valency effect, which is achieved by the repetition of the targeting unit (Biessen E A, et al., J Med Chem. 1995 Apr. 28; 38(9):1538-46).

The ASGPR is a mediator for an active endosomal transport of terminal β-galactosyl containing glycoproteins, thus ASGPR is highly suitable for targeted delivery of drug candidates like nucleic acids, which have to be delivered into a cell (Akinc et al.).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

The saccharide may be selected from N-acetyl galactosamine, mannose, galactose, glucose, glucosamine and fucose. The saccharide may be N-acetyl galactosamine (GalNAc).

The ligand may comprise (i) one or more N-acetyl galactosamine (GalNAc) moieties and derivatives thereof, and (ii) a linker, wherein the linker conjugates the GalNAc moieties to a nucleic acid as defined in any preceding aspects. The linker may be a bivalent or trivalent or tetravalent branched structure. The nucleotides may be modified as defined herein.

"GalNAc" refers to 2-(Acetylamino)-2-deoxy-D-galactopyranose, commonly referred to in the literature as N-acetyl galactosamine. Reference to "GalNAc" or "N-acetyl galactoseamine" includes both the β-form: 2-(Acetylamino)-2-deoxy-β-D-galactopyranose and the α-form: 2-(Acetylamino)-2-deoxy-α-D-galactopyranose. Both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

The ligand may comprise GalNAc.

The ligand may comprise a compound of formula I:

$$[S-X^1-P-X^2]_3\text{-}A\text{-}X^3- \quad\quad (I)$$

wherein:

S represents a saccharide, wherein the saccharide is N-acetyl galactosamine;

$X^1$ represents $C_3$-$C_6$ alkylene or $(-CH_2-CH_2-O)_m(-CH_2)_2-$ wherein m is 1, 2, or 3;

P is a phosphate or modified phosphate (preferably a thiophosphate);

$X^2$ is alkylene or an alkylene ether of the formula $(-CH_2)_n-O-CH_2-$ where n=1-6;

A is a branching unit;

$X^3$ represents a bridging unit;

wherein a nucleic acid according to the present invention is conjugated to $X^3$ via a phosphate or modified phosphate (preferably a thiophosphate).

In formula I, branching unit "A" branches into three in order to accommodate the three saccharide ligands. The branching unit is covalently attached to the ligands and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

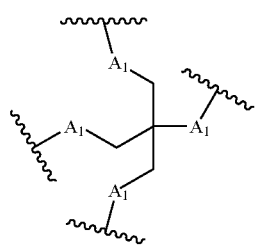

and

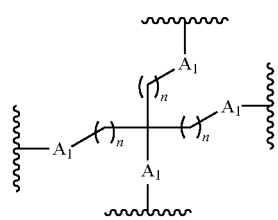

wherein each $A_1$ independently represents O, S, C=O or NH; and each n independently represents an integer from 1 to 20.

The branching unit may have a structure selected from:

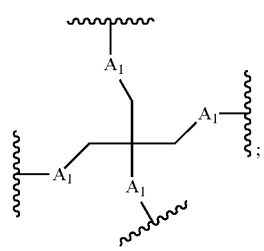

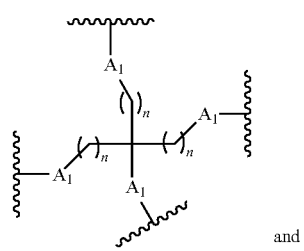

and

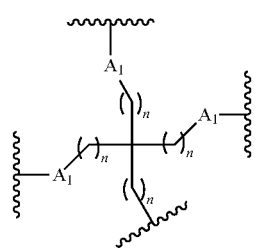

wherein each $A_1$ independently represents O, S, C=O or NH; and each n independently represents an integer from 1 to 20.

The branching unit may have a structure selected from:

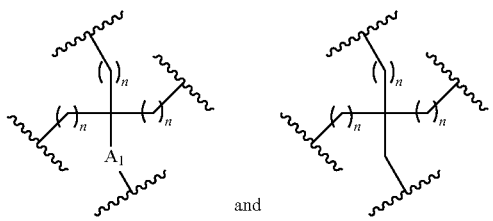

and wherein $A_1$ is O, S, C=O or NH; and
each n independently represents an integer from 1 to 20.

The branching unit may have the structure:

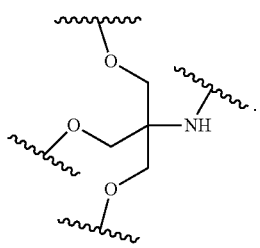 [SMILES: *NC(CO*)(CO*)CO*]

The branching unit may have the structure:

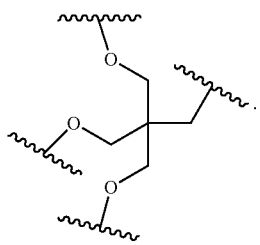 [SMILES: *CC(CO*)(CO*)CO*]

The branching unit may have the structure:

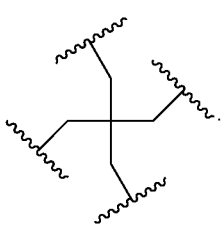 [SMILES: *CC(C*)(C*)C*]

Optionally, the branching unit consists of only a carbon atom.

The "$X^3$" portion is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_4$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

The ligand may comprise a compound of formula (II):

$$[S-X^1-P-X^2]_3\text{-}A\text{-}X^3 \quad (II)$$

wherein:
S represents a saccharide;
$X^1$ represents $C_3$—C alkylene or an ethylene glycol stem (—$CH_2$—$CH_2$—O)$_m$(—$CH_2$)$_2$—
wherein m is 1, 2, or 3;
P is a phosphate or modified phosphate (preferably a thiophosphate);
$X^2$ is $C_1$—C alkylene;
A is a branching unit selected from:

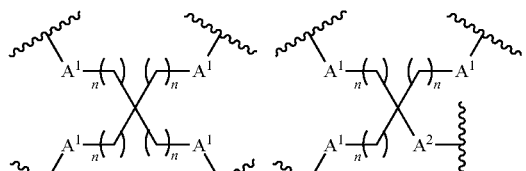

$A^1$ = O, NH        $A^1$ = O, NH
n = 1 to 4           A2 = NH, $CH_2$, O
                     n = 1 to 4

$X^3$ is a bridging unit;
wherein a nucleic acid according to the present invention is conjugated to $X^3$ via a phosphate or modified phosphate (preferably a thiophosphate).

Branching unit A may have the structure:

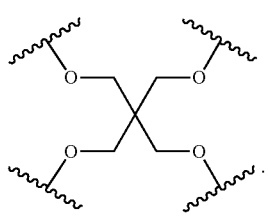 [SMILES: *OCC(CO*)(CO*)CO*]

Branching unit A may have the structure:

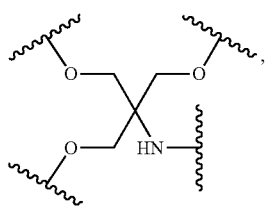

wherein X³ is attached to the nitrogen atom.

X³ may be $C_1$-$C_{20}$ alkylene. Preferably, X³ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

The ligand may comprise a compound of formula (III):

$$[S—X^1—P—X^2]_3\text{-}A\text{-}X^3 \qquad (III)$$

wherein:
S represents a saccharide;
X¹ represents $C_3$—C alkylene or an ethylene glycol stem (—$CH_2$—CH2-O)$_m$(—$CH_2$)$_2$—
wherein m is 1, 2, or 3;
P is a phosphate or modified phosphate (preferably a thiophosphate);
X² is an alkylene ether of formula —$C_3H_6$—O—$CH_2$—;
A is a branching unit;
X³ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—$C_8H_{16}$—, wherein in each case the —$CH_2$— group is linked to A,
wherein a nucleic acid according to the present invention is conjugated to X³ via a phosphate or modified phosphate (preferably a thiophosphate).

The branching unit may comprise carbon. Preferably, the branching unit is carbon.

X³ may be selected from the group consisting of —$CH_2$—O—$C_4H_8$-, —$CH_2$—O—$C_5H_{10}$—, —$CH_2$—O—$C_6H_{12}$—, —$CH_2$—$CH_{14}$—, and —$CH_2$—$C_8H_{16}$—. Preferably, X³ is selected from the group consisting of —$CH_2$—O—$C_4H_8$—, —$CH_2$—O—$C_6H_{12}$— and —$CH_2$—O—$C_8H_{16}$.

For any of the above aspects, P represents a modified phosphate group. P can be represented by:

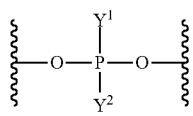

wherein Y¹ and Y² each independently represent =O, =S, —O⁻, —OH, —SH, —BH₃, —OCH₂CO₂, —OCH₂CO₂Rˣ, —OCH₂C(S)ORˣ, and —ORˣ, wherein Rˣ represents $C_1$-$C_6$ alkyl and wherein

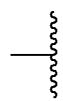

indicates attachment to the remainder of the compound.

By modified phosphate it is meant a phosphate group wherein one or more of oxygens is replaced. Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, Y¹ may represent —OH and Y² may represent =O or =S; or
Y¹ may represent —O⁻ and Y² may represent =O or =S;
Y¹ may represent =O and Y² may represent —$CH_3$, —SH, —ORˣ, or —BH₃
Y¹ may represent =S and Y² may represent —$CH_3$, ORˣ or —SH.

It will be understood by the skilled person that in certain instances there will be delocalisation between Y¹ and Y².

Preferably, the modified phosphate group is a thiophosphate group. Thiophosphate groups include bithiophosphate (i.e. where Y¹ represents =S and Y² represents —S⁻) and monothiophosphate (i.e. where Y¹ represents —O⁻ and Y² represents =S, or where Y¹ represents =O and Y² represents —S⁻). Preferably, P is a monothiophosphate. The inventors have found that conjugates having thiophosphate groups in replacement of phosphate groups have improved potency and duration of action in vivo.

P may also be an ethylphosphate (i.e. where Y¹ represents =O and Y² represents OCH₂CH₃).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

For any of the above aspects, the saccharide may be selected from N-acetyl with one or more of galactosamine, mannose, galactose, glucose, glucosamine and fructose. Preferably, the saccharide is two molecules of N-acetyl galactosamine (GalNAc). The compounds of the invention may have 3 ligands which are each preferably N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

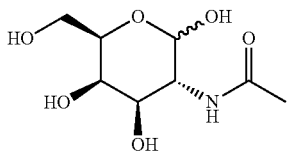

2-(Acetylamino)-2-deoxy-D-galactopyranose

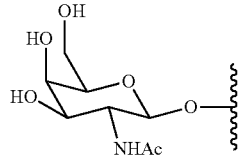

2-(Acetylamino)-2-deoxy-β-D-galactopyranose

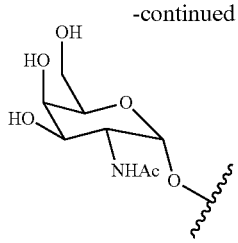

2-(Acetylamino)-2-deoxy-α-D-galactopyranose

For any of the above compounds of formula (III), $X^1$ may be an ethylene glycol stem $(-CH_2-CH_2-O)_m(-CH_2)_2-$ wherein m is 1, 2, or 3. $X^1$ may be $(-CH_2-CH_2-O)(-CH_2)_2-$. $X^1$ may be $(-CH_2-CH_2-O)_2(-CH_2)_2-$. $X^1$ may be $(-CH_2-CH_2-O)_3(-CH_2)_2-$. Preferably, $X^1$ is $(-CH_2-CH_2-O)_2(-CH_2)_2-$. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

For compounds of formula (III), $X^2$ represents an alkylene ether of formula $-C_3H_6-O-CH_2-$ i.e. $C_3$ alkoxy methylene, or $-CH_2CH_2CH_2OCH_2-$.

The present invention therefore additionally provides a conjugated nucleic acid having one of the following structures:

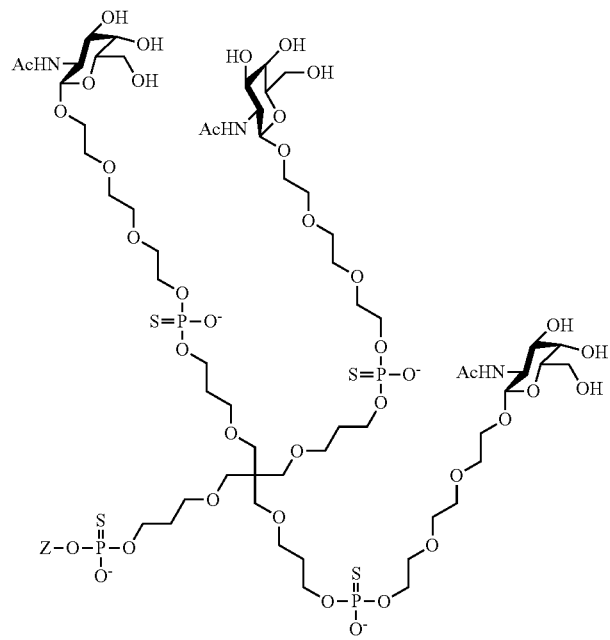

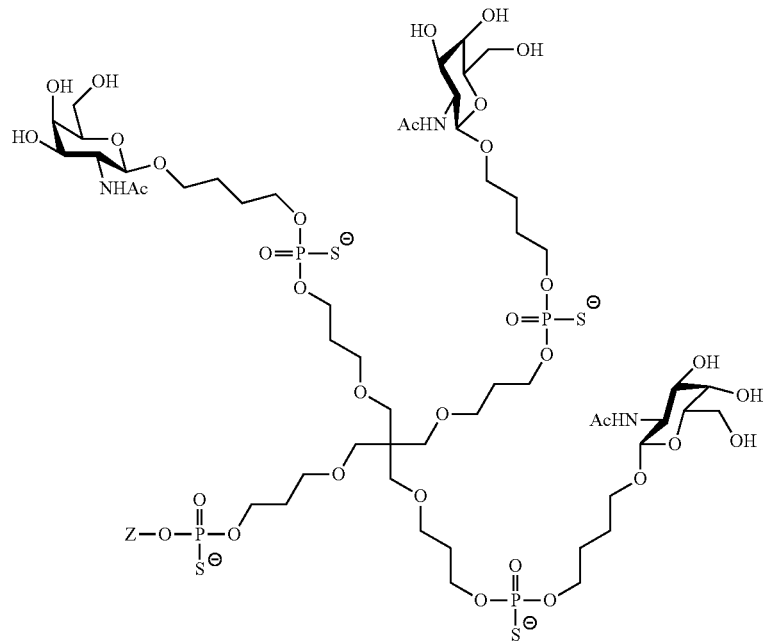

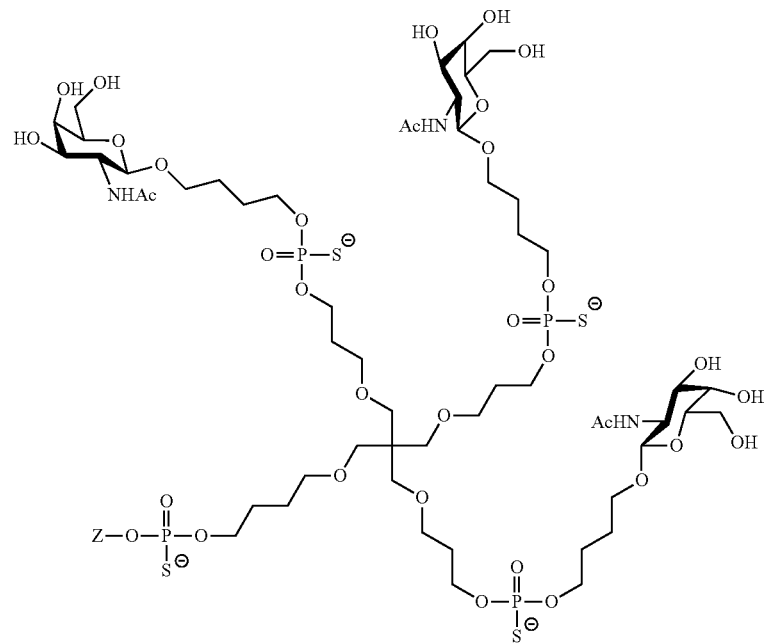
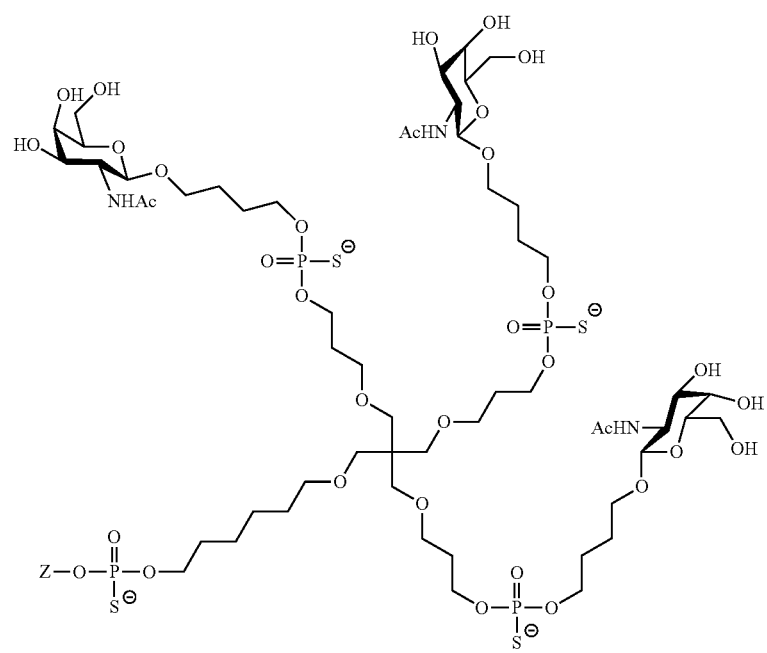

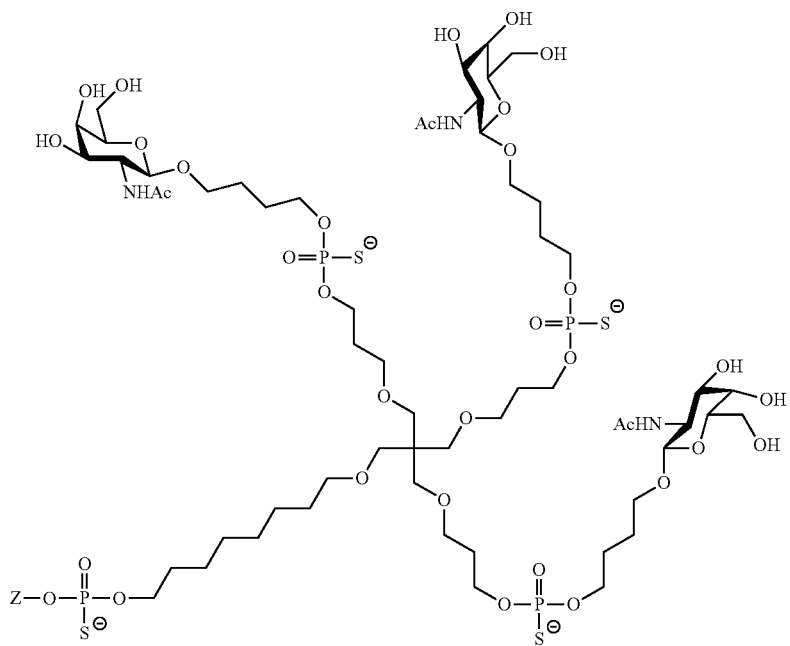
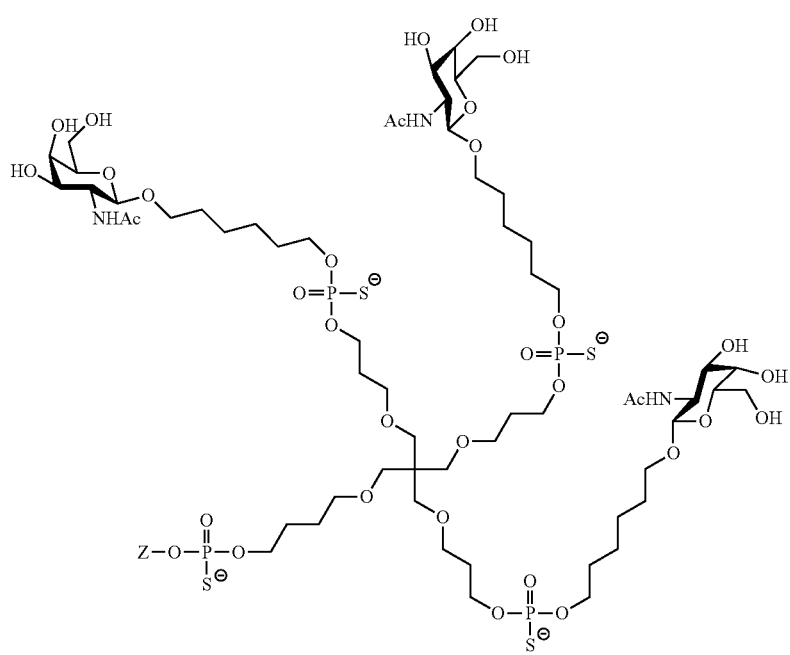

-continued

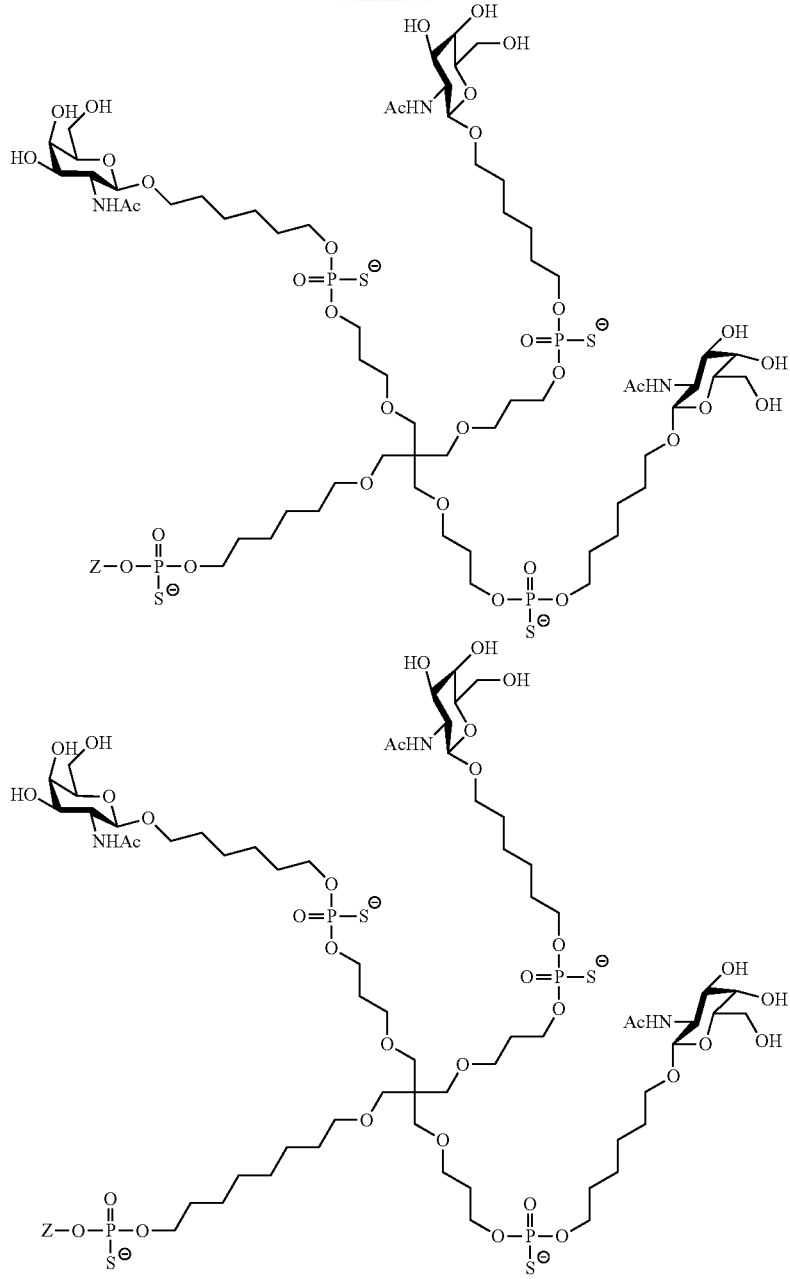

wherein Z represents a nucleic acid as defined herein before.

A ligand of formula (I), (II) or (III) can be attached at the 3'-end of the first (antisense) strand and/or at any of the 3'- and/or 5'-end of the second (sense) strand. The nucleic acid can comprise more than one ligand of formula (I), (II), or (III). However, a single ligand of formula (I), (II) or (III) is preferred because a single such ligand is sufficient for efficient targeting of the nucleic acid to the target cells.

Preferably, the 5'-end of the first (antisense) strand is not attached to a ligand of formula (I), (II) or (III), since a ligand in this position can potentially interfere with the biological activity of the nucleic acid.

A nucleic acid with a single ligand of formula (I), (II) or (III) at the 5'-end of a strand is easier and therefore cheaper to synthesis than the same nucleic acid with the same ligand at the 3'-end. Preferably therefore, a single ligand of any of formulae (I), (II) or (III) is covalently attached to (conjugated with) the 5'-end of the second strand of the nucleic acid.

In one embodiment, the nucleic acid is conjugated to a ligand that comprises a lipid, and more preferably a ligand that comprises a cholesterol.

A conjugate of the invention can comprise any nucleic acid as disclosed herein conjugated to any ligand or ligands as disclosed herein.

The present invention also relates to a conjugate for inhibiting expression of a target gene in a cell, said conjugate comprising a nucleic acid portion, comprising the nucleic acid of any aspect of the invention, and at least one ligand portion, said at least one ligand portion comprising a linker moiety, preferably a serinol-derived linker moiety, and a targeting ligand for in vivo targeting of cells and being conjugated exclusively to the 3' and/or 5' ends of one or both RNA strands, wherein the 5' end of the first RNA strand is not conjugated, wherein:

(i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or (ii) both the second RNA strand and the first RNA strand are conjugated at the 3' ends to the targeting ligand and the 5' end of the second RNA strand is not conjugated.

In an embodiment of the present invention, the second RNA strand (i.e. the sense strand) is conjugated at the 5' end to a targeting ligand, the first RNA strand (i.e. the antisense strand) is conjugated at the 3' end to the targeting ligand and the 3' end of the second RNA strand (i.e. the sense strand) is not conjugated, such that a conjugate with the schematic structure as shown in FIG. 16A is formed.

In an embodiment of the present invention, the second RNA strand (i.e. the sense strand) is conjugated at the 5' end to the targeting ligand, the second RNA strand (i.e. the sense strand) is also conjugated at the 3' end to the targeting ligand and the 3' end of the first RNA strand (i.e. the antisense strand) is not conjugated, such that a conjugate with the schematic structure as shown in FIG. 16B is formed.

In an embodiment of the present invention, both the second RNA strand (i.e. the sense strand) and the first RNA strand (i.e. the antisense strand) are conjugated at the 3' ends to the targeting ligand and the 5' end of the second RNA strand (i.e. the sense strand) is not conjugated, such that a conjugate with the schematic structure as shown in FIG. 16C is formed.

In an embodiment of the present invention, the second RNA strand (i.e. the sense strand) is conjugated at the 5' end to the targeting ligand and both the second RNA strand (i.e. the sense strand) and the first RNA strand (i.e. the antisense strand) are also conjugated at the 3' ends to the targeting ligand, such that a conjugate with the schematic structure as shown in FIG. 16D is formed.

In any one of the above embodiments, ∼∼∼ indicates the linker which conjugates the ligand to the ends of the nucleic acid portion; the ligand may be a GalNAc moiety such as GalNAc; and the schematic structure as shown in FIG. 16E represents the nucleic acid portion.

These schematic diagrams are not intended to limit the number of nucleotides in the first or second strand, nor do the diagrams represent any kind of limitation on complementarity of the bases or any other limitation.

The ligands may be monomeric or multimeric (e.g. dimeric, trimeric, etc.).

Suitably, the ligands are monomeric, thus containing a single targeting ligand moiety, e.g. a single GalNAc moiety.

Alternatively, the ligands may be dimeric ligands wherein the ligand portions comprise two linker moieties, such as serinol-derived linker moieties or non-serinol linker moieties, each linked to a single targeting ligand moiety.

The ligands may be trimeric ligands wherein the ligand portions comprise three linker moieties, such as serinol-derived linker moieties or non-serinol linker moieties, each linked to a single targeting ligand moiety.

The two or three serinol-derived linker moieties may be linked in series e.g. as shown below:

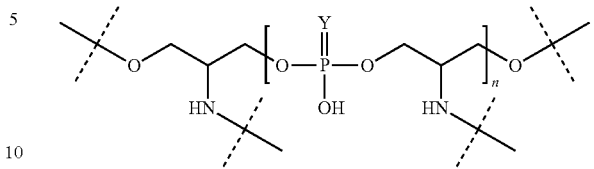

wherein n is 1 or 2 and Y is S or 0.

Preferably, the ligands are monomeric.

Suitably, the conjugated RNA strands are conjugated to a targeting ligand via a linker moiety including a further linker wherein the further linker is or comprises a saturated, unbranched or branched $C_{1-15}$ alkyl chain, wherein optionally one or more carbons (for example 1, 2 or 3 carbons, suitably 1 or 2, in particular 1) is/are replaced by a heteroatom selected from O, N, $S(O)_p$, wherein p is 0, 1 or 2 (for example a $CH_2$ group is replaced with O, or with NH, or with S, or with $SO_2$ or a —$CH_3$ group at the terminus of the chain or on a branch is replaced with OH or with $NH_2$) wherein said chain is optionally substituted by one or more oxo groups (for example 1 to 3, such as 1 group).

Suitably, the linker moiety is a serinol-derived linker moiety.

More suitably, the further linker comprises a saturated, unbranched $C_{1-15}$ alkyl chain wherein one or more carbons (for example 1, 2 or 3 carbons, suitably 1 or 2, in particular 1) is/are replaced by an oxygen atom.

More suitably, the further linker comprises a PEG-chain.

More suitably, the further linker comprises a saturated, unbranched $C_{1-15}$ alkyl chain.

More suitably, the further linker comprises a saturated, unbranched $C_{1-6}$ alkyl chain.

More suitably, the further linker comprises a saturated, unbranched $C_4$ or $C_6$ alkyl chain, e.g. a $C_4$ alkyl chain.

In an embodiment, ∼∼∼ is a linking moiety of formula (V):

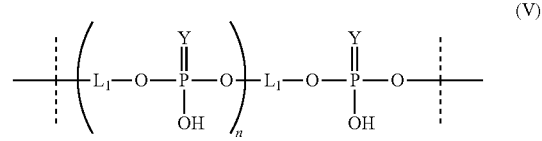

wherein n, Y and $L_1$ are defined below and the O of the phosphoro-group is attached to the terminal oligonucleoside of the RNA strands.

Thus in an embodiment, the targeting ligand portion is a linking moiety of formula (VI):

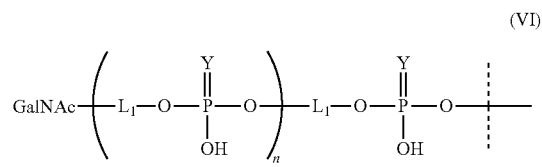

wherein n, Y and $L_1$ are defined below and the O of the phosphoro-group is attached to the terminal oligonucleoside of the RNA strands.

Suitably,  is a linking moiety of formula (XIV):

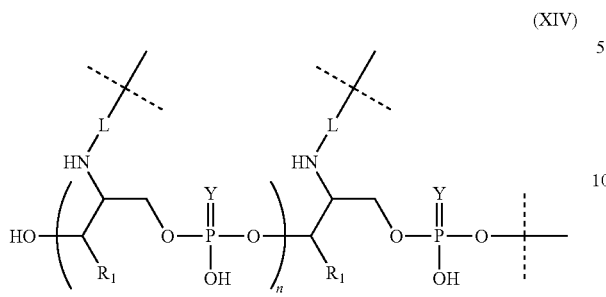

(XIV)

wherein n, Y, $R_1$ and L are defined below, L is connected to the targeting ligand e.g. GalNAc and the O of the phosphoro-group is attached to the terminal oligonucleoside of the RNA strands.

Suitably, the targeting ligand portion is a linking moiety of formula (IV):

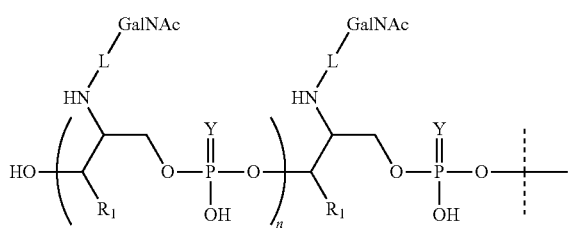

(IV)

wherein n, Y, $R_1$ and L are defined below and the O of the phosphoro-group is attached to the terminal oligonucleoside of the RNA strands.

Suitably,  is a linking moiety of formula (VII):

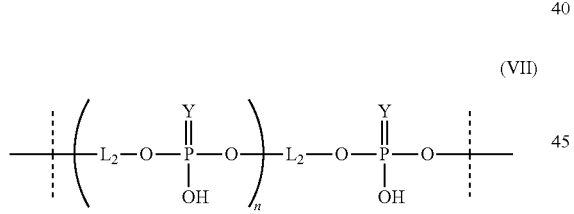

(VII)

wherein n, Y and $L_2$ are defined below and the O of the phosphoro-group is attached to the terminal oligonucleoside of the RNA strands.

Suitably, the targeting ligand portion is a linking moiety of formula (VI):

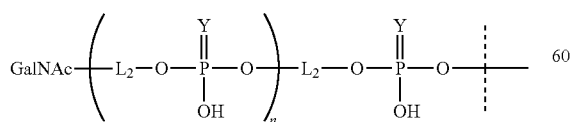

(VIII)

wherein n, Y and $L_2$ are defined below and the O of the phosphoro-group is attached to the terminal oligonucleoside of the RNA strands.

Suitably,  is a linking moiety of formula (IX):

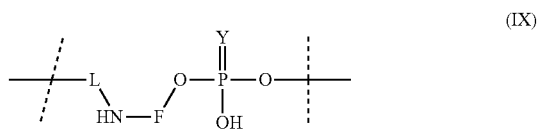

(IX)

wherein F, Y and L are defined below and the O of the phosphoro-group is attached to the terminal oligonucleoside of the RNA strands.

Suitably, the targeting ligand portion is a linking moiety of formula (IXa):

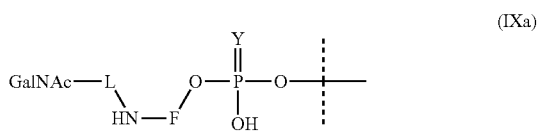

(IXa)

wherein F, Y and L are defined below and the O of the phosphoro-group is attached to the terminal oligonucleoside of the RNA strands.

Suitably, L is:

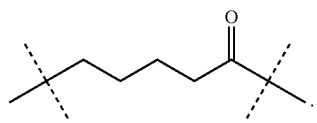

In any of the above structures, suitably the ligands are selected from GalNAc and galactose moieties, especially GalNAc moieties. Alternatively, GalNAc may be replaced by another targeting ligand, e.g. a saccharide.

In an embodiment of the invention, the first RNA strand is a compound of formula (X):

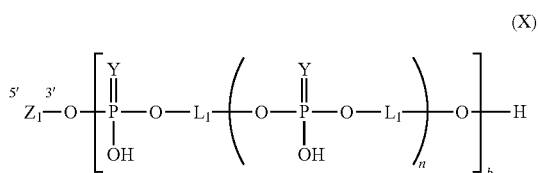

(X)

wherein b is 0 or 1; and
the second RNA strand is a compound of formula (XI):

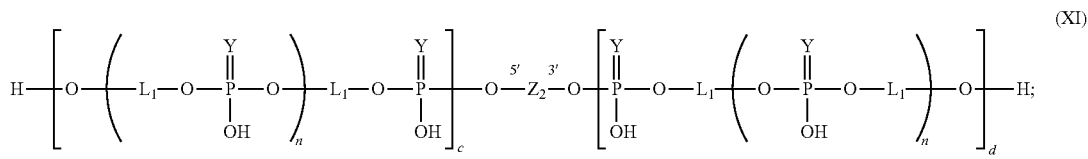

wherein:
c and d are independently 0 or 1;
$Z_1$ and $Z_2$ are the RNA portions of the first and second RNA strands respectively;
Y is O or S;
n is 0, 1, 2 or 3; and
$L_1$ is a linker to which a ligand is attached;
and wherein b+c+d is 2 or 3.

Suitably, the first RNA strand is a compound of formula (XV):

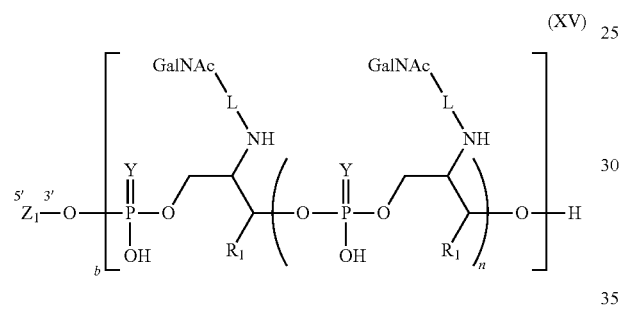

wherein b is 0 or 1; and
the second RNA strand is a compound of formula (XVI):

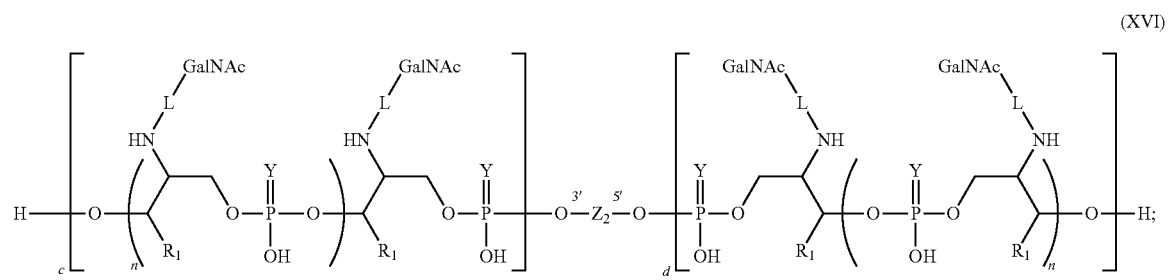

wherein c and d are independently 0 or 1;
wherein:
$Z_1$ and $Z_2$ are the RNA portions of the first and second RNA strands respectively;
Y is O or S;
$R_1$ is H or methyl;
n is 0, 1, 2 or 3; and
L is the same or different in formulae (XV) and (XVI) and is selected from the group consisting of:
—$(CH_2)_r$—C(O)—, wherein r=2-12;
—$CH_2$—$CH_2$—O$)_s$—$CH_2$—C(O)—, wherein s=1-5;
—$(CH_2)_t$—CO—NH—$(CH_2)_t$—NH—C(O)—, wherein t is independently is 1-5;
—$(CH_2)_u$—CO—NH—$(CH_2)_u$—C(O)—, wherein u is independently is 1-5; and
—$(CH_2)_v$—NH—C(O)—, wherein v is 2-12; and
wherein the terminal C(O) (if present) is attached to the NH group;
and wherein b+c+d is 2 or 3.

Suitably, the first RNA strand is a compound of formula (XII):

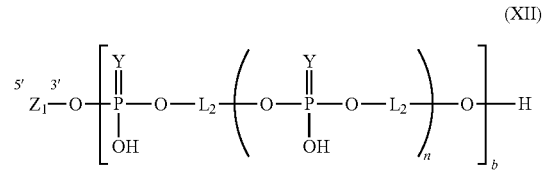

wherein b is 0 or 1; and
the second RNA strand is a compound of formula (XIII):

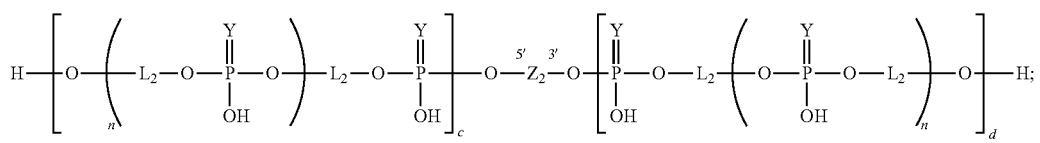

wherein:
c and d are independently 0 or 1;
$Z_1$ and $Z_2$ are the RNA portions of the first and second RNA strands respectively;
Y is O or S;
n is 0, 1, 2 or 3; and
$L_2$ is the same or different in formulae (XII) and (XIII) and is the same or different in moieties bracketed by b, c and d, and is selected from the group consisting of:

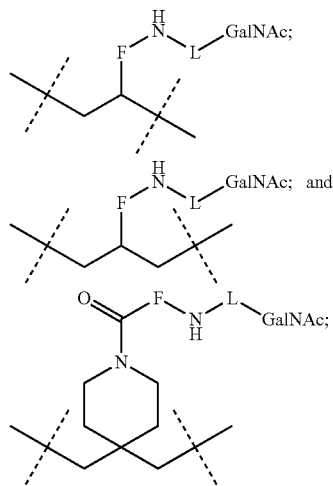

or
n is 0 and $L_2$ is:

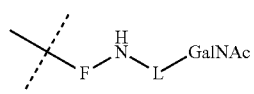

and the terminal OH group is absent such that the following moiety is formed:

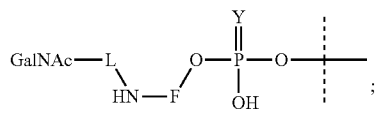

wherein
F is a saturated branched or unbranched (such as unbranched) $C_{1-8}$alkyl (e.g. $C_{1-6}$ alkyl) chain wherein one of the carbon atoms is optionally replaced with an oxygen atom provided that said oxygen atom is separated from another heteroatom (e.g. an O or N atom) by at least 2 carbon atoms;

L is the same or different in formulae (XII) and (XIII) and is selected from the group consisting of:
—$(CH_2)_r$—C(O)—, wherein r=2-12;
—$(CH_2—CH_2—O)_s$—$CH_2$—C(O)—, wherein s=1-5;
—$(CH_2)_t$—CO—NH—$(CH_2)_t$—NH—C(O)—, wherein t is independently is 1-5;
—$(CH_2)_u$—CO—NH—$(CH_2)_u$—C(O)—, wherein u is independently is 1-5; and
—$(CH_2)_v$—NH—C(O)—, wherein v is 2-12; and
wherein the terminal C(O) (if present) is attached to the NH group;
and wherein b+c+d is 2 or 3.

In any one of the above formulae where GalNAc is present, the GalNAc may be substituted for any other targeting ligand, such as those mentioned herein.

Suitably, b is 0, c is 1 and d is 1; b is 1, c is 0 and d is 1; b is 1, c is 1 and d is 0; or b is 1, c is 1 and d is 1.

More suitably, b is 0, c is 1 and d is 1; b is 1, c is 0 and d is 1; or b is 1, c is 1 and d is 1.

Most suitably, b is 0, c is 1 and d is 1.

In one embodiment, Y is O. In another embodiment, Y is S.

In one embodiment, $R_1$ is H or methyl. In one embodiment, $R_1$ is H. In another embodiment, $R_1$ is methyl.

In one embodiment, n is 0, 1, 2 or 3. Suitably, n is 0.

In one embodiment, L is selected from the group consisting of:
—$(CH_2)_r$C(O)—, wherein r=2-12;
—$(CH_2—CH_2—O)_s$—$CH_2$—C(O)—, wherein s=1-5;
—$(CH_2)_t$—CO—NH—$(CH_2)_t$—NH—C(O)—, wherein t is independently is 1-5;
—$(CH_2)_u$—CO—NH—$(CH_2)_u$—C(O)—, wherein u is independently is 1-5; and
—$(CH_2)_v$—NH—C(O)—, wherein v is 2-12;
wherein the terminal C(O) is attached to the NH group.

Suitably, L is —$(CH_2)_r$C(O)—, wherein r=2-12. Suitably, r=2-6. More suitably, r=4 or 6 e.g. 4.

Suitably, L is:

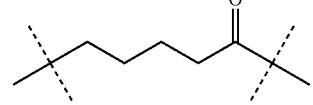

Example F moieties include $(CH_2)_{1-6}$ e.g. $(CH_2)_{1-4}$ e.g. $CH_2$, $(CH_2)_4$, $(CH_2)_5$ or $(CH_2)_6$, or $CH_2O(CH_2)_{2-3}$, e.g. $CH_2O(CH_2)CH_3$.

Suitably, $L_2$ is:

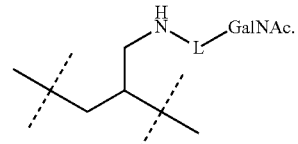

Suitably, L₂ is:

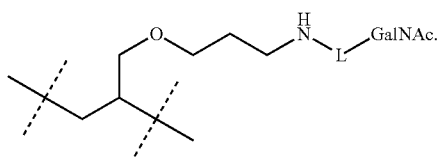

Suitably, L₂ is:

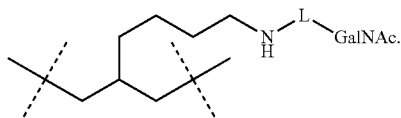

Suitably, L₂ is:

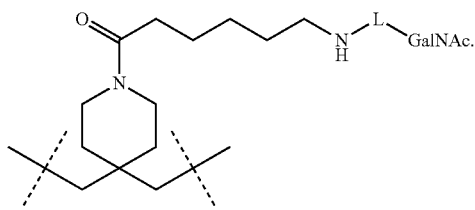

Suitably, n is 0 and L₂ is:

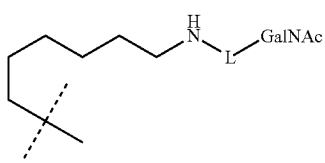

and the terminal OH group is absent such that the following moiety is formed:

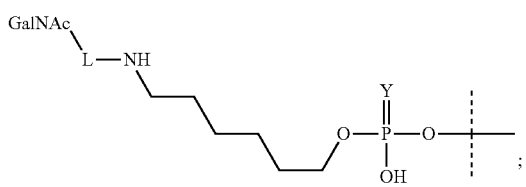

wherein Y is as defined elsewhere herein.

Within the moiety bracketed by b, c and d, L₂ is typically the same. Between moieties bracketed by b, c and d, L₂ may be the same or different. In an embodiment, L₂ in the moiety bracketed by c is the same as the L₂ in the moiety bracketed by d. In an embodiment, L₂ in the moiety bracketed by c is not the same as L₂ in the moiety bracketed by d. In an embodiment, the L₂ in the moieties bracketed by b, c and d is the same, for example when the linker moiety is a serinol-derived linker moiety.

Serinol derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

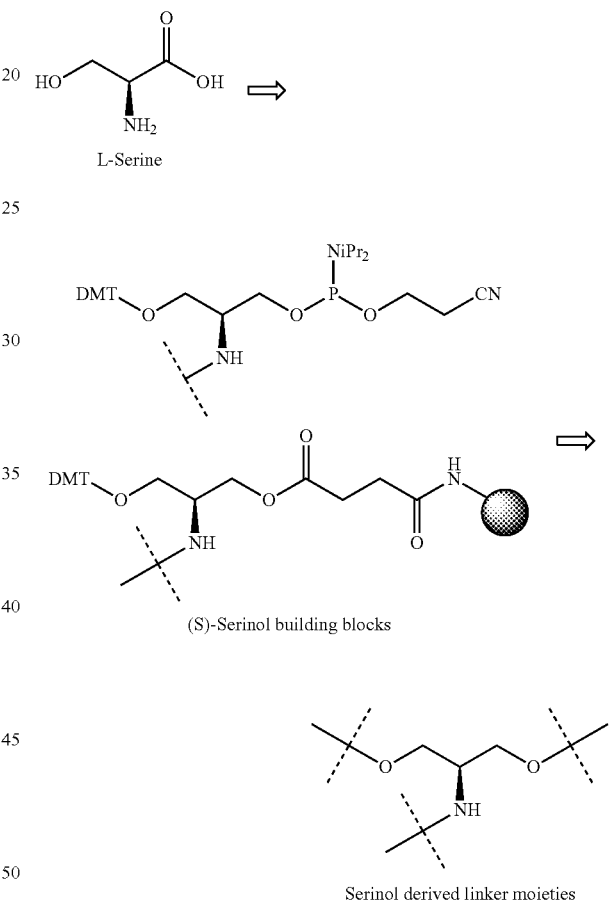

i.e. is based on an (S)-serinol-amidite or (S)-serinol succinate solid supported building block derived from L-serine isomer.

In one embodiment, the targeted cells are hepatocytes.

The invention provides as a further aspect, a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene to be inhibited and wherein the said first and/or second strand includes a phosphorodithioate linkage between the at least two terminal 3' nucleotides and/or the second strand includes a phosphorodithioate linkage between the at least two terminal 5' nucleotides, and wherein the nucleic acid molecule is directly or indirectly conjugated to a ligand via a linker.

The nucleic acid may be conjugated to a ligand as herein described. The nucleotides of the first and/or second strand may be modified, as herein described.

The ligand may be GalNAc.

A cleavable linking group is a linker which is stable outside the cell but is cleaved upon entry into a target cell. Cleavage releases the two parts the linker is holding together.

In a preferred embodiment, the nucleic acid of the invention comprises a cleavable linking group that is cleaved at least 10 times or more, preferably at least 100-fold faster in a target cell or under a first reference condition (which can, for example, be selected to mimic or represent intracellular conditions) than in the blood of a subject, or under a second reference condition (which can, for example, be selected to mimic or represent conditions found in the blood or serum).

Cleavable linking groups are susceptible to cleavage agents, e.g. pH, redox potential, or the presence of degradative molecules. Degradative molecules include oxidative or reductive enzymes, reductive agents (such as mercaptans), esterases, endosomes or agents than can create an acidic environment, enzymes that can hydrolyze or degrade an acid cleavable linking group by acting as a general acid, peptidases, and phosphatases.

A cleavable linking group may be a disulphide bond, which is susceptible to pH.

A linker may include a cleavable linking group that is cleavable by a particular enzyme. The type of cleavable linking group incorporated into a linker can depend on the target cell. For example, a linker that includes an ester group is preferred when a liver cell is the target. Linkers that contain peptide bonds can be used when targeting cells rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In one aspect, the cleavable linking group may be a redox cleavable linking group. The redox cleavable linking group may be a disulphide linking group.

In one aspect, the linking group may be a phosphate-based cleavable linking group. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—.

In one aspect, the cleavable linking group may be an acid cleavable linking group. Preferably the acid cleavable linking group are cleaved in environments where the pH is 6.5 or lower, or are cleaved by agents such as enzymes that can act as a general acid. Examples of acid cleavable linking groups include but are not limited to hydrazones, esters, and esters of amino acids. Acid cleavable groups can have the general formula —C=NN—; C(O)O, or —OC(O). A preferred embodiment is a linking group where the carbon attached to the oxygen of the ester (the alkoxy group) is an aryl group, substituted alkyl group, or tertiary alkyl group such as dimethyl pentyl or t-butyl.

In one embodiment, the cleavable linking group may be an ester-based cleavable linking group. Examples of ester-based cleavable linking groups include but are not limited to esters of alkylene, alkenylene and alkynylene groups.

In one embodiment, the cleavable linking group may be a peptide-based cleavable linking group. Peptide-based cleavable linking groups are peptide bonds formed between amino acids to yield oligopeptides (e.g., dipeptides, tripeptides etc.) and polypeptides. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where RA and RB are the R groups of the two adjacent amino acids.

Synthesis of Single Strands

Example compounds can be synthesised according to methods described below and known to the person skilled in the art. Assembly of the oligonucleotide chain and linker building blocks may, for example, be performed by solid phase synthesis applying phosphoramidite methodology. Solid phase synthesis may start from a base or modified building block loaded Icaa CPG. Phosphoramidite synthesis coupling cycle consists of 1) DMT-removal, 2) chain elongation using the required DMT-masked phosphoramidite and an activator, which may be benzylthiotetrazole (BTT), 3) capping of non-elongated oligonucleotide chains, followed by oxidation of the P(III) to P(V) either by Iodine (if phosphodiester linkage is desired) or EDITH (if phosphorothioate or phosphorodithioate linkage is desired) and again capping (Cap/Ox/Cap or Cap/Thio/Cap). In case a phosphorodithioate linkage is desired, phosphoramidite synthesis coupling cycle consists of 1) DMT-removal, 2) chain elongation using the required DMT-masked thiophosphoramidite, 3) capping of non-elongated oligonucleotide chains, followed by oxidation of the P(III) to P(V) by EDITH and again capping (Cap/Thio/Cap). For the on column conjugation of a trivalent tree-like GalNAc cluster the same phosphoramidite synthesis cycle was applied with using the necessary trivalent branching amidite ST41-phos followed by another round of the synthesis cycle usingthe GalNAc amidite ST23-phos. The necessary building blocks are either commercially available or synthesis is described below.

All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products was proved by LC-MS analysis.

Synthesis of the phosphoramidite derivatives of ST41 (ST41-phos) as well as ST23 (ST23-phos) can be performed as described in WO2017/174657:

ST41-phos:

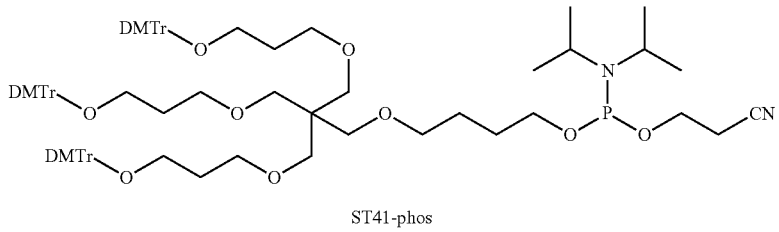

ST41-phos

ST23-phos:

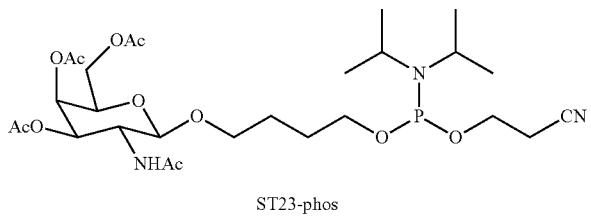

ST23-phos

Synthesis of Double Strands

In order to obtain double strand conjugates, the necessary individual single strands are dissolved in a concentration of 60 OD/mL in H$_2$O. Both individual oligonucleotide solutions can be added together to a reaction vessel. For easier reaction monitoring a titration can be performed. The first strand is added in 25% excess over the second strand as determined by UV-absorption at 260 nm. The reaction mixture is heated e.g. to 80° C. for 5 min and then slowly cooled to RT. Double strand formation may be monitored by ion pairing reverse phase HPLC. From the UV-area of the residual single strand the needed amount of the second strand can be calculated and added to the reaction mixture. The reaction is heated e.g. to 80° C. again and slowly cooled to RT. This procedure can be repeated until less than 10% of residual single strand is detected.

The nucleic acid as described herein may be formulated with a lipid in the form of a liposome. Such a formulation may be described in the art as a lipoplex. The composition with a lipid/liposome may be used to assist with delivery of the nucleic acid of the invention to the target cells. The lipid delivery system herein described may be used as an alternative to a conjugated ligand. The modifications herein described may be present when using the nucleic acid of the invention with a lipid delivery system or with a ligand conjugate delivery system.

Such a lipoplex may comprise a lipid composition comprising:
  i) a cationic lipid, or a pharmaceutically acceptable salt thereof;
  ii) a steroid;
  iii) a phosphatidylethanolamine phospholipid;
  iv) a PEGylated lipid.

The cationic lipid may be an amino cationic lipid.

The cationic lipid may have the formula (XIX):

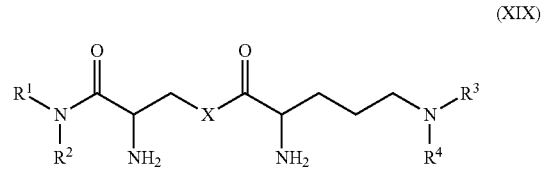

(XIX)

or a pharmaceutically acceptable salt thereof, wherein:
  X represents O, S or NH;
  $R^1$ and $R^2$ each independently represents a $C_4$-$C_{22}$ linear or branched alkyl chain or a $C_4$-$C_{22}$ linear or branched alkenyl chain with one or more double bonds, wherein the alkyl or alkenyl chain optionally contains an intervening ester, amide or disulfide;
  when X represents S or NH, $R^3$ and $R^4$ each independently represent hydrogen, methyl, ethyl, a mono- or polyamine moiety, or $R^3$ and $R^4$ together form a heterocyclyl ring;
  when X represents O, $R^3$ and $R^4$ each independently represent hydrogen, methyl, ethyl, a mono- or polyamine moiety, or $R^3$ and $R^4$ together form a heterocyclyl ring, or $R^3$ represents hydrogen and $R^4$ represents C(NH)(NH$_2$).

The cationic lipid may have the formula (XIXA):

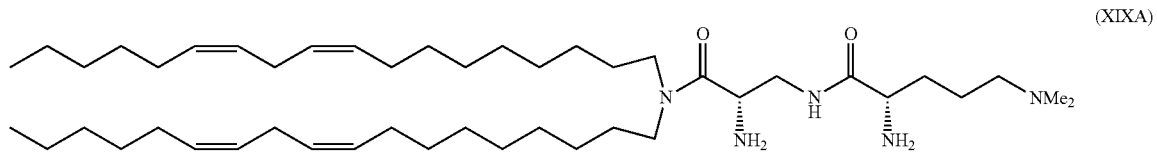

(XIXA)

or a pharmaceutically acceptable salt thereof.

The cationic lipid may have the formula (XIXB):

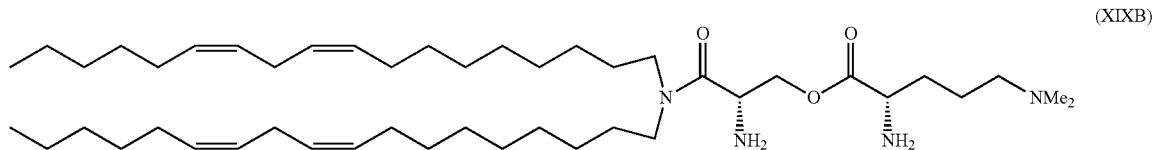 [SMILES: CCCCC/C=C\C/C=C\CCCCCCCCN(CCCCCCCC/C=C\C/C=C\CCCCC)C(=O)[C@@H](N)COC(=O)[C@@H](N)CCCN(C)C]

(XIXB)

or a pharmaceutically acceptable salt thereof.

The content of the cationic lipid component may be from about 55 mol % to about 65 mol % of the overall lipid content of the composition. In particular, the cationic lipid component is about 59 mol % of the overall lipid content of the composition.

The compositions can further comprise a steroid. The steroid may be cholesterol. The content of the steroid may be from about 26 mol % to about 35 mol % of the overall lipid content of the lipid composition. More particularly, the content of steroid may be about 30 mol % of the overall lipid content of the lipid composition.

The phosphatidylethanolamine phospholipid may be selected from the group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the composition.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the composition.

The content of the cationic lipid component in the composition may be from about 55 mol % to about 65 mol % of the overall lipid content of the lipid composition, preferably about 59 mol % of the overall lipid content of the lipid composition.

The composition may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

The composition may comprise a cationic lipid having the structure

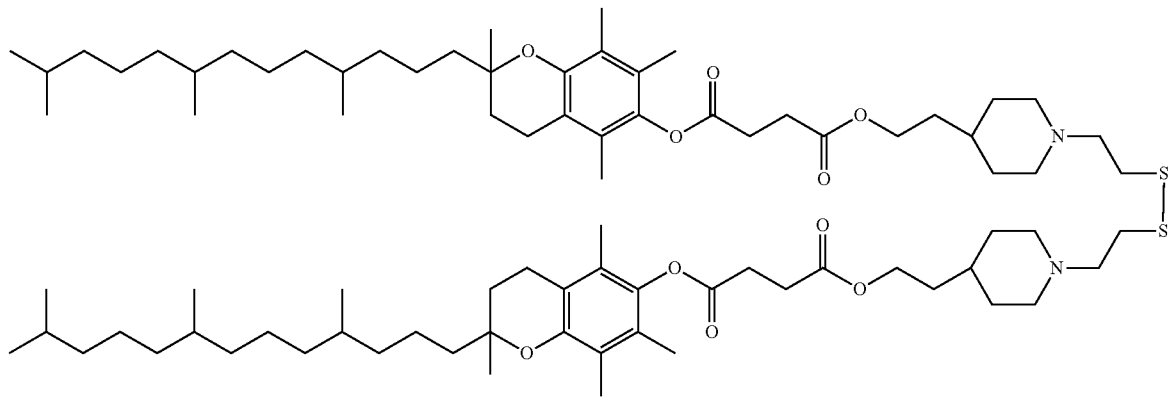 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

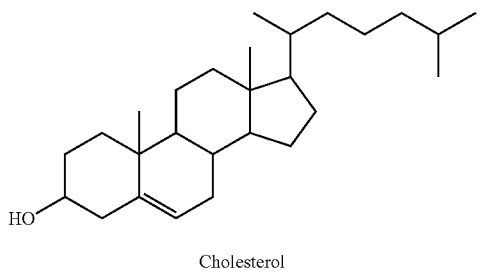 [SMILES: CC(C)CCCC(C)C1CCC2C3CC=C4CC(O)CCC4(C)C3CCC12C]

Cholesterol a phosphatidylethanolamine phospholipid having the structure

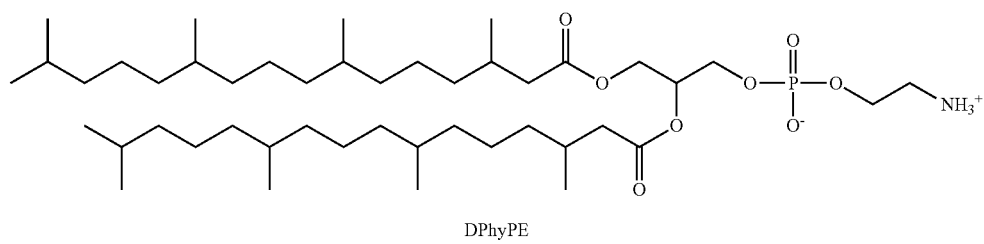 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE and a PEGylated lipid having the structure

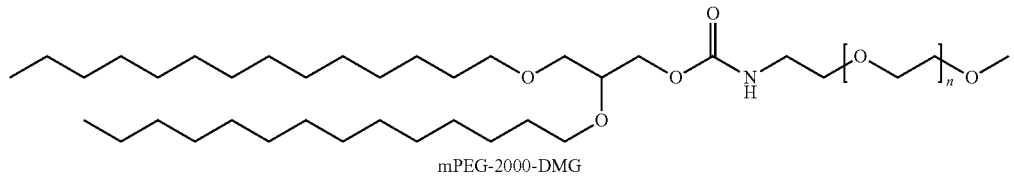

mPEG-2000-DMG

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

The present invention also provides pharmaceutical compositions comprising a nucleic acid or conjugated nucleic acid of the invention. The pharmaceutical compositions may be used as medicaments or as diagnostic agents, alone or in combination with other agents. For example, a nucleic acid or conjugated nucleic acid of the invention can be combined with a delivery vehicle (e.g., liposomes) and excipients, such as carriers, diluents. Other agents such as preservatives and stabilizers can also be added. Methods for the delivery of a nucleic acid or conjugated nucleic acid are known in the art and within the knowledge of the person skilled in the art.

The nucleic acid or conjugated nucleic acid of the present invention can also be administered in combination with other therapeutic compounds, either administered separately or simultaneously, e.g., as a combined unit dose. The invention also includes a pharmaceutical composition comprising a nucleic acid or conjugated nucleic acid according to the present invention in a physiologically/pharmaceutically acceptable excipient, such as a stabilizer, preservative, diluent, buffer, and the like.

The pharmaceutical composition may be specially formulated for administration in solid or liquid form. The composition may be formulated for oral administration, parenteral administration (including, for example, subcutaneous, intramuscular, intravenous, or epidural injection), topical application, intravaginal or intrarectal administration, sublingual administration, ocular administration, transdermal administration, or nasal administration. Delivery using subcutaneous or intravenous methods are preferred.

Dosage levels for the medicament and pharmaceutical compositions of the invention can be determined by those skilled in the art by routine experimentation. In one embodiment, a unit dose may contain between about 0.01 mg/kg and about 100 mg/kg body weight of nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Dosage levels may also be calculated via other parameters such as, e.g., body surface area.

The pharmaceutical composition may be a sterile injectable aqueous suspension or solution, or in a lyophilized form. In one embodiment, the pharmaceutical composition may comprise lyophilized lipoplexes or an aqueous suspension of lipoplexes. The lipoplexes preferably comprises a nucleic acid of the present invention. Such lipoplexes may be used to deliver the nucleic acid of the invention to a target cell either in vitro or in vivo.

The pharmaceutical compositions and medicaments of the present invention may be administered to a mammalian subject in a pharmaceutically effective dose. The mammal may be selected from humans, dogs, cats, horses, cattle, pig, goat, sheep, mouse, rat, hamster and guinea pig.

A further aspect of the invention relates to a nucleic acid or conjugated nucleic acid of the invention or the pharmaceutical composition comprising the same for use in the treatment or prevention of a disease or disorder. The invention includes a pharmaceutical composition comprising one or more RNAi molecules according to the present invention in a physiologically/pharmaceutically acceptable excipient, such as a stabiliser, preservative, diluent, buffer and the like.

The pharmaceutical composition may be a sterile injectable aqueous suspension or solution, or in a lyophilised form.

Pharmaceutically acceptable compositions may comprise a therapeutically-effective amount of one or more nucleic acid(s) in any embodiment according to the invention, taken alone or formulated with one or more pharmaceutically acceptable carriers, excipient and/or diluents.

Examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatine; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

Stabilisers may be agents that stabilise the nucleic acid agent, for example a protein that can complex with the nucleic acid, chelators (e.g. EDTA), salts, RNAse inhibitors, and DNAse inhibitors.

In some cases it is desirable to slow the absorption of the drug from subcutaneous or intramuscular injection in order to prolong the effect of a drug. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The nucleic acid described herein may be capable of inhibiting the expression of a target gene in a cell. The nucleic acid described herein may be capable of partially inhibiting the expression of a target gene in a cell. Inhibition may be complete, i.e. 0% of the expression level of target gene expression in the absence of the nucleic acid of the invention. Inhibition of target gene expression may be partial, i.e. it may be 15%, 20%, 30%, 40%, 50%, 60%, 70%, 75%, 80%, 85%, 90%, 95% of target gene expression in the absence of a nucleic acid of the invention. Inhibition may last 4 weeks, 5 weeks, 6 weeks, 7 weeks, 8 weeks, 10 weeks, 11 weeks, 12 weeks, 13 weeks, 14 weeks or up to 3 months, when used in a subject, such as a human subject. The nucleic acid or composition comprising the nucleic acid composition may be for use once, every week, every two weeks, every three weeks, every four weeks, every five weeks, every six weeks, every seven weeks, or every eight weeks. The nucleic acid may be for use subcutaneously, intravenously or using any other application routes such as oral, rectal or intraperitoneal.

In cells and/or subjects treated with or receiving the nucleic acid of the present invention, the target gene expression may be inhibited compared to untreated cells and/or subjects by at least about 30%, 35%, 40%, 45%, 50%, 55%, 60%, 65%, 70%, 75%, 80%, 85%, 90%, 95%, 98%, or 100%. The level of inhibition may allow treatment of a disease associated with target gene expression or overexpression, or may allow further investigation into the functions of the target gene product.

The target gene may be Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erkl/2 gene, PCNA (p21) gene, MYB gene, JU gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21 (WAF I/CIPI) gene, mutations in the p27 (KIPI) gene, mutations in the PPM ID gene, mutations in the RAS gene, mutations in the caveolin I gene, mutations in the MIB I gene, mutations in the MTAI gene, mutations in the M68 gene, mutations in tumour suppressor genes, and mutations in the p53 tumour suppressor gene.

A further aspect of the invention relates to a nucleic acid or conjugated nucleic acid of the invention in the manufacture of a medicament for treating or preventing a disease or disorder.

Also included in the invention is a method of treating or preventing a disease or disorder comprising administration of a pharmaceutical composition comprising a nucleic acid or conjugated nucleic acid as described herein, to an individual in need of treatment. The nucleic acid composition may be administered twice every week, once every week, every two weeks, every three weeks, every four weeks, every five weeks, every six weeks, every seven weeks, or every eight weeks. The nucleic acid may be administered to the subject subcutaneously, intravenously or using any other application routes such as oral, rectal or intraperitoneal.

In one embodiment, a subject is administered an initial dose and one or more maintenance doses of a nucleic acid agent. The maintenance dose or doses can be the same or lower than the initial dose, e.g., one-half less of the initial dose. The maintenance doses are, for example, administered no more than once every 2, 5, 10, or 30 days. The treatment regimen may last for a period of time which will vary depending upon the nature of the particular disease, its severity and the overall condition of the patient.

In one embodiment, the composition includes a plurality of nucleic acid agent species. In another embodiment, the nucleic acid agent species has sequences that are non-overlapping and non-adjacent to another species with respect to a naturally occurring target sequence. In another embodiment, the plurality of nucleic acid agent species is specific for different naturally occurring target genes. In another embodiment, the nucleic acid agent is allele specific.

The nucleic acid or conjugated nucleic acid of the present invention can also be administered or for use in combination with other therapeutic compounds, either administered separately or simultaneously, e.g. as a combined unit dose.

The nucleic acid or conjugated nucleic acid of the present invention can be produced using routine methods in the art including chemically synthesis or expressing the nucleic acid either in vitro (e.g., run off transcription) or in vivo. For example, using solid phase chemical synthesis or using an expression vector. In one embodiment, the expression vector can produce the nucleic acid of the invention in a target cell.

Methods for the synthesis of the nucleic acid described herein are known to persons skilled in the art.

Example compounds were synthesised according to methods known to the person skilled in the art. Assembly of the oligonucleotide chain and linker building blocks may be performed by solid phase synthesis applying phosphoramidite methodology. Scheme 1 shows trebler amidite C4xlt-phos and GalNAc amidite (ST23-phos) needed to assemble trivalent GalNAc tree-like cluster during solid phase oligonucleotide synthesis. Synthesis of C4XLT-phos as well as ST23-phos may be carried out as described in WO2017/174657.

Scheme 1: Structures of trebler amidites and GalNAc amidites used for on column conjugation of trivalent tree-like GalNAc clusters.

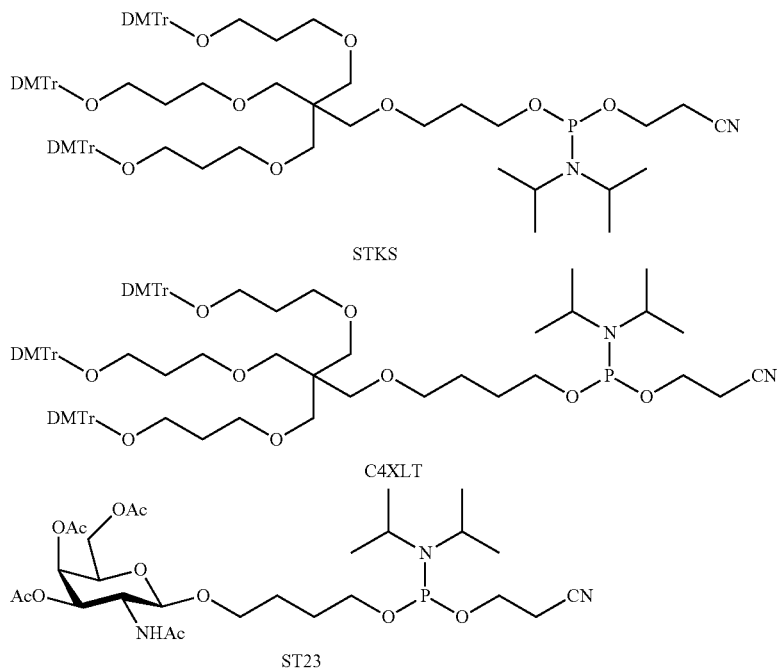

Oligonucleotides synthesis of tree-like GalNAc-cluster conjugated siRNA is outlined in scheme 2 shown in FIG. 11.

Oligonucleotide chain assembly may be commenced using base loaded support e.g. 5'DMT-2'FdU-succinate-Icaa-CPG as in example compound A0149 (STS12009V15L4B). For the introduction of the first phosphodithioate linkage the phosphoramidite synthesis coupling cycle consisting of 1) DMT-removal, 2) chain elongation using the required DMT-masked thiophosphoamidite, 3) capping of non-elongated oligonucleotide chains, followed by oxidation of the P(III) to P(V) EDITH and again capping (Cap/Thio/Cap). Afterwards, the synthesis cycle may be repeated using standard DMT-phosphoamidites and Cap/Ox/Cap or Cap/Thio/Cap depending on whether phosphodiester or phosphorothioate linkage is desired until full length of the product is reached. For the on column conjugation of a trivalent tree-like GalNAc cluster the same synthesis cycle may be applied with using the necessary trivalent branching amidite C4XLT followed by another round of the synthesis cycle using the GalNAc amidite ST23. Upon completion of this last synthesizer step, the oligonucleotide may be cleaved from the solid support and set free from additional protective groups by methylamine treatment (in presence of 20 mM DTT if phosphorodithioate linkages are present). The crude product may be then purified by AEX-HPLC applying a NaCl gradient. Excess salt from IEX purification was removed by SEC to yield the final product.

All final single stranded products may be analysed by AEX-HPLC to prove their purity. Purity may be given in % FLP (% full length product) which is the percentage of the UV-area under the assigned product signal in the UV-trace of the AEX-HPLC analysis of the final product. Identity of the respective single stranded products (non-modified or GalNAc conjugated oligonucleotides) may be proved by LC-MS analysis.

Duplex formation of the double stranded siRNA may be achieved by equimolar addition of the respective single strands and heating to 80° C. Slow cooldown to RT can result in full double strand formation. The duplex formation may be followed by IP-RP-HPLC (ion-pairing reverse-phase HPLC). The double strand purity may be given in % double strand which is the percentage of the UV-area under the assigned product signal in the UV-trace of the IP-RP-HPLC analysis.

The invention also provides a nucleic acid according to any aspect of the invention described herein, wherein the first RNA strand has a terminal 5' (E)-vinylphosphonate nucleotide, and the terminal 5' (E)-vinylphosphonate nucleotide is preferably linked to the second nucleotide in the first strand by a phosphodiester linkage.

In one embodiment, the first strand may include more than 1 phosphodiester linkage.

In one embodiment, the first strand may comprise phosphodiester linkages between at least the terminal three 5' nucleotides.

In one embodiment, the first strand may comprise phosphodiester linkages between at least the terminal four 5' nucleotides.

In one embodiment, the first strand may comprise formula (XVII):

$$(vp)\text{-}N_{(po)}[N_{(po)}]_n\text{—} \qquad (XVII)$$

where '(vp)-' is the 5' (E)-vinylphosphonate, 'N' is a nucleotide, 'po' is a phosphodiester linkage, and n is from 1 to (the total number of nucleotides in the first strand −2), preferably wherein n is from 1 to (the total number of nucleotides in the first strand −3), more preferably wherein n is from 1 to (the total number of nucleotides in the first strand −4).

In one embodiment, the first strand may include at least one phosphorothioate (ps) linkage.

In one embodiment, the first strand may further comprise a phosphorothioate linkage between the terminal two 3' nucleotides or phosphorothioate linkages between the terminal three 3' nucleotides.

In one embodiment, the linkages between the other nucleotides in the first strand are phosphodiester linkages.

In one embodiment, the first strand may include more than 1 phosphorothioate linkage.

In a further embodiment, the second strand may comprise a phosphorothioate linkage between the terminal two 3' nucleotides or phosphorothioate linkages between the terminal three 3' nucleotides.

In another further embodiment, the second strand may comprise a phosphorothioate linkage between the terminal two 5' nucleotides or phosphorothioate linkages between the terminal three 5' nucleotides.

In an embodiment, the terminal 5' (E)-vinylphosphonate nucleotide is an RNA nucleotide.

A terminal 5' (E)-vinylphosphonate nucleotide is a nucleotide wherein the natural phosphate group at the 5'-end has been replaced with a E-vinylphosphonate, in which the bridging 5'-oxygen atom of the terminal nucleotide of the 5' phosphorylated strand is replaced with a methynyl (—CH=) group:

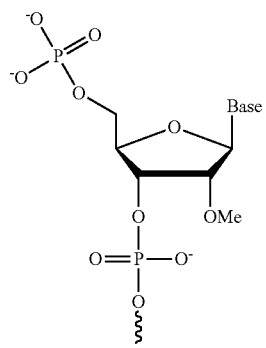

Nucleotides with a natural phosphate at the 5'-end

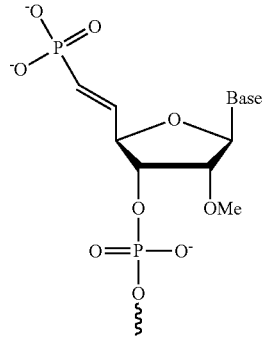

Nucleotides with a E-vinylphosphonate at the 5'-end

5' (E) vinylphosphonate is a 5' phosphate mimic. A biological mimic is a molecule that is capable of carrying out the same function as and is structurally very similar to the original molecule that is being mimicked. In the context of the present invention, 5' (E) vinylphosphonate mimics the function of a normal 5' phosphate, e.g. enabling efficient RISC loading. In addition, because of its slightly altered structure, 5' (E) vinylphosphonate is capable of stabilizing the 5'-end nucleotide by protecting it from dephosphorylation by enzymes such as phosphatases.

One aspect of the invention is a nucleic acid as disclosed herein for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first strand includes modified nucleotides or unmodified nucleotides at a plurality of positions in order to facilitate processing of the nucleic acid by RISC.

In one aspect "facilitate processing by RISC" means that the nucleic acid can be processed by RISC, for example any modification present will permit the nucleic acid to be processed by RISC, suitably such that siRNA activity can take place.

A nucleic acid as disclosed herein, wherein the nucleotides at positions 2 and 14 from the 5' end of the first strand are not modified with a 2' O-methyl modification, and the nucleotide on the second strand which corresponds to position 13 of the first strand is not modified with a 2'O-methyl modification.

A nucleotide on the second strand that "corresponds to" a position on the first strand is suitably the nucleotide that base pairs with that nucleotide on the first strand.

In one aspect the nucleotide on the second strand which corresponds to position 13 of the first strand is the nucleotide that forms a base pair with position 13 of the first strand.

In one aspect the nucleotide on the second strand which corresponds to position 11 of the first strand is the nucleotide that forms a base pair with position 11 of the first strand.

In one aspect the nucleotide on the second strand which corresponds to position 12 of the first strand is the nucleotide that forms a base pair with position 12 of the first strand.

This nomenclature may be applied to other positions of the second strand. For example, in a 19-mer nucleic acid which is double stranded and blunt ended, position 13 of the first strand would pair with position 7 of the second strand. Position 11 of the first strand would pair with position 9 of the second strand. This nomenclature may be applied to other positions of the second strand.

The nucleotide that corresponds to position 13 of the first strand is suitably position 13 of the second strand, counting from the 3' of the second strand, starting from the first nucleotide of the double stranded region. Likewise position 11 of the second strand is suitably the 11$^{th}$ nucleotide from the 3' of the second strand, starting from the first nucleotide of the double stranded region. This nomenclature may be applied to other positions of the second strand.

In one aspect, in the case of a partially complementary first and second strand, the nucleotide on the second strand that "corresponds to" a position on the first strand may not necessarily form a base pair if that position is the position in which there is a mismatch, but the principle of the nomenclature still applies.

Preferred is a first and second strand that are fully complementary over the duplex region (ignoring any overhang regions) and there are no mismatches within the double stranded region of the nucleic acid.

Also preferred are:

A nucleic acid as disclosed herein, wherein the nucleotides at positions 2 and 14 from the 5' end of the first strand are not modified with a 2' O-methyl modification, and the nucleotide on the second strand which corresponds to position 11 of the first strand is not modified with a 2'O-methyl modification.

A nucleic acid as disclosed herein, wherein the nucleotides at positions 2 and 14 from the 5' end of the first strand are not modified with a 2' O-methyl modification, and the nucleotides on the second strand which corresponds to position 11 and 13 of the first strand are not modified with a 2' O-methyl modification.

In one aspect the nucleotide on the second strand which corresponds to position 12 of the first strand is not modified with a 2' O-methyl modification. This limitation on the nucleic acid may be seen with any other limitation described herein.

Therefore another aspect of the invention is a nucleic acid as disclosed herein, wherein the nucleotides at positions 2 and 14 from the 5' end of the first strand are not modified with a 2' O-methyl modification, and the nucleotides on the second strand which corresponds to position 11-13 of the first strand are not modified with a 2' O-methyl modification.

A nucleic acid as disclosed herein, wherein the nucleotides at positions 2 and 14 from the 5' end of the first strand are not modified with a 2' O-methyl modification, and the nucleotides on the second strand which correspond to position 11, or 13, or 11 and 13, or 11-13 of the first strand are modified with a 2' fluoro modification.

A nucleic acid as disclosed herein, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are not modified with a 2' O-methyl modification.

A nucleic acid as disclosed herein, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

A nucleic acid as disclosed herein wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

A nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2 O' methyl, other 2' sugar modifications, in particular a 2' H modification resulting in a DNA nucleotide.

A nucleic acid as disclosed herein comprising no more than 20%, such as no more than 15% such as more than 10%, of nucleotides which have 2' modifications that are not 2' O methyl modifications on the first and/or second strand, preferably as a percentage of the total nucleotides of both the first and second strands.

A nucleic acid as disclosed herein comprising no more than 20%, (such as no more than 15% or no more than 10%) of 2' fluoro modifications on the first and/or second strand, preferably as a percentage of the total nucleotides of both strands.

A nucleic acid as disclosed herein, wherein all nucleotides are modified with a 2' O-methyl modification except positions 2 and 14 from the 5' end of the first strand and the nucleotides on the second strand which correspond to position 11, or 13, or 11 and 13, or 11-13 of the first strand. Preferably the nucleotides that are not modified with 2' O-methyl are modified with fluoro at the 2' position.

Preferred is a nucleic acid as disclosed herein wherein all nucleotides of the nucleic acid are modified at the 2' position of the sugar. Preferably these nucleotides are modified with a 2'-fluoro modification where the modification is not a 2' O-Methyl modification.

Nucleic acids of the invention may comprise one or more nucleotides modified at the 2' position with a 2' H, and therefore having a DNA nucleotide within the nucleic acid. Nucleic acids of the invention may comprise DNA nucleotides at positions 2 and/or 14 of the first strand counting from the 5' end of the first strand. Nucleic acids may comprise DNA nucleotides on the second strand which correspond to position 11, or 13, or 11 and 13, or 11-13 of the first strand.

In one aspect there is no more than one DNA per nucleic acid of the invention.

Nucleic acids of the invention may comprise one or more LNA nucleotides. Nucleic acids of the invention may comprise LNA nucleotides at positions 2 and/or 14 of the first strand counting from the 5' end of the first strand. Nucleic acids may comprise LNA on the second strand which correspond to position 11, or 13, or 11 and 13, or 11-13 of the first strand.

In one aspect the nucleic acid is modified on the first strand with alternating 2-O methyl modifications and 2 fluoro modifications, and positions 2 and 14 (starting from the 5' end) are modified with 2' fluoro. Preferably the second strand is modified with 2' fluoro modifications at nucleotides on the second strand which correspond to position 11, or 13, or 11 and 13, or 11-13 of the first strand. Preferably the second strand is modified with 2' fluoro modifications at positions 11-13 counting from the 3' end starting at the first position of the complementary (double stranded) region, and the remaining modifications are naturally occurring modifications, preferably 2' O-methyl.

In one aspect the nucleic acids of the invention comprise one or more inverted ribonucleotides, preferably an inverted adenine, using a 5'-5' linkage or a 3'-3' linkage, preferably a 3'-3' linkage at the 3' end of the second strand.

In one aspect the nucleic acid comprises one or more phosphorodithioate linkages, such as 1, 2, 3 or 4 phosphorodithioate linkages. Preferably there are up to 4 phosphorodithioate linkages, one each at the 5' and 3' ends of the first and second strands.

All the features of the nucleic acids can be combined with all other aspects of the invention disclosed herein.

In particular, preferred are nucleic acids which are siRNA molecules wherein the nucleotides at positions 2 and 14 from the 5' end of the first strand are not modified with a 2' O-methyl modification, and the nucleic acid comprises one or more or all of:

(i) an inverted nucleotide, preferably a 3'-3' linkage at the 3' end of the second strand;
(ii) one or more phosphorodithioate linkages;
(iii) the second strand nucleotide corresponding to position 11 or 13 of the first strand is not modified with a 2' O-methyl modification, preferably wherein one or both of these positions comprise a 2' fluoro modification;
(iv) the nucleic acid comprises at least 80% of all nucleotides having a 2'-O-methyl modification;
(v) the nucleic acid comprises no more than 20% of nucleotides which have 2' fluoro modifications.

Also provided by the present invention is a nucleic acid as disclosed herein, wherein the nucleotides at positions 2 and 14 from the 5' end of the first strand and the nucleotides at positions 7 and/or 9, or 7-9 from the 5' end of the second strand are modified with a 2' fluoro modification, and at least 90% of the remaining nucleotides are 2'-O methyl modified or comprise another naturally occurring 2' modification.

Specific preferred examples, for a blunt double stranded 19 base nucleic acid, with no overhang, are:

A nucleic acid as disclosed herein, wherein the nucleotides at positions 2 and 14 from the 5' end of the first strand are not modified with a 2' O-methyl modification, and the nucleotide at position 7 from the 5' end of the second strand is not modified with a 2' O-methyl modification.

A nucleic acid as disclosed herein, wherein the nucleotides at positions 2 and 14 from the 5' end of the first strand are not modified with a 2' O-methyl modification, and the nucleotide at position 9 from the 5' end of the second strand is not modified with a 2' O-methyl modification A nucleic acid as disclosed herein, wherein the nucleotides at positions 2 and 14 from the 5' end of the first strand are not modified with a 2' O-methyl modification, and the nucleotides at position 7 and 9 from the 5' end of the second strand are not modified with a 2'O-methyl modification.

A nucleic acid as disclosed herein, wherein the nucleotides at positions 2 and 14 from the 5' end of the first strand are not modified with a 2' O-methyl modification, and the nucleotides at positions 7-9 from the 5' end of the second strand are not modified with a 2'O-methyl modification.

A nucleic acid as disclosed herein, wherein the nucleotides at positions 2 and 14 from the 5' end of the first strand are not modified with a 2' O-methyl modification, and the nucleotides at positions 7 and/or 9, or 7-9 from the 5' end of the second strand are modified with a 2' fluoro modification.

A nucleic acid as disclosed herein, wherein the nucleotides at positions 2 and 14 from the 5' end of the first strand are modified with a 2' fluoro modification, and the nucleotides at positions 7 and/or 9, or 7-9 from the 5' end of the second strand are not modified with a 2'O-methyl modification.

A nucleic acid as disclosed herein, wherein the nucleotides at positions 2 and 14 from the 5' end of the first strand are modified with a 2' fluoro modification, and the nucleotides at positions 7 and/or 9, or 7-9 from the 5' end of the second strand are modified with a 2' fluoro modification.

A nucleic acid as disclosed herein wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

A nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2 O' methyl, other 2' sugar modifications, in particular a 2' H modification resulting in a DNA nucleotide.

A nucleic acid as disclosed herein comprising no more than 20%, such as no more than 15% such as more than 10%, of nucleotides which have 2' modifications that are not 2' O methyl modifications on the first and/or second strand, preferably as a percentage of the total nucleotides of both the first and second strands.

A nucleic acid as disclosed herein comprising no more than 20%, (such as no more than 15% or no more than 10%) of 2' fluoro modifications on the first and/or second strand, preferably as a percentage of the total nucleotides of both strands.

A nucleic acid as disclosed herein, wherein all nucleotides are modified with a 2' O-methyl modification except positions 2 and 14 from the 5' end of the first strand and the nucleotides at positions 7 and/or 9 from the 5' end of the second strand. Preferably the nucleotides that are not modified with 2' O-methyl are modified with fluoro at the 2' position.

A nucleic acid as disclosed herein, wherein all nucleotides are modified with a 2' O-methyl modification except positions 2 and 14 from the 5' end of the first strand and the nucleotides at positions 7-9 from the 5' end of the second strand. Preferably the nucleotides that are not modified with 2' O-methyl are modified with fluoro at the 2' position.

For a nucleic acid comprising a 20 base pair duplex region, the second strand preferably does not have a 2' O-methyl group at nucleotides 8 or 9 or 10 counting from the 5' end of the duplex corresponding to positions 13, 12, and 11 of the first strand respectively.

For a nucleic acid comprising a 21 base pair duplex region, the second strand preferably does not have a 2' O-methyl group at nucleotides 9 or 10 or 11 counting from the 5' end of the duplex corresponding to positions 13, 12, and 11 of the first strand respectively.

The present invention also relates to the unmodified sequences of all modified sequences disclosed herein.

The invention will now be described with reference to the following non-limiting figures and examples in which:

FIG. 7 shows siRNA conjugate sequences containing PS2 at different siRNA termini, together with GalNAc moieties without internal PS;

FIG. 8 shows serum stability of GalNAc siRNA conjugates with PS2 at different siRNA termini, together with GalNAc moieties without internal PS;

FIG. 16 shows schematic representations of various embodiments of nucleic acids conjugated with ligands via linkers.

EXAMPLES

Example 1

General Procedures siRNA modification: synthesis of siRNA with phosphorothioate (PS) or phosphorodithioate linkages (PS2).

Example compounds were synthesised according to methods described below and methods known to the person skilled in the art. Assembly of the oligonucleotide chain and linker building blocks was performed by solid phase synthesis applying phosphoramidite methodology.

Oligonucleotide synthesis, deprotection and purification followed standard procedures that are known in the art.

All oligonucleotides were synthesized on an AKTA oligopilot synthesizer using standard phosphoramidite chemistry. Commercially available solid support and 2'O-Methyl RNA phosphoramidites, 2'Fluoro, 2'Deoxy RNA phosphoramidites (all standard protection, ChemGenes, LinkTech) and thiophosphoarmidites (AM Biotech, GlenResearch) were used according to the manufacturers recommended procedures.

Synthesis of the phosphoramidite derivatives of ST41 (ST41-phos) as well as ST23 (ST23-phos) can be performed as described in WO2017/174657:

Ancillary reagents were purchased from EMP Biotech. Synthesis was performed using a 0.1 M solution of the phosphoramidite in dry acetonitrile and benzylthiotetrazole (BTT) was used as activator (0.3M in acetonitrile). Coupling time was 15 min. A Cap/OX/Cap or Cap/Thio/Cap cycle was applied (Cap: $Ac_2O$/NMI/Lutidine/Acetonitrile, Oxidizer: 0.1M $I_2$ in pyridine/$H_2O$). Phosphorothioates and phosphorodithioates were introduced using 50 mM EDITH in acetonitrile. All other reagents and solvents were commercially available and used in standard reagent quality.

DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

The single strands were cleaved off the CPG by 40% aq. methylamine treatment. The resulting crude oligonucleotide was purified by ion exchange chromatography (Resource Q, 6 mL, GE Healthcare) on a AKTA Pure HPLC System using a sodium chloride gradient. Product containing fractions were pooled, desalted on a size exclusion column (Zetadex, EMP Biotech) and lyophilised.

Synthesis of Oligonucleotides

Figure 10:
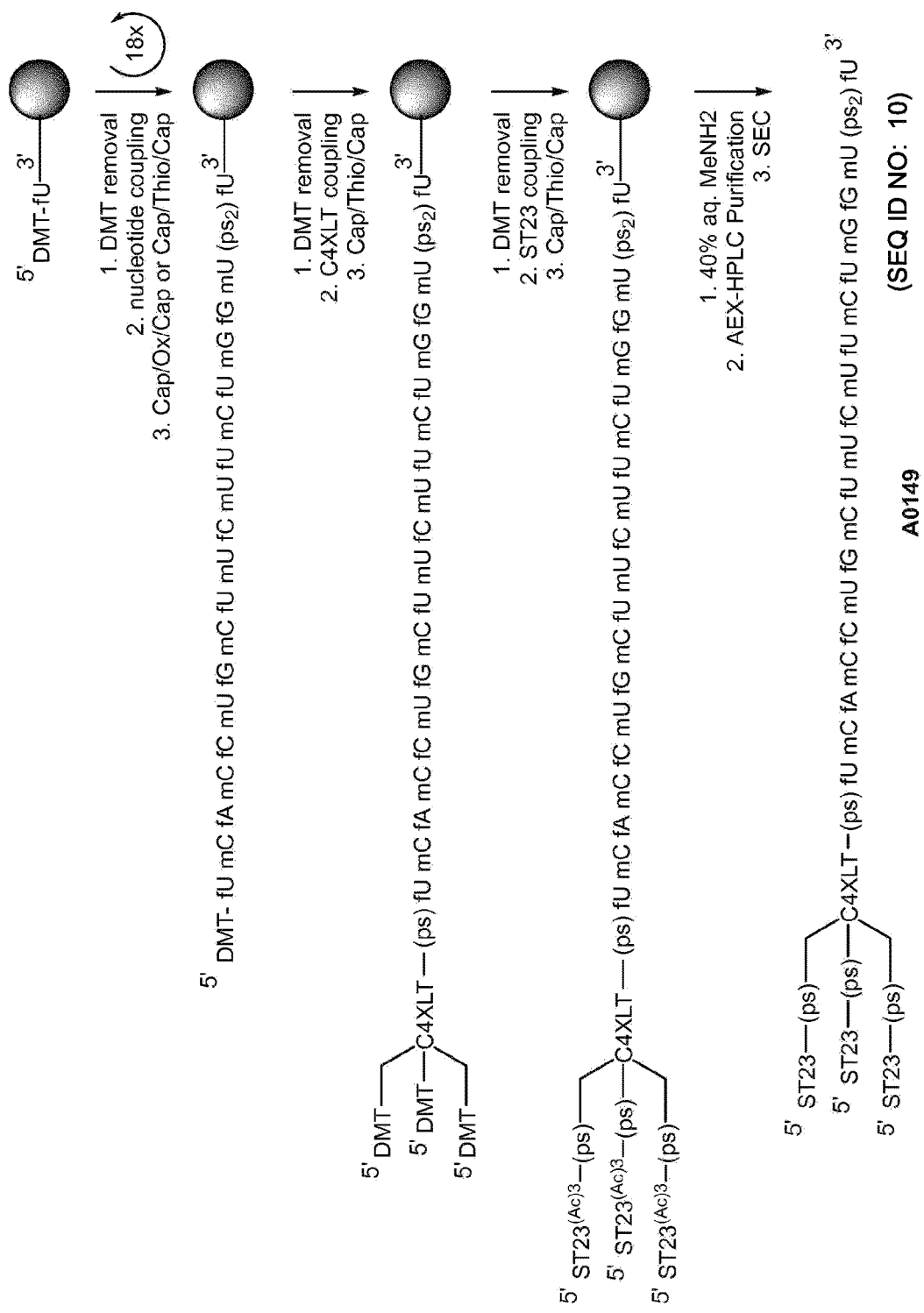
FIG. 10 shows a synthesis flow diagram of tree-like trivalent GalNAc conjugated oligonucleotides containing a phosphorodithioate linkage.
Figure 11:
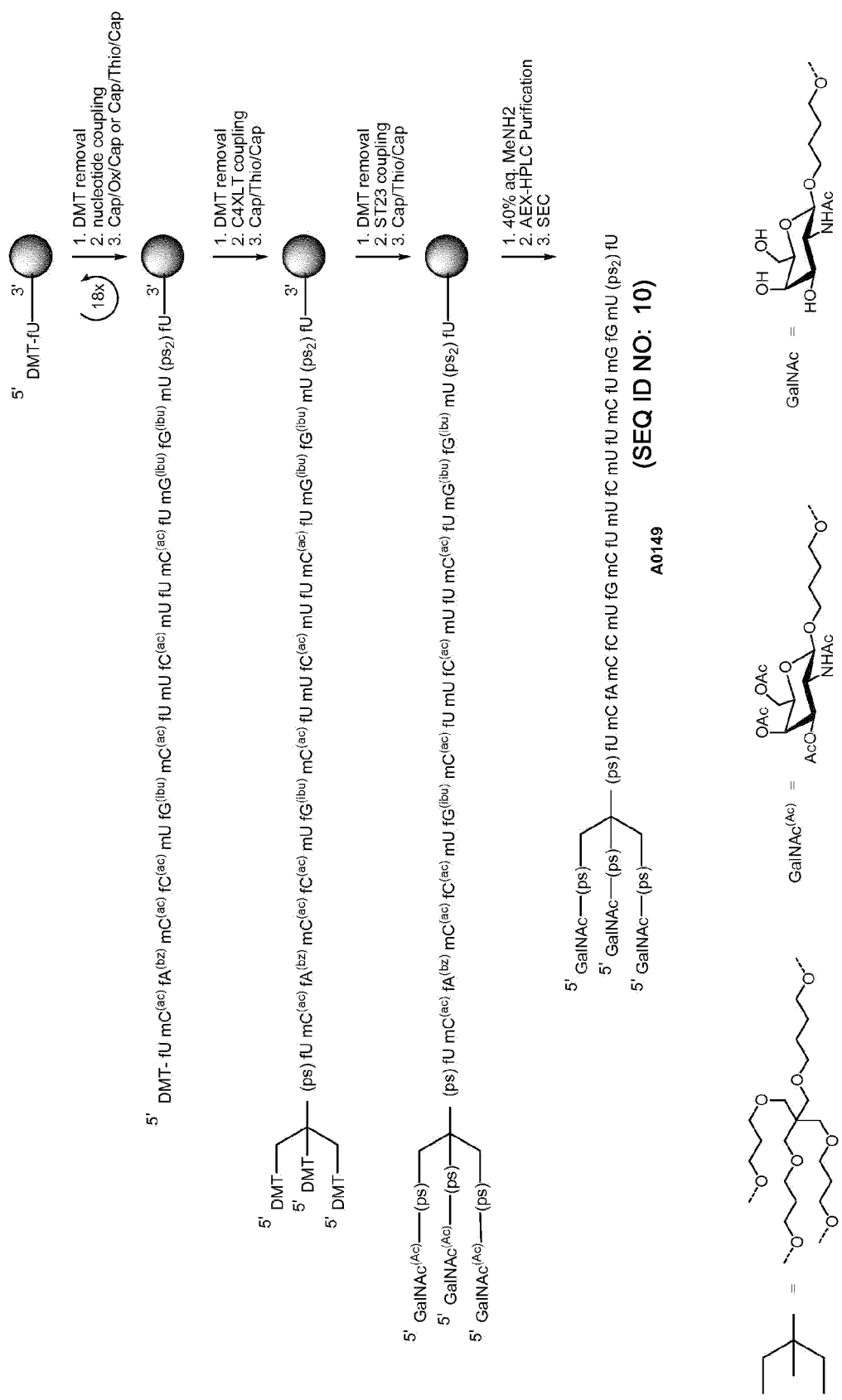
FIG. 11 shows a synthesis flow diagram of other tree-like trivalent GalNAc conjugated oligonucleotides containing a phosphorodithioate linkage.

All single stranded oligonucleotides were synthesised according to the reaction conditions described above and in FIG. 10.

All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products (non-modified, amino-modified precursors or GalNAc conjugated oligonucleotides) was proved by LC-MS analysis.

ST41-phos:

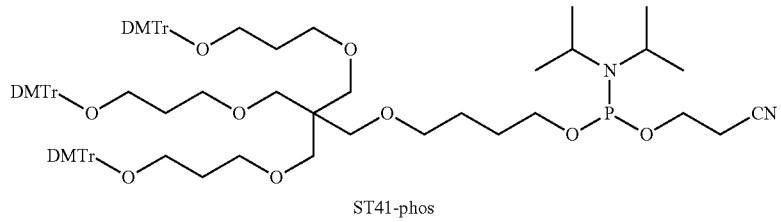

ST41-phos

ST23-phos:

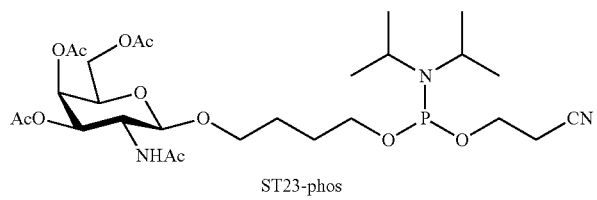

ST23-phos

TABLE 1

Single stranded oligonucleotides

| Product | Name | MW calc. | MW (ESI-) found | % FLP (AEX-HPLC) |
|---|---|---|---|---|
| A0126 | STS12009L4A | 6416.1 Da | 6415.8 Da | 92.8% |
| A0127 | STS12009L4B | 7642.0 Da | 7641.8 Da | 88.0% |
| A0134 | STS12009L4A | 6416.1 Da | 6415.8 Da | 91.3% |
| A0141 | STS12009L4B | 7642.0 Da | 7642.0 Da | 88.1% |
| A0148 | STS12009V15L4A | 6416.1 Da | 6416.1 Da | 84.1% |
| A0149 | STS12009V15L4B | 7642.0 Da | 7642.2 Da | 88.7% |
| A0150 | STS12009V16L4A | 6480.3 Da | 6480.3 Da | 82.8% |
| A0151 | STS12009V16L4B | 7674.0 Da | 7674.4 Da | 77.9% |
| A0153 | STS12009V18L50B | 7674.0 Da | 7674.1 Da | 78.5% |
| A0154 | STS12009V21L4A | 6384.1 Da | 6383.5 Da | 86.7% |
| A0155 | STS12009V19L50B | 7579.0 Da | 7577.8 Da | 86.8% |
| A0156 | STS12009V20L50B | 7610.0 Da | 7609.9 Da | 85.6% |
| A0164 | STS12009V21L4B | 7626.0 Da | 7625.8 Da | 84.3% |
| A0167 | STS12009V17L50B | 7610.0 Da | 7610.0 Da | 84.7% |
| A0245 | STS12009V36L4A | 6416.0 Da | 6415.9 Da | 91.5% |
| A0246 | STS12009V37L4A | 6416.0 Da | 6415.7 Da | 95.2% |
| A0347 | STS12009V55L50B | 7578.0 Da | 7577.7 Da | 94.9% |
| A0348 | STS12009V56L50A | 6352.1 Da | 6351.5 Da | 95.1% |
| A0349 | STS12009V57L50A | 6384.1 Da | 6383.9 Da | 88.7% |

TABLE 2

Nucleic acid conjugates

| Product | Starting Materials | | Name | % double strand |
|---|---|---|---|---|
| X0027 | A0126 | A0127 | STS12009L4 | 93.4% |
| X0063 | A0148 | A0149 | STS12009V15L4 | >99% |
| X0064 | A0150 | A0151 | STS12009V16L4 | 97.9% |
| X0065 | A0154 | A0164 | STS12009V21L4 | >99% |
| X0067 | A0148 | A0167 | STS12009V17L50 | >99% |
| X0068 | A0150 | A0153 | STS12009V18L50 | 99.6% |
| X0069 | A0154 | A0155 | STS12009V19L50 | >99% |
| X0070 | A0134 | A0156 | STS12009V20L50 | 99.7% |
| X0118 | A0134 | A0149 | STS12009V34L4 | 94.3% |
| X0120 | A0245 | A0141 | STS12009V36L4 | 94.6% |
| X0121 | A0246 | A0141 | STS12009V37L4 | 92.7% |
| X0135 | A0134 | A0167 | STS12009V40L50 | 95.8% |
| X0214 | A0245 | A0167 | STS12009V54L50 | 95.6% |
| X0215 | A0245 | A0347 | STS12009V55L50 | 93.7% |
| X0216 | A0348 | A0347 | STS12009V56L50 | >99% |
| X0217 | A0349 | A0347 | STS12009V57L50 | 97.3% |

Double Strand Formation

Individual single strands were dissolved in a concentration of 60 OD/mL in H₂O. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Example 2

Figure 1:
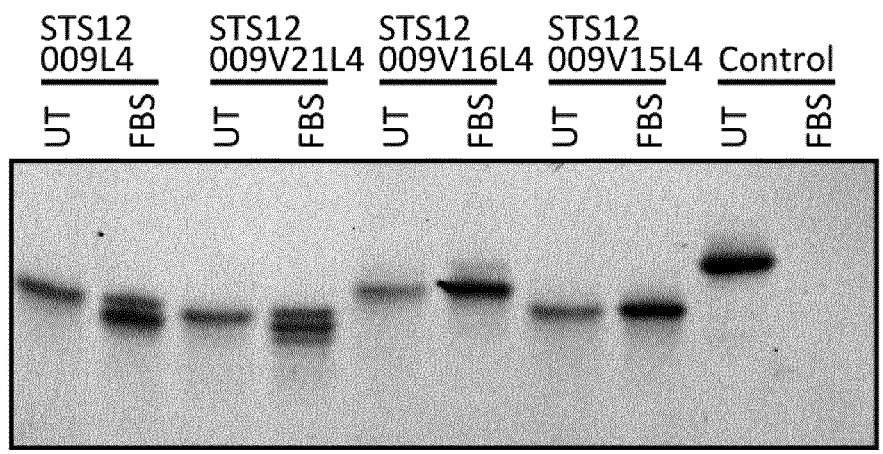
FIG. 1 shows results of a serum stability assay of GalNAc-siRNA conjugates containing two phosphorothioates (PS), one PS, two phosphorodithioates (PS2), and one PS2 at terminal positions.

Serum stability assay of GalNAc-siRNA conjugates containing two PS (STS12009L4), one PS (STS12009V21L4), two PS2 (STS12009V16L4) and one PS2 (STS12009V15L4) at terminal positions. GalNAc was conjugated to the 5'-end of the second strand and is internally stabilized by four PS. Phosphorothioates and phosphorodithioates, respectively were placed at the 5'-end of the first strand, 3'-end of the first strand and 3'-end of the second strand. 5 µM GalNAc-siRNA conjugates were incubated with 50% FBS for 3 d at 37° C. RNA was extracted and analysed on 20% TBE polyacrylamide gels and results are shown in FIG. 1. "UT" indicates untreated samples, "FBS" indicates FBS treatment. "Control" indicates a less stabilized GalNAc-siRNA conjugate of different sequence. The sequences are set out in Table 3.

TABLE 3

GalNAc-siRNA conjugates containing two PS, one PS, two PS2 and one PS2 at all non-conjugated ends.

| duplex ID | sequence and chemistry (top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA |
| | [ST23(ps)]3 ST41(ps)fUmCfAmCfCmUfGmCfUmUfCmUfUmCfUmGfG(ps)mU(ps)fU |
| STS12009V21L4 | mA(ps)fAmCfCmAfGmAfAmGfAmAfGmCfAmGfGmUfG(ps)mA |
| | [ST23(ps)]3 ST41(ps)fUmCfAmCfCmUfGmCfUmUfCmUfUmCfUmGfGmU(ps)fU |
| STS12009V16L4 | mA(ps2)fA(ps2)mCfCmAfGmAfAmGfAmAfGmCfAmGfGmU(ps2)fG(ps2)mA |
| | [ST23(ps)]3 ST41(ps)fUmCfAmCfCmUfGmCfUmUfCmUfUmCfUmGfG(ps2)mU(ps2)fU |
| STS12009V15L4 | mA(ps2)fAmCfCmAfGmAfAmGfAmAfGmCfAmGfGmUfG(ps2)mA |
| | [ST23(ps)]3 ST41(ps)fUmCfAmCfCmUfGmCfUmUfCmUfUmCfUmGfGmU(ps2)fU | mA, mU, mC, mG-2'-OMe RNA fA, fU, fC, fG - 2'-F RNA (ps) - phosphorothioate (ps2) - phosphorodithioate

Example 3

Figure 2:
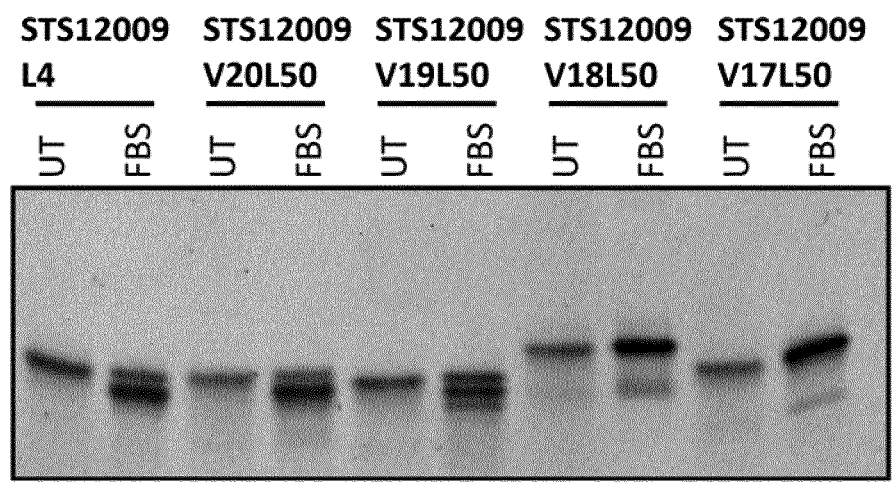
FIG. 2 shows results of a serum stability assay of GalNAc-siRNA conjugates containing two PS, one PS, two PS2 and one PS2 at terminal positions with no PS in the GalNAc moiety.

Serum stability assay of GalNAc-siRNA conjugates containing two PS (STS12009L4, STS12009V20L50), one PS (STS12009V19L50), two PS2 (STS12009V18L50) and one PS2 (STS12009V17L50) at terminal positions. In the variants –V20, –V19, –V18 and –V17, GalNAc was conjugated to the 5'-end of the second strand and does not contain any PS. Phosphorothioates and phosphorodithioates, respectively, were placed at the 5'-end of the first strand, 3'-end of the first strand, 5'-end of the second strand and 3'-end of the second strand. STS12009L4 contains each two terminal PS at 5'-end of the first strand, 3'-end of the first strand and 3'-end of the second strand, whereas GalNAc is attached to the second strand 5'-end and stabilized by four internal PS. 5 µM GalNAc-siRNA conjugates were incubated with 50% FBS for 3 d at 37° C. RNA was extracted and analysed on 20% TBE polyacrylamide gels. Results are shown in FIG. 2. "UT" indicates untreated samples, "FBS" indicates FBS treatment.

Sequences are set out in Table 4.

TABLE 4

GalNAc-siRNA conjugates containing two PS, one PS, two PS2 and one PS2 at terminal positions.

| duplex ID | sequence and chemistry (top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>[ST23(ps)]3 ST41(ps)fUmCfAmCfCmUfGmCfUmUfCmUfUmCfUmGfG(ps)mU(ps)fU |
| STS12009V20L50 | mA(ps)fA(ps)mCfCmAfGmAfAmGfAmAfGmCfAmGfGmU(ps)fG(ps)mA<br>[ST23]3 ST41 fU(ps)mC(ps)fAmCfCmUfGmCfUmUfCmUfUmCfUmGfG(ps)mU(ps)fU |
| STS12009V19L50 | mA(ps)fAmCfCmAfGmAfAmGfAmAfGmCfAmGfGmUfG(ps)mA<br>[ST23]3 ST41 fU(ps)mCfAmCfCmUfGmCfUmUfCmUfUmCfUmGfGmU(ps)fU |
| STS12009V18L50 | mA(ps2)fA(ps2)mCfCmAfGmAfAmGfAmAfGmCfAmGfGmU(ps2)fG(ps2)mA<br>[ST23]3 ST41 fU(ps2)mC(ps2)fAmCfCmUfGmCfUmUfCmUfUmCfUmGfG(ps2)mU(ps2)fU |
| STS12009V17L50 | mA(ps2)fAmCfCmAfGmAfAmGfAmAfGmCfAmGfGmUfG(ps2)mA<br>[ST23]3 ST41 fU(ps2)mCfAmCfCmUfGmCfUmUfCmUfUmCfUmGfGmU(ps2)fU | mA, mU, mC, mG – 2'-OMe RNA
fA, fU, fC, fG – 2'-F RNA
(ps) – phosphorothioate
(ps2) – phosphorodithioate

Example 4

Figure 3:
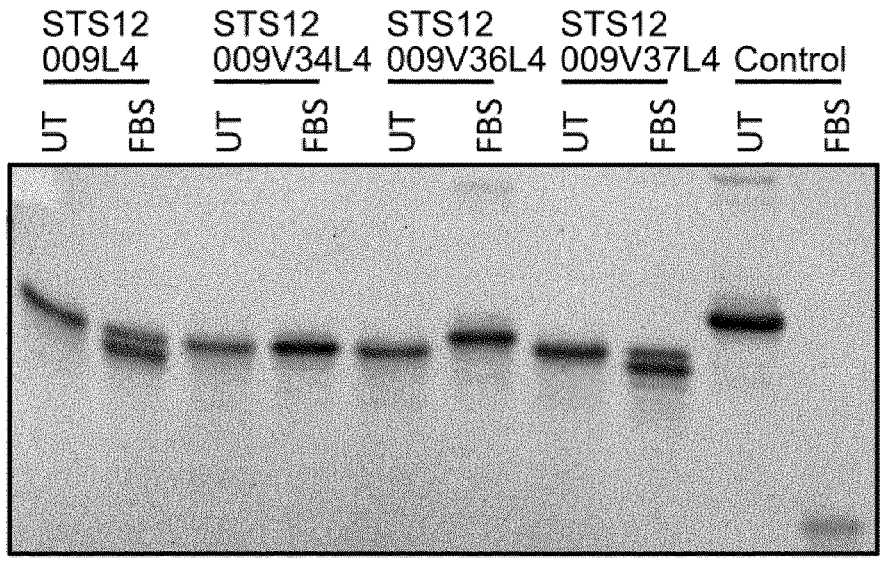
FIG. 3 shows results of a serum stability assay of GalNAc-siRNA conjugates containing one PS2 at individual ends.

Serum stability assay of GalNAc-siRNA conjugates containing one PS2 at individual ends. GalNAc was conjugated to the 5'-end of the second strand and is internally stabilized by four PS. Phosphorodithioate modifications were placed at the 5'-end of the first strand (STS12009V37L4), 3'-end of the first strand (STS12009V36L4) and 3'-end of the second strand (STS12009V34L4). All other, non-conjugated ends were stabilised by each two terminal PS. STS12009L4 contains two terminal PS at the 5'-end of the first strand, 3'-end of the first strand and 3'-end of the second strand. 5 µM GalNAc-siRNA conjugates were incubated with 50% FBS for 3 d at 37° C. RNA was extracted and analysed on 20% TBE polyacrylamide gels. Results are shown in FIG. 3. "UT" indicates untreated samples, "FBS" indicates FBS treatment. "Control" indicates a less stabilized GalNAc-siRNA conjugate of different sequence.

Sequences are shown in Table 5.

TABLE 5

GalNAc-siRNA conjugates containing one PS2 at individual ends.

| duplex ID | sequence and chemistry (top: first strand, bottom: second strand, both 5-3') |
|---|---|
| STS12009L4 | mA(ps)fA(ps)mCfCmAfGmAfAmGfAmAfGmCfAmGfGmU(ps)fG(ps)mA<br>[ST23(ps)]3 ST41(ps)fUmCfAmCfCmUfGmCfUmUfCmUfUmCfUmGfG(ps)mU(ps)fU |
| S1S12009V34L4 | mA(ps)fA(ps)mCfCmAfGmAfAmGfAmAfGmCfAmGfGmU(ps)fG(ps)mA<br>[ST23(ps)]3 ST41(ps)fUmCfAmCfCmUfGmCfUmUfCmUfUmCfUmGfGmU(ps2)fU |

TABLE 5-continued

GalNAc-siRNA conjugates containing one PS2 at individual ends.

| duplex ID | sequence and chemistry (top: first strand, bottom: second strand, both 5-3') |
|---|---|
| S1S12009V36L4 | mA(ps)fA(ps)mCfCmAfGmAfAmGfAmAfGmCfAmGfGmUfG(ps2)mA<br>[ST23 (ps)]3 ST41(ps)fUmCfAmCfCmUfGmCfUmUfCmUfUmCfUmGfG(ps)mU(ps)fU |
| S1S12009V37L4 | mA(ps2)fAmCfCmAfGmAfAmGfAmAfGmCfAmGfGmU(ps)fG(ps)mA<br>[ST23(ps)]3 ST41(ps)fUmCfAmCfCmUfGmCfUmUfCmUfUmCfUmGfG(ps)mU(ps)fU | mA, mU, mC, mG - 2'-OMe RNA
fA, fU, fC, fG - 2'-F RNA
(ps) - phosphorothioate
(ps2) - phosphorodithioate

Example 5

Figure 4:
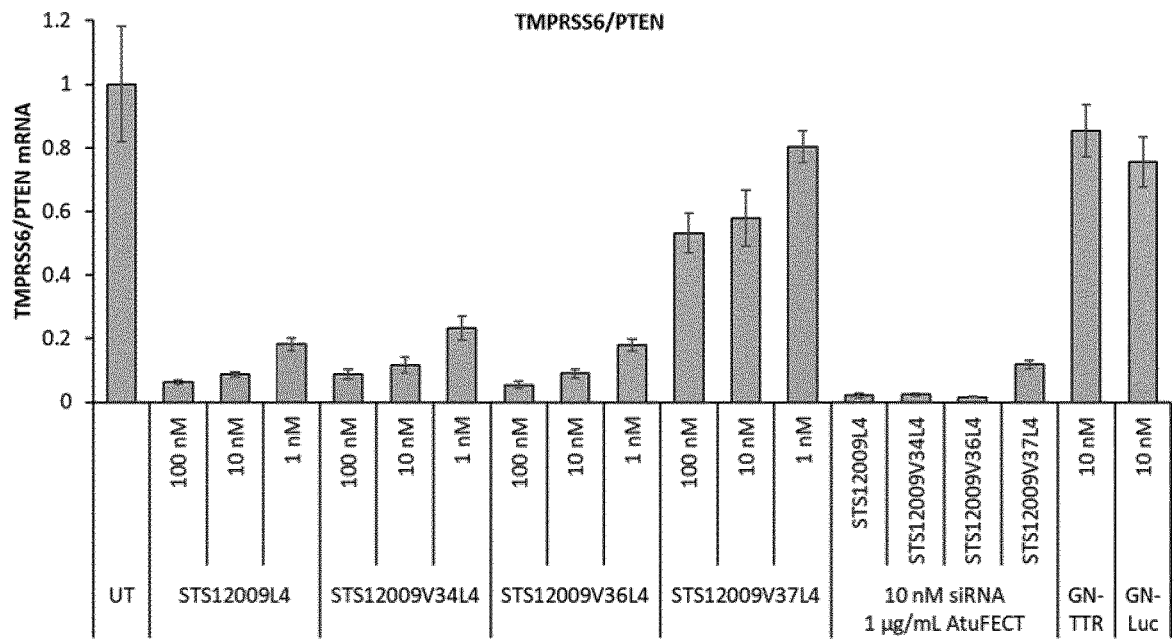
FIG. 4 shows the activity of GalNAc-siRNA conjugates containing one PS2 at individual ends.

Activity of GalNAc-siRNA conjugates containing one PS2 at individual ends. GalNAc was conjugated to the 5'-end of the second strand and is internally stabilized by four PS. Phosphorodithioate modifications were placed at the 5'-end of the first strand (STS12009V37L4), 3'-end of the first strand (STS12009V36L4) and 3'-end of the second strand (STS12009V34L4). All other, non-conjugated ends were stabilised by each two terminal PS. STS12009L4 contains each two terminal PS at 5'-end of the first strand, 3'-end of the first strand and 3'-end of the second strand. The experiment was conducted in mouse primary hepatocytes. Cells were seeded at a density of 250,000 cells per 6-well and treated with 100 nM, 10 nM and 1 nM GalNAc-siRNA. Transfections with 10 nM GalNAc-siRNA and 1 µg/ml Atufect served as control. Cells were lysed after 24 h, total RNA was extracted and Tmprss6 and Pten mRNA levels were determined by Taqman qRT-PCR. Results are shown in FIG. 4. Each bar represents mean±SD of three technical replicates. Sequences are as set out in Table 5.

Example 6

Figure 5:
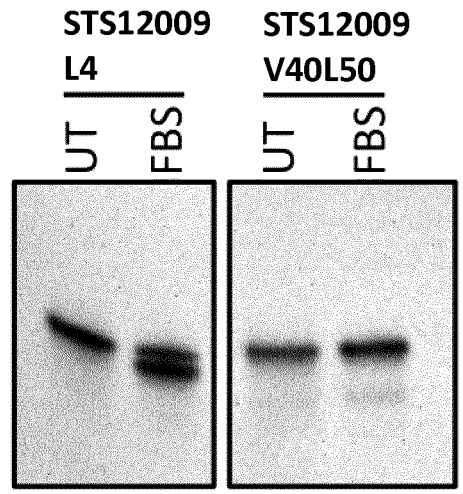
FIG. 5 shows results of serum stability assay of a GalNAc-siRNA conjugate containing each one PS2 at the second strand 5'-end and at the second strand 3'-end with no PS in the linker moiety.

Serum stability assay of a GalNAc-siRNA conjugate (STS12009V40L50) containing each one PS2 at the second strand 5'-end and at the second strand 3'-end. GalNAc was conjugated to the 5'-end of the second strand and is not stabilized by any internal PS. STS12009L4 contains each two terminal PS at 5'-end of the first strand, 3'-end of the first strand and 3'-end of the second strand ends, GalNAc is attached to the second strand 5'-end and stabilized by four internal PS. 5 µM GalNAc-siRNA conjugates were incubated with 50% FBS for 3 d at 37° C. RNA was extracted and analysed on 20% TBE polyacrylamide gels. Results are shown in FIG. 5. "UT" indicates untreated samples, "FBS" indicates FBS treatment.

Sequences are shown in Table 6

TABLE 6

GalNAc-siRNA conjugate (STS12009V40L50) containing each one PS2 at the second strand 5'-end and at the second strand 3'-end, in combination with a no PS-containing GalNAc linker.

| duplex ID | sequence and chemistry (top: first strand, bottom: second strand, both 5'-3') |
|---|---|
| STS12009L4 | mA(ps)fA(ps)mCfCmAfGmAfAmGfAmAfGmCfAmGfGmU(ps)fG(ps)mA<br>[ST23(ps)]3 ST41(ps)fUmCfAmCfCmUfGmCfUmUfCmUfUmCfUmGfG(ps)mU(ps)fU |
| STS12009V40L50 | mA(ps)fA(ps)mCfCmAfGmAfAmGfAmAfGmCfAmGfGmU(ps)fG(ps)mA<br>[ST23]3 ST41 fU(ps2)mCfAmCfCmUfGmCfUmUfCmUfUmCfUmGfGmU(ps2)fU | mA, mU, mC, mG - 2'-OMe RNA
fA, fU, fC, fG - 2'-F RNA
(ps) - phosphorothioate
(ps2) - phosphorodithioate

Example 7

Figure 6:
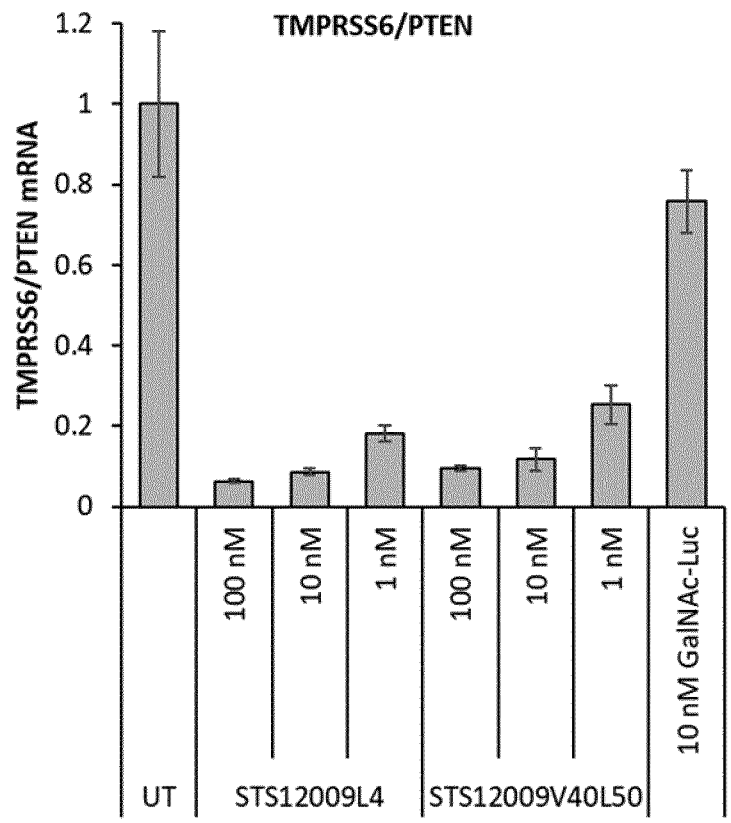
FIG. 6 shows the activity of a GalNAc-siRNA conjugate containing each one PS2 at the second strand 5'-end and at the second strand 3'-end with no PS in the GalNAc moiety.

Activity of a GalNAc-siRNA conjugate (STS12009V40L50) containing each one PS2 at the second strand 5'-end and at the second strand 3'-end. GalNAc was conjugated to the 5'-end of the second strand and is not stabilized by any internal PS. STS12009L4 contains each two terminal PS at 5'-end of the first strand, 3'-end of the first strand and 3'-end of the second strand. Here, GalNAc is attached to the 5'-end of the second strand and stabilized by four internal PS. The experiment was conducted in mouse primary hepatocytes. Cells were seeded at a density of 250,000 cells per 6-well and treated with 100 nM, 10 nM and 1 nM GalNAc-siRNA. A GalNAc conjugate of an siRNA against Luciferase ("GalNAc-Luc") served as control. Cells were lysed after 24 h, total RNA was extracted and Tmprss6 and Pten mRNA levels were determined by Taqman qRT-PCR. Results are shown in FIG. 6. Each bar represents mean±SD of three technical replicates. Sequences are as set out in Table 6.

Example 8

Serum stability assay of GalNAc-siRNA conjugates with phosphorothioates, phosphorodithioates and phosphodiesters in terminal positions and in the GalNAc moiety. GalNAc was conjugated to the 5'-end of the sense strand and is internally stabilized by four PS (STS12009L4) or not, then phosphodiester linkages are used instead (STS12009V54L50-V57L50). Phosphorodithioate modifications were placed at all terminal positions of the duplex except of the first strand 5'-end (-V54L50), at the 3'-ends only (-V55L50, -V57L50) or at the 3'-end of the second strand only (-V56L50). In certain designs, phosphodiesters were used in terminal positions of the siRNA duplex (-V56L50, -V57L50).

5 μM GalNAc-siRNA conjugates were incubated with 50% FBS for 3 d at 37° C. RNA was extracted and analysed on 20% TBE polyacrylamide gels. "UT" indicates untreated samples, "FBS" indicates FBS treatment. "Control" indicates a less stabilized GalNAc-siRNA conjugate of different sequence.

Sequences are shown in FIG. 7 and results in FIG. 8.

Example 9

GalNAc conjugates of an siRNA targeting Tmprss6 containing different end stabilization chemistries (phosphorothioate, phosphorodithioate, phosphodiester) were tested by receptor-mediated uptake in primary mouse hepatocytes. GalNAc was conjugated to the 5'-end of the second strand and is internally stabilized by four PS (STS12009L4) or not, then phosphodiester linkages are used instead (STS12009V54L50-V57L50). Phosphorodithioate modifications were placed at all terminal positions of the duplex except of the first strand 5'-end (-V54L50), at the 3'-ends only (-V55L50, -V57L50) or at the 3'-end of the second strand only (-V56L50). In certain designs, phosphodiesters were used in terminal positions of the siRNA duplex (-V56L50, -V57L50).

The experiment was conducted in mouse primary hepatocytes. Cells were seeded at a density of 20,000 cells per 96-well and treated with 125 nM to 0.2 nM GalNAc-siRNA. Cells were lysed after 24 h, total RNA was extracted and Tmprss6 and Pten mRNA levels were determined by Taqman qRT-PCR. Each bar represents mean±SD of three technical replicates.

Figure 9:
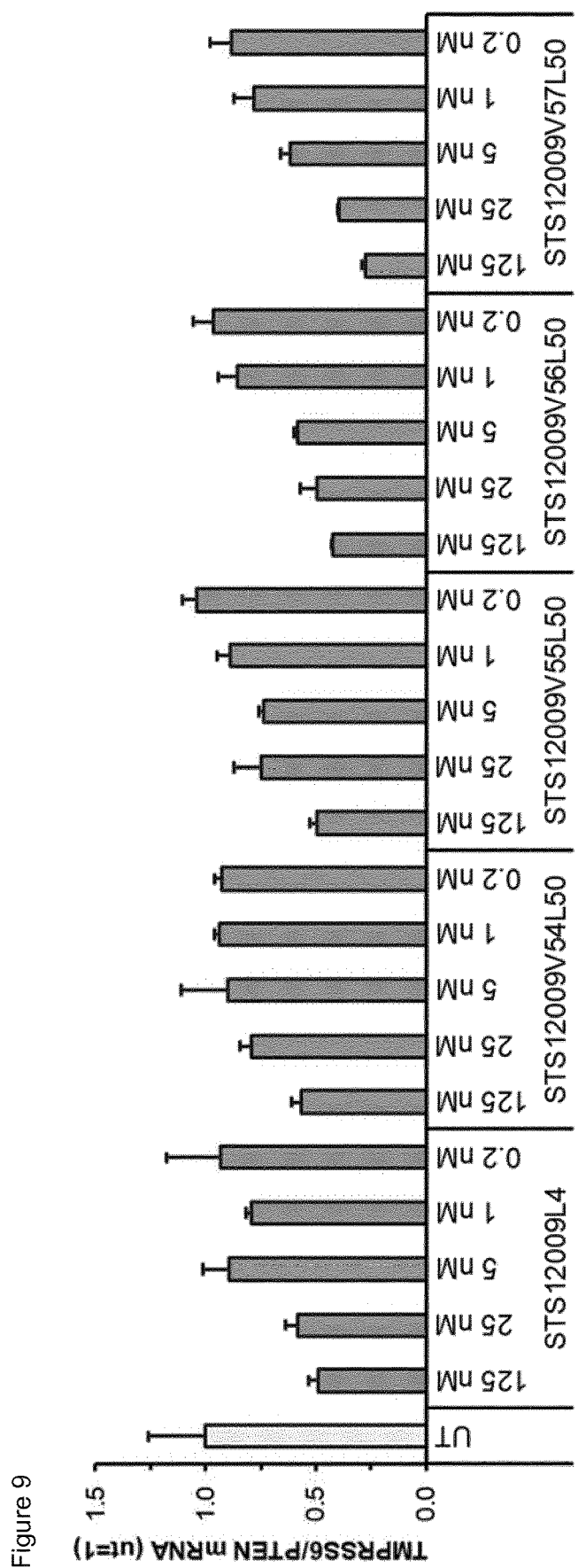
FIG. 9 shows in vitro activity of GalNAc siRNA conjugates with PS2 at different siRNA termini, together with GalNAc moieties without internal PS.

Sequences are shown in FIG. 7 and results in FIG. 9.

Example 10

GalNAc conjugates targeting TMPRSS6 and containing phosphorodithioate linkages at one or more termini effectively reduce serum iron and TMPRSS6 mRNA levels in vivo.

STS12009L4 and STS12009V34L4 contain a GalNAc moiety which is internally stabilised by four phosphorothioate linkages. STS12009V54L50 contains a GalNAc moiety without internal phosphorothioates. In STS12009L4 all non-conjugated termini are stabilized by each two phosphorothioates. In STS12009V34L4, one phosphorodithioate linkage is present at the 3' end of the second strand, whereas all other, non-conjugated ends are stabilized with each two phosphorothioates. In STS12009V54L50, each one phosphorodithioate is present at the 3' end of the first strand, at the 5' end of the second strand and at the 3' end of the second strand. The 5' end of the first strand is stabilized by two phosphorothioates. These siRNA conjugates show dose-dependent reduction of TMPRSS6 mRNA levels and serum iron levels. The phosphorodithioate-containing conjugates STS12009V34L4 and STS12009V54L50 are as active as the reference compound which does not contain phosphorodithioates. Hence, the number of phosphorothioates can be reduced from ten (STS12009L4) to eight (STS12009V34L4) and further to two (STS12009V54L50) without compromising activity. STS12009V57L50 contains each one phosphorodithioate linkage at the 3' end of the first strand and at the 3' end of the second strand. The 5' ends of both strands contain phosphodiesters and the linker moiety does not contain internal phosphodiesters. In vivo activity of this siRNA conjugate is strongly reduced.

C57BL/6 male mice (n=6) were subcutaneously treated with 3 mg/kg, 1 mg/kg and 0.3 mg/kg GalNAc conjugate. Liver sections were prepared seven days after treatment, total RNA was extracted from the tissue and TMPRSS6 and PTEN mRNA levels were determined by TaqMan qRT-PCR. In addition, serum iron levels were analysed.

Figure 12:
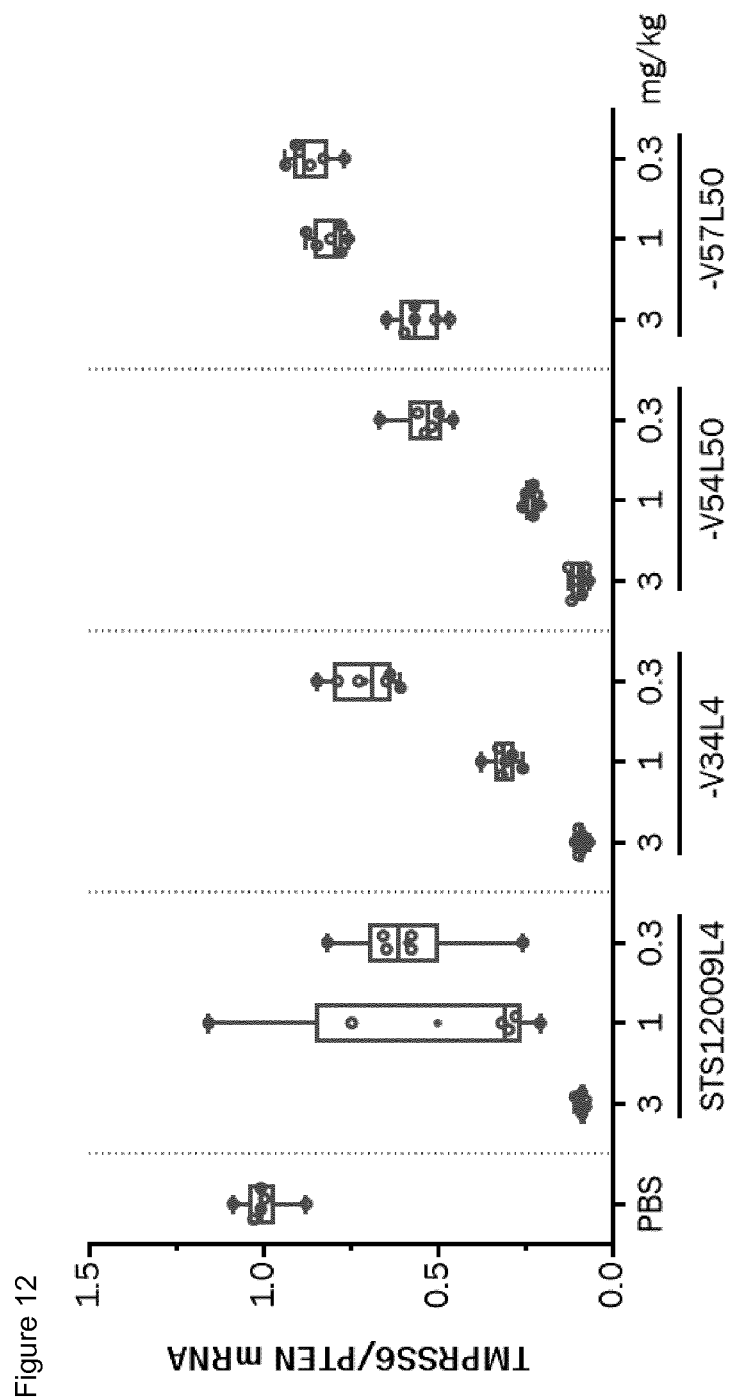
FIG. 12 shows in vivo mRNA reducing activity of Gal-NAc siRNA conjugates with PS2 at different siRNA termini.
Figure 13:
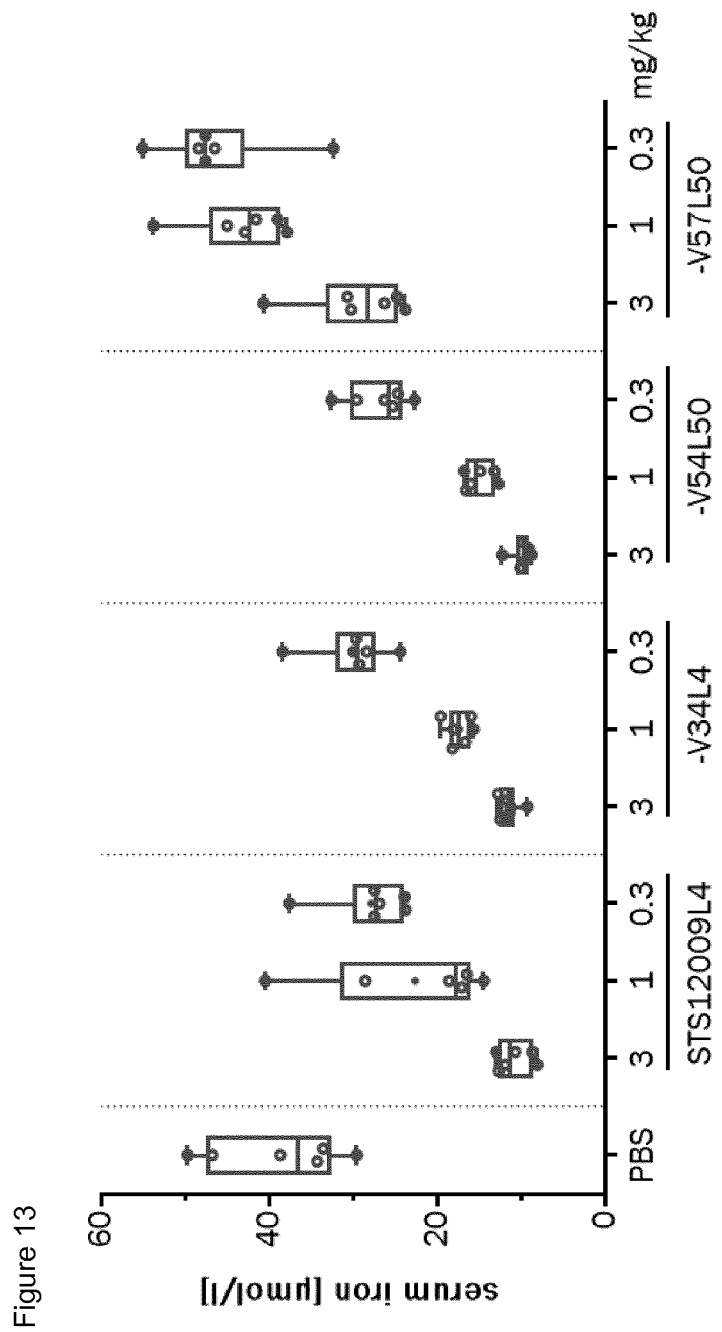
FIG. 13 shows in vivo serum iron reducing activity of GalNAc siRNA conjugates with PS2 at different siRNA termini.

Sequences are shown in table 7 below and results in FIGS. 12 and 13.

Example 11

GalNAc conjugates with terminal phosphorodithioates are active in vitro.

GalNAc conjugates of an siRNA targeting TMPRSS6 and containing different end stabilization chemistries (phosphorothioate, phosphorodithioate, phosphodiester) were tested by receptor-mediated uptake in primary mouse hepatocytes. A triantennary GalNAc moiety was conjugated to the 5' end of the second strand and is internally stabilized by four PS in X0027, X0346, X0347. In this case, no phosphorothioate is present at the 5' end of the second strand. In X0214 and X0345, the GalNAc moiety does not contain phosphorothioates and phosphorodithioate is present at 5' end of the second strand. In X0214, X0345, X0346 and X0347, phosphorodithioate modifications are present at the 3' ends of first and second strand. The first strand 5' end is either stabilized by two phosphorothioates (X0214, X0346) or contains phosphodiester linkages (X0345, X0347). All described conjugates reduce target mRNA levels in vitro. X0214 and X0346 show reduced activity compared to X0345 and X0347. This suggests that phosphorothioates at the 5' end of the first strand negatively affect siRNA activity in vitro.

The experiment was conducted in mouse primary hepatocytes. Cells were seeded at a density of 20,000 cells per 96-well and treated with 0.1 nM, 1 nM, 10 nM and 100 nM GalNAc-siRNA. Cells were lysed after 24 h, total RNA was extracted and TMPRSS6 and PTEN mRNA levels were determined by Taqman qRT-PCR. Each bar represents mean±SD of three technical replicates.

Figure 14:
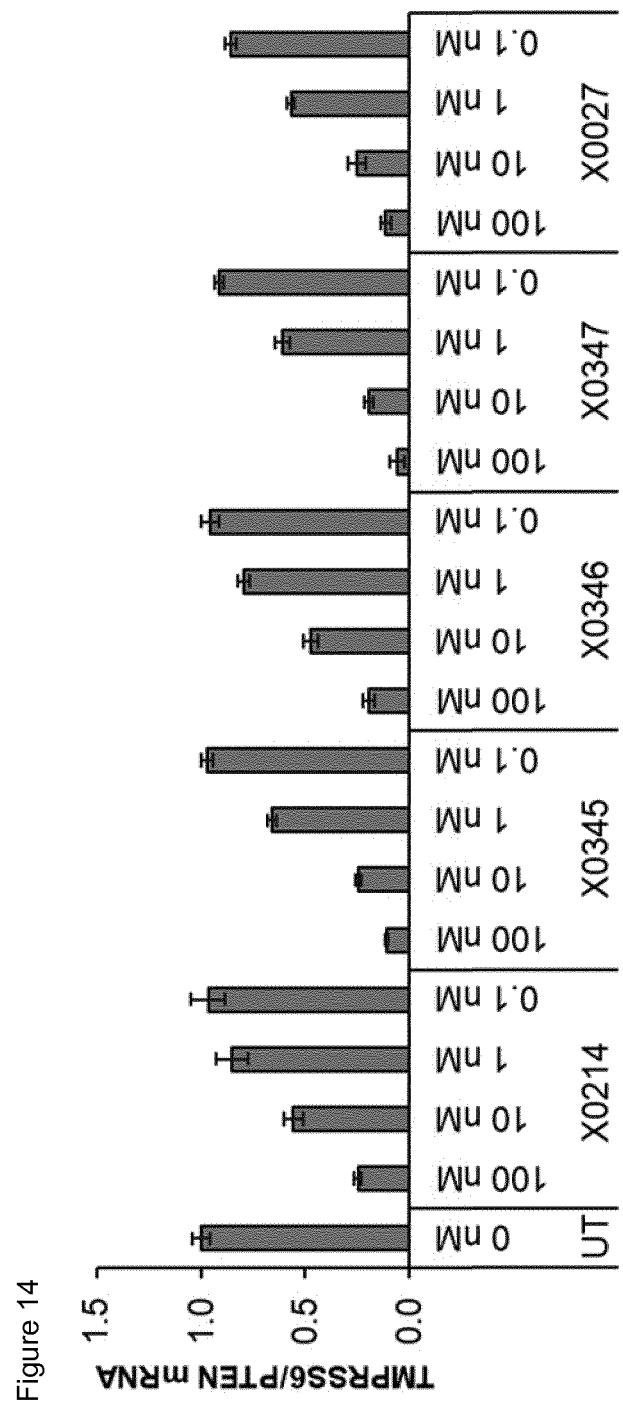
FIG. 14 shows in vitro activity of GalNAc siRNA conjugates with PS2 and PS at different siRNA termini, together with GalNAc moieties with or without internal PS.

Sequences are shown in table 7 below and data in FIG. 14.

Example 12 siRNA conjugates with each one serinol-linked GalNAc at the 5' and 3' end of the second strand and with terminal phosphorodithioates are active in vitro.

GalNAc-conjugated siRNAs targeting TMPRSS6 were tested by receptor-mediated uptake in primary mouse hepatocytes. In both X0454 and X0456, each one serinol-linked GalNAc moiety was conjugated to the 5' and 3' ends of the second strand. Both conjugates contain (E)-vinylphosphonate at the 5' end of the first strand. No phosphorothioates are present at the 5' end of the first strand. In X0454, each two phosphorothioates are present at the 3' end of the first strand and at the 5' and 3' ends of the second strand. Each GalNAc moiety contains one phosphorothioate. In X0456, each one phosphorodithioate is present between the last two nucleotides at the 3' end of the first strand and at the 5' and 3' ends of the second strand. No undefined stereogenic centre is present in X0456. A GalNAc-conjugated siRNA targeting Luciferase was used as non-targeting control at 125 nM and does not reduce target mRNA levels. The conjugates targeting TMPRSS6 both reduce target mRNA levels in vitro.

Hence, phosphorodithioates can be applied for end stabilisation of siRNAs with single GalNac moieties at both ends of the second strand.

The experiment was conducted in mouse primary hepatocytes. Cells were seeded at a density of 20,000 cells per 96-well and treated with 0.2 nM, 1 nM, 5 nM, 25 nM and 125 nM GalNAc-siRNA. Cells were lysed after 24 h, total RNA was extracted and TMPRSS6 and ACTB mRNA levels were determined by Taqman qRT-PCR. Each bar represents mean±SD of three technical replicates.

Figure 15:
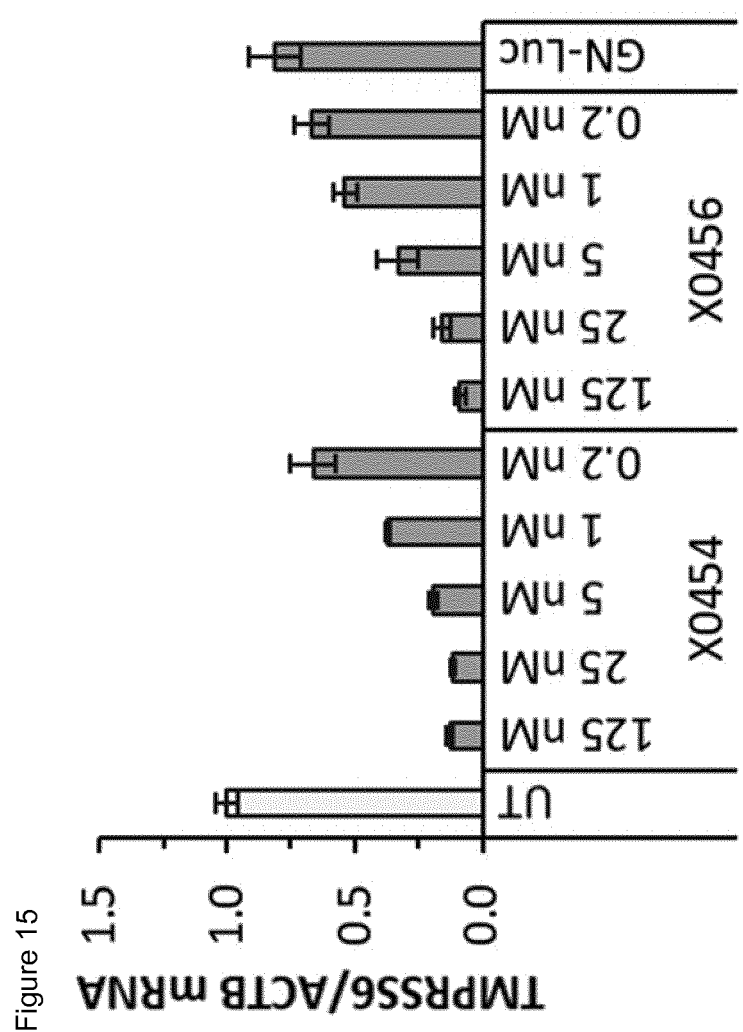
FIG. 15 shows the activity of siRNA conjugates with each one serinol-linked GalNAc at the 5' and 3' end of the second strand and with terminal phosphorodithioates.

Sequences are shown in table 7 below and data in FIG. 15.

STATEMENTS OF INVENTION

1. A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first and/or second strand includes a phosphorodithioate linkage between at least two nucleotides.

2. A nucleic acid according to statement 1, wherein the first strand does not comprise a phosphorodithioate linkage between any of the two, three or four terminal nucleotides at the 5' end.

3. A nucleic acid according to statement 1 or 2, comprising a phosphorodithioate linkage between each of the two, three or four terminal nucleotides at the 3' end of the first strand.

4. A nucleic acid according to statements 1-3, comprising a phosphorodithioate linkage between each of the two, three or four terminal nucleotides at the 3' end of the second strand.

5. A nucleic acid according to any one of statements 1 to 4 comprising a phosphorothioate linkage between each of the two, three or four terminal nucleotides at the 5' end of the second strand or a phosphorodithioate linkage between each of the two, three or four terminal nucleotides at the 5' end of the second strand.

6. A nucleic acid according to any one of statements 1 to 5, wherein the nucleic acid comprises a phosphorothioate linkage between each of the three terminal 3' nucleotides and/or between each of the three terminal 5' nucleotides on the first strand, and/or between each of the three 3' terminal nucleotides and/or between each of the three 5' nucleotides of the second strand when there is no phosphorodithioate linkage present at that end.

7. A nucleic acid according to any of statements 1 to 6, wherein the first strand and the second strand are separate strands.

8. A nucleic acid according to any of statements 1 to 6, comprising a single strand that comprises the first strand and the second strand.

9. A nucleic acid according to any of statements 1 to 8, wherein said first strand and/or said second strand are each from 17-35 nucleotides in length.

10. A nucleic acid of any of statements 1 to 9, wherein the at least one duplex region consists of 17-25 nucleotide base pairs.

11. A nucleic acid of any preceding statement, which
a) is blunt ended at both ends; or
b) has an overhang at one end and a blunt end at the other; or
c) has an overhang at both ends.

12. A nucleic acid according to any preceding statement, wherein one or more nucleotides on the first and/or second strand are modified, to form modified nucleotides.

13. A nucleic acid of statement 12, wherein one or more of the odd numbered nucleotides of the first strand are modified.

14. A nucleic acid according to statement 13, wherein one or more of the even numbered nucleotides of the first strand are modified by at least a second modification, wherein the at least second modification is different from the modification of statement 13.

15. A nucleic acid of statement 14, wherein at least one of the one or more modified even numbered nucleotides is adjacent to at least one of the one or more modified odd numbered nucleotides.

16. A nucleic acid of any one of statements 13 to 15, wherein a plurality of odd numbered nucleotides are modified.

17. A nucleic acid of any one of statements 14 to 16, wherein a plurality of even numbered nucleotides are modified by a second modification.

18. A nucleic acid of any of statements 12 to 17, wherein the first strand comprises adjacent nucleotides that are modified by a common modification.

19. A nucleic acid of any of statements 13 to 18, wherein the first strand comprises adjacent nucleotides that are modified by a second modification that is different to the modification of statement 13.

20. A nucleic acid of any of statements 13 to 19, wherein one or more of the odd numbered nucleotides of the second strand are modified by a modification that is different to the modification of statement 13.

21. A nucleic acid according to any of statements 13 to 19, wherein one or more of the even numbered nucleotides of the second strand are modified by the modification of statement 13.

22. A nucleic acid of statement 20 or 21, wherein at least one of the one or more modified even numbered nucleotides of the second strand is adjacent to the one or more modified odd numbered nucleotides.

23. A nucleic acid of any of statements 20 to 22, wherein a plurality of odd numbered nucleotides of the second strand are modified by a common modification.

24. A nucleic acid of any of statements 20 to 23, wherein a plurality of even numbered nucleotides are modified by a modification according to statement 13.

25. A nucleic acid of any of statements 20 to 24, wherein a plurality of odd numbered nucleotides are modified by a second modification, wherein the second modification is different from the modification of statement 13.

26. A nucleic acid of any of statements 20 to 25, wherein the second strand comprises adjacent nucleotides that are modified by a common modification.

27. A nucleic acid of any of statements 20 to 26, wherein the second strand comprises adjacent nucleotides that are modified by a second modification that is different from the modification of statement 13.

28. A nucleic acid according to any one of statements 12 to 27, wherein each of the odd numbered nucleotides in the first strand and each of the even numbered nucleotides in the second strand are modified with a common modification.

29. A nucleic acid of any one of statements 13 to 28, wherein each of the even numbered nucleotides are modified in the first strand with a second modification and each of the odd numbered nucleotides are modified in the second strand with a second modification.

30. A nucleic acid according to any one of statements 20 to 29, wherein the modified nucleotides of the first strand are shifted by at least one nucleotide relative to the unmodified or differently modified nucleotides of the second strand.

31. A nucleic acid of any one of statements 1 to 30, wherein the first strand comprises a sequence of SEQ ID NO: 1.

32. A nucleic acid of any one of statements 1 to 30, wherein the second strand comprises a sequence of SEQ ID NO: 2.

33. A nucleic acid according to any one of statements 8 to 32, wherein the modification and/or modifications are each and individually selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification.

34. A nucleic acid according to any one of statements 8 to 33, wherein the modification is any one of a locked nucleotide, an abasic nucleotide or a non-natural base comprising nucleotide.

35. A nucleic acid according to any one of statements 8 to 34, wherein at least one modification is 2'-O-methyl.

36. A nucleic acid according to any one of statements 8 to 35, wherein at least one modification is 2'-F.

38. A nucleic acid according to any one of statements 1 to 37, conjugated with a ligand.

39. A nucleic acid according to any one of statements 1 to 38, comprising a phosphorothioate linkage between the terminal one, two or three 3' nucleotides and/or 5' nucleotides of the first and/or the second strand, when a phosphorodithioate is not present at that end.

40. A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited and wherein said first and/or second strand includes a phosphorodithioate linkage between the at least two terminal 3' nucleotides and/or the second strand includes a phosphorodithioate linkage between the at least two terminal 5' nucleotides, and wherein the nucleic acid molecule is conjugated to a ligand.

41. A nucleic acid according to any of statements 38 to 40, wherein the ligand comprises one or more GalNac ligands and derivatives thereof.

42. A nucleic acid according to any of statements 38 to 41, wherein the ligand comprises (i) one or more N-acetyl galactosamine (GalNac) moieties and derivatives thereof, and (ii) a linker, wherein the linker conjugates the GalNac moieties to a sequence as defined in any preceding statements.

43. A nucleic acid of statement 40, wherein the nucleotides are modified as defined in any preceding statements.

44. A nucleic acid of any preceding statement, wherein the ligand comprises the formula I:

wherein:
S represents a saccharide, wherein the saccharide is N-acetyl galactosamine;
$X^1$ represents $C_3$—C alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;
A is a branching unit;
$X^3$ represents a bridging unit;
wherein a nucleic acid according to the present invention is conjugated to $X^3$ via a phosphate or modified phosphate (preferably a thiophosphate).

45. A conjugated nucleic acid having one of the following structures

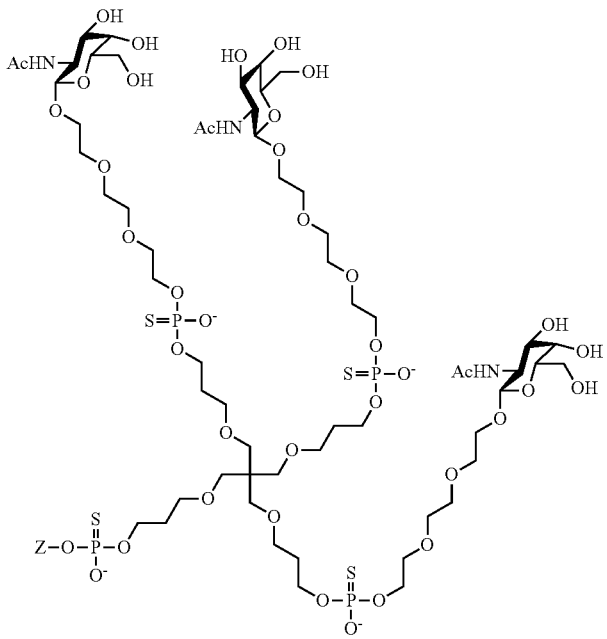

-continued
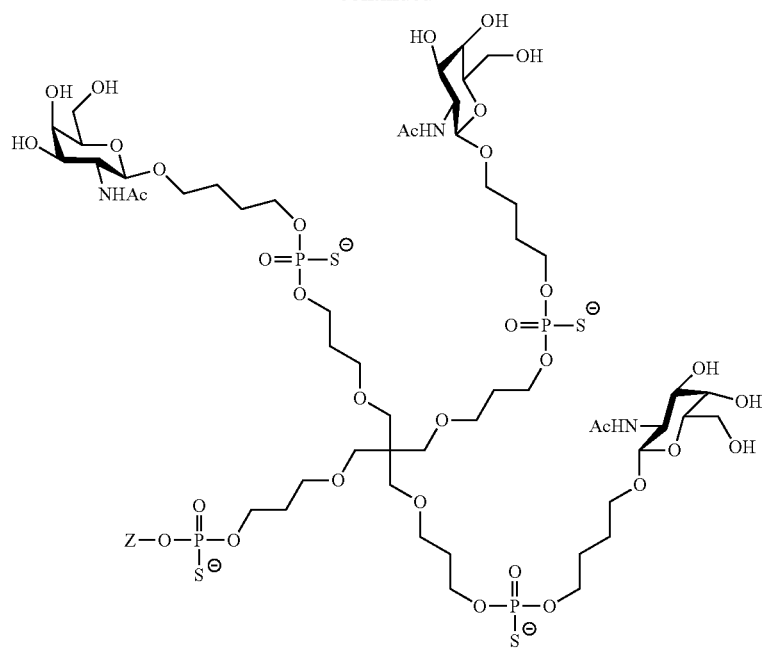
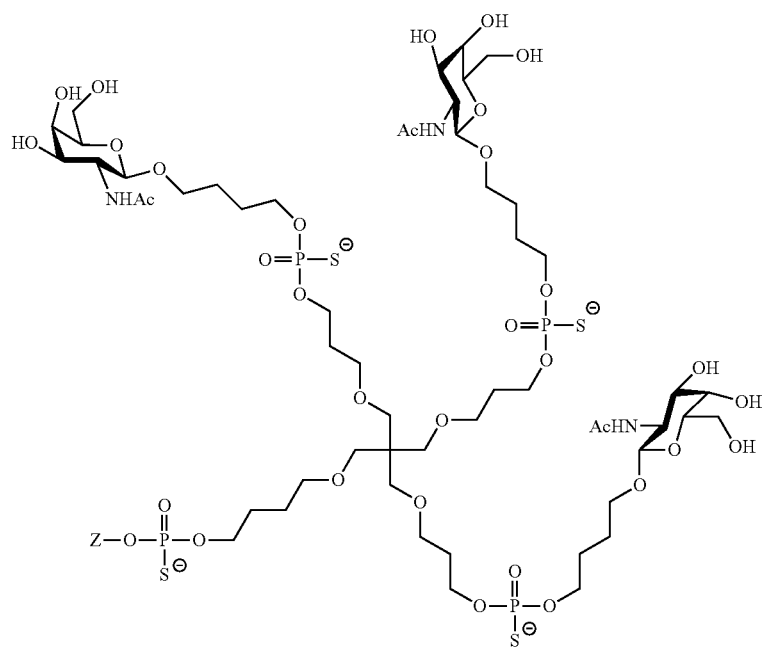

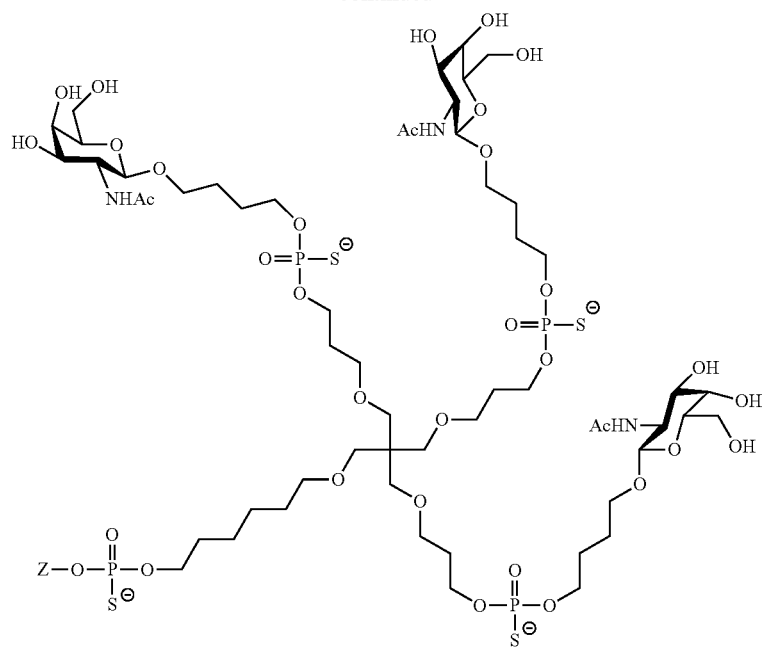
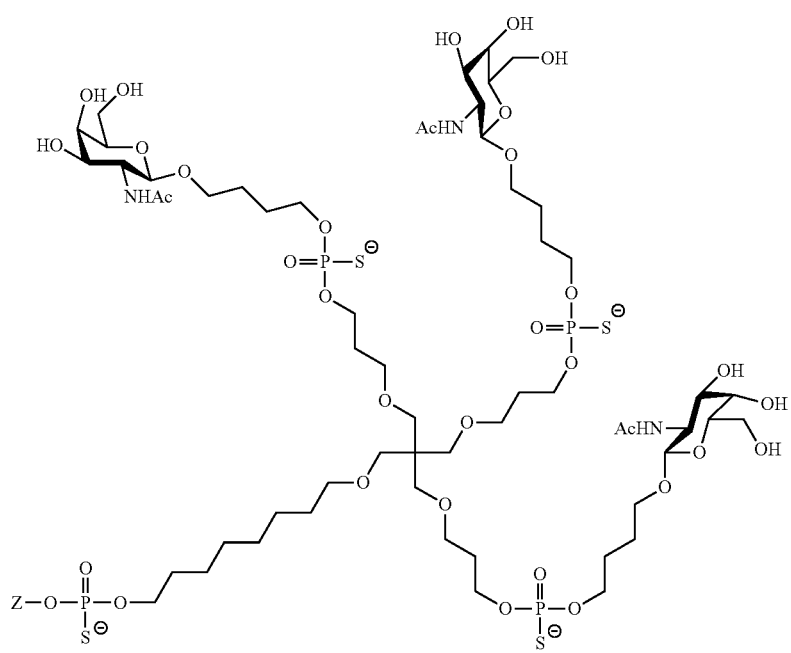

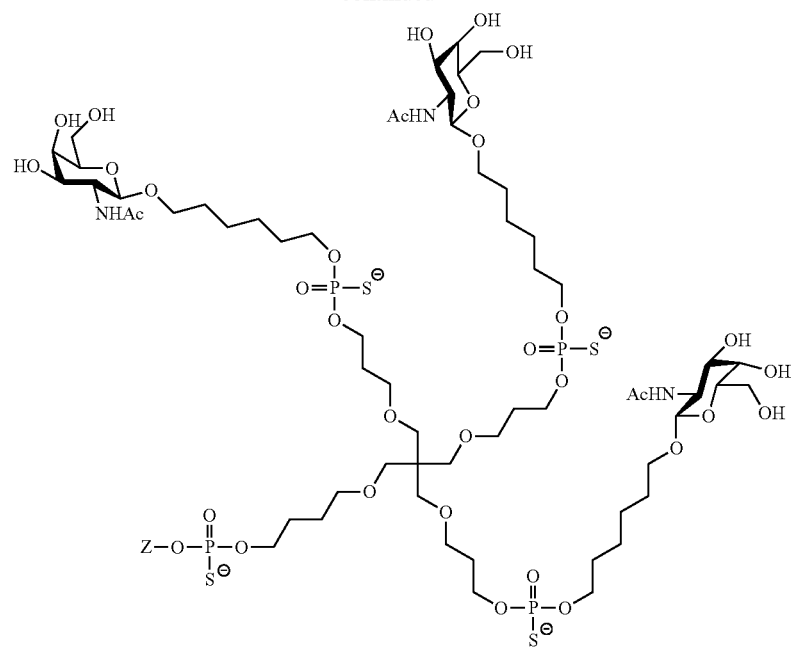
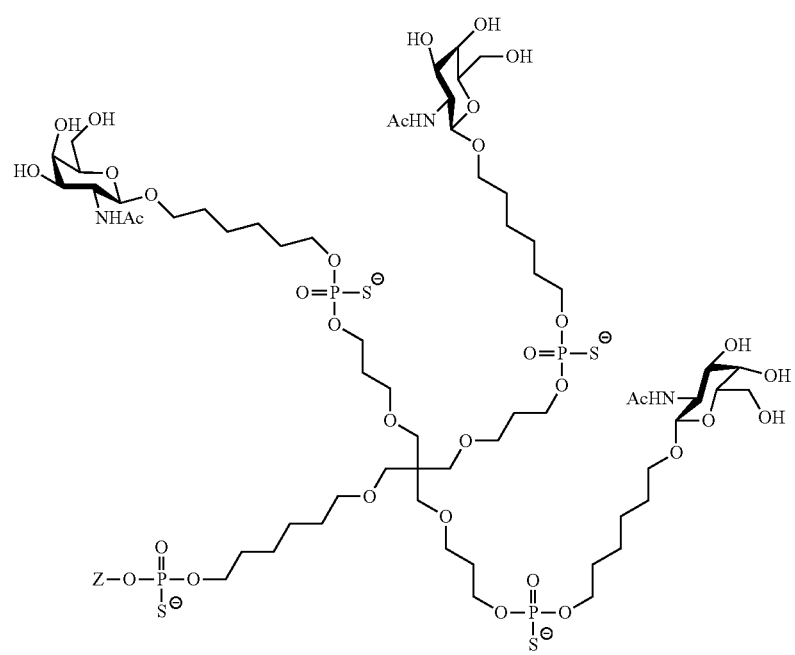

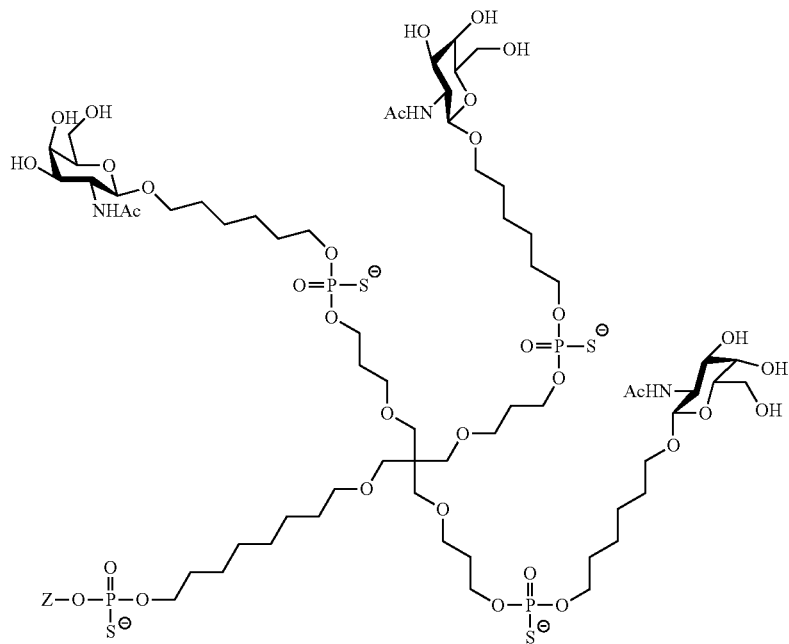
wherein Z is a nucleic acid according to any of statements 1 to 39.
46. A nucleic acid of any preceding statement, wherein the ligand comprises:
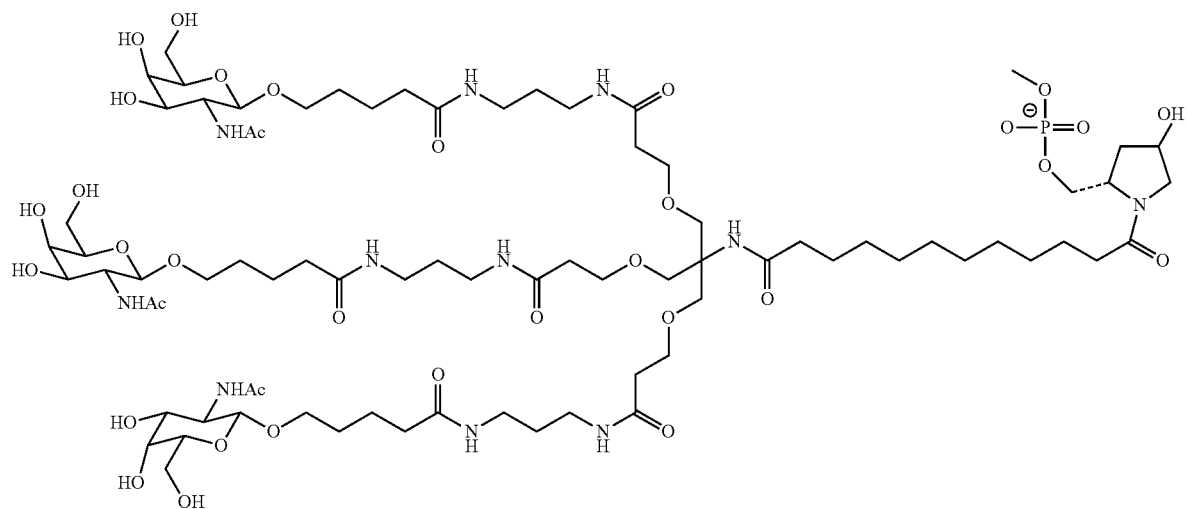

47. A nucleic acid of any of statements 1-27, 31-32 or 39-43, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

48. A nucleic acid of any of statements 1-43 or 47, wherein the first RNA strand is a compound of formula (XV):

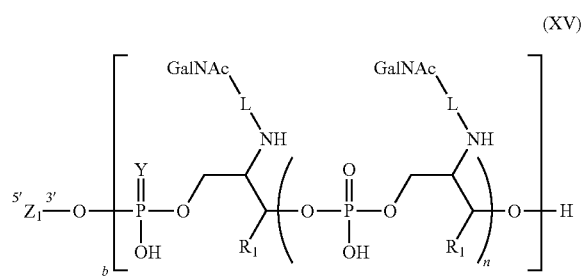

wherein b is 0 or 1; and
the second RNA strand is a compound of formula (XVI):

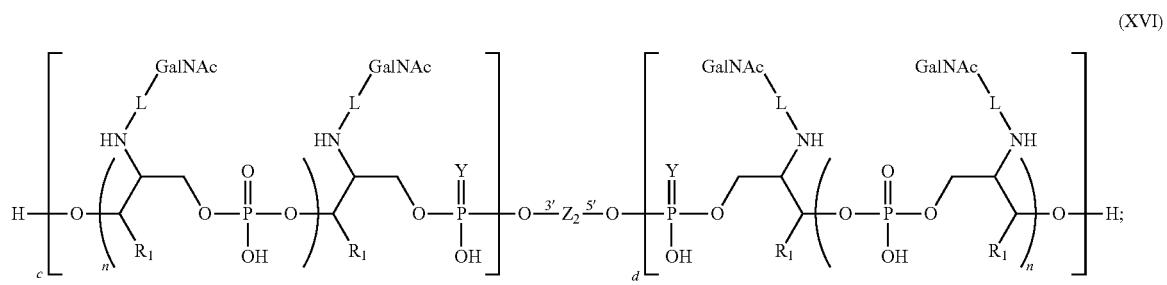

wherein c and d are independently 0 or 1;
wherein:
  $Z_1$ and $Z_2$ are the RNA portions of the first and second RNA strands respectively;
  Y is O or S;
  $R_1$ is H or methyl;
  n is 0, 1, 2 or 3; and
  L is the same or different in formulae (XV) and (XVI) and is selected from the group consisting of:
    —$(CH_2)_q$—, wherein q=2-12;
    —$(CH_2)_r$—C(O)—, wherein r=2-12;
    —$CH_2$—$CH_2$—$O)_s$—$CH_2$—C(O)—, wherein s=1-5;
    —$(CH_2)_t$—CO—NH—$(CH_2)_t$—NH—C(O)—, wherein t is independently is 1-5;
    —$(CH_2)_u$—CO—NH—$(CH_2)_u$—C(O)—, wherein u is independently is 1-5; and
    —$(CH_2)_v$—NH—C(O)—, wherein v is 2-12; and
  wherein the terminal C(O) (if present) is attached to the NH group;
and wherein b+c+d is 2 or 3.

49. A nucleic acid of statement 48, wherein b is 0, c is 1 and d is 1.

50. A nucleic acid of statement 48, wherein b is 1, c is 0 and d is 1.

51. A nucleic acid of statement 48, wherein b is 1, c is 1 and d is 0.

52. A nucleic acid of statement 48, wherein b is 1, c is 1 and d is 1.

53. A nucleic acid of any of statements 48-52, wherein Y is O.

54. A nucleic acid of any of statements 48-52, wherein Y is S.

55. A nucleic acid of any of statements 48-54, wherein $R_1$ is H.

56. A nucleic acid of any of statements 48-54, wherein $R_1$ is methyl.

57. A nucleic acid of any of statements 48-56, wherein n is 0.

58. A nucleic acid of any of statements 48-57, wherein L is —$(CH_2)_r$—C(O)—, wherein r=2-12.

59. A nucleic acid of statement 58 wherein r=2-6.

60. A nucleic acid of statement 59 wherein r=4 or 6 e.g. 4.

61. A composition comprising a nucleic acid as defined in any preceding statement and a formulation comprising:
  i) a cationic lipid, or a pharmaceutically acceptable salt thereof;
  ii) a steroid;
  iii) a phosphatidylethanolamine phospholipid;
  iv) a PEGylated lipid.

62. A composition according to statement 61, wherein in the formulation the content of the cationic lipid component is from about 55 mol % to about 65 mol % of the overall lipid content of the lipid composition, preferably about 59 mol % of the overall lipid content of the lipid composition.

63. A composition of statement 62, wherein the formulation comprises;
A cationic lipid having the structure;
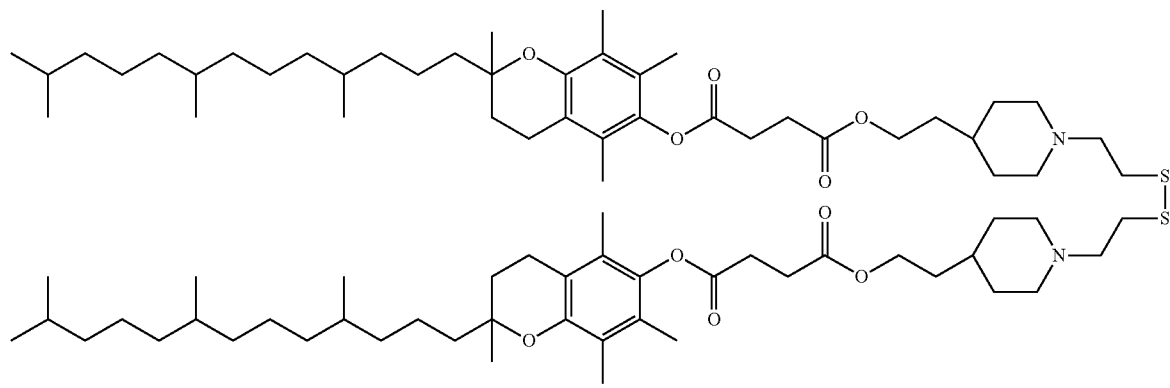 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]
the steroid has the structure;
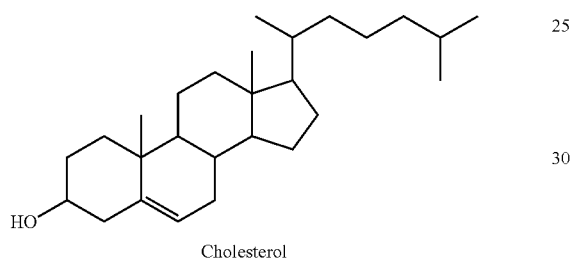
Cholesterol
the phosphatidylethanolamine phospholipid has the structure;
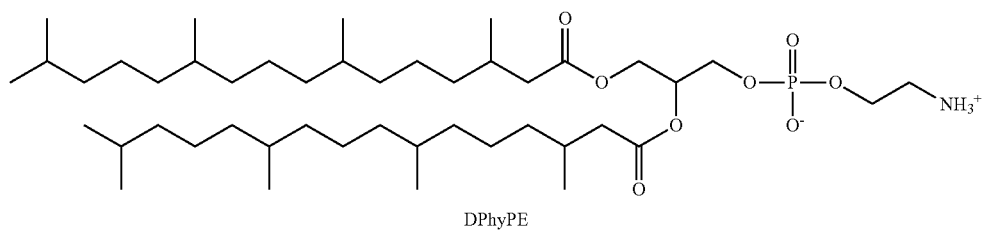 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]
DPhyPE
and the PEGylated lipid has the structure;
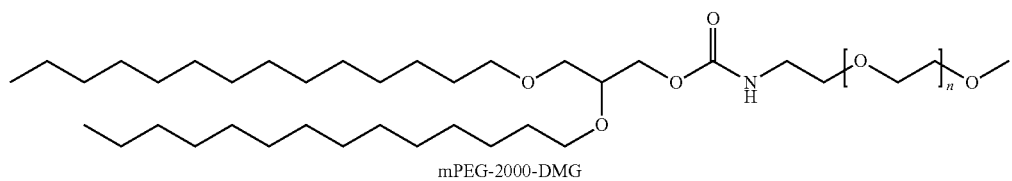
mPEG-2000-DMG 64. A composition comprising a nucleic acid or conjugated nucleic acid of any preceding statement and a physiologically acceptable excipient.

65. A nucleic acid or conjugated nucleic acid according to any preceding statement for use in the treatment of a disease or disorder.

66. Use of a nucleic acid or conjugated nucleic acid according to any preceding statement in the manufacture of a medicament for treating a disease or disorder.

67. A method of treating a disease or disorder comprising administration of a composition comprising a nucleic acid or conjugated nucleic acid according to any one preceding statement to an individual in need of treatment.

68. The method of statement 67, wherein the nucleic acid or conjugated nucleic acid molecule is administered to the subject subcutaneously or intravenously.

69. A process of making a nucleic acid or conjugated nucleic acid of any of statements 1 to 65.

TABLE 7

Summary sequence table

| SEQ ID NO: | Name | Sequence (5'-3') | Unmodified Sequence counterpart (5'-3') |
|---|---|---|---|
| 1 | STS12009L4A | AACCAGAAGAAGCAGGUGA | AACCAGAAGAAGCAGGUGA |
| 2 | STS12009L4B | UCACCUGCUUCUUCUGGUU | UCACCUGCUUCUUCUGGUU |
| 3 | STS12009L4A | mA(ps)fA(ps)mCfCmAfGmAfAmGfAmAfGmCfAmGfGmU(ps)fG(ps)mA | AACCAGAAGAAGCAGGUGA |
| 4 | STS12009L4B | [ST23(ps)]3 ST41(ps)-fUmCfAmCfCmUfGmCfUmUfCmUfUmCfUmGfG(ps)mU(ps)fU | UCACCUGCUUCUUCUGGUU |
| 5 | STS12009V21L4A | mA(ps)fAmCfCmAfGmAfAmGfAmAfGmCfAmGfGmUfG(ps)mA | AACCAGAAGAAGCAGGUGA |
| 6 | STS12009V21L4B | [ST23(ps)]3 ST41(ps)-fUmCfAmCfCmUfGmCfUmUfCmUfUmCfUmGfGmU(ps)fU | UCACCUGCUUCUUCUGGUU |
| 7 | STS12009V16L4A | mA(ps2)fA(ps2)mCfCmAfGmAfAmGfAmAfGmCfAmGfGmU(ps2)fG(ps2)mA | AACCAGAAGAAGCAGGUGA |
| 8 | STS12009V16L4B | [ST23(ps)]3 ST41(ps)-fUmCfAmCfCmUfGmCfUmUfCmUfUmCfUmGfG(ps2)mU(ps2)fU | UCACCUGCUUCUUCUGGUU |
| 9 | STS12009V15L4A | mA(ps2)fAmCfCmAfGmAfAmGfAmAfGmCfAmGfGmUfG(ps2)mA | AACCAGAAGAAGCAGGUGA |
| 10 | STS12009V15L4B | [ST23(ps)]3 ST41(ps)-fUmCfAmCfCmUfGmCfUmUfCmUfUmCfUmGfGmU(ps2)fU | UCACCUGCUUCUUCUGGUU |
| 11 | STS12009V20L50A | mA(ps)fA(ps)mCfCmAfGmAfAmGfAmAfGmCfAmGfGmU(ps)fG(ps)mA | AACCAGAAGAAGCAGGUGA |
| 12 | STS12009V20L50B | [ST23]3 ST41-fU(ps)mC(ps)fAmCfCmAfGmCfUmUfCmUfUmCfUmGfG(ps)mU(ps)fU | UCACCUGCUUCUUCUGGUU |
| 13 | STS12009V19L50A | mA(ps)fAmCfCmAfGmAfAmGfAmAfGmCfAmGfGmUfG(ps)mA | AACCAGAAGAAGCAGGUGA |
| 14 | STS12009V19L50B | [ST23]3 ST41-fU(ps)mCfAmCfCmUfGmCfUmUfCmUfUmCfUmGfGmU(ps)fU | UCACCUGCUUCUUCUGGUU |
| 15 | STS12009V18L50A | mA(ps2)fA(ps2)mCfCmAfGmAfAmGfAmAfGmCfAmGfGmU(ps2)fG(ps2)mA | AACCAGAAGAAGCAGGUGA |
| 16 | STS12009V18L50B | [ST23]3 ST41-fU(ps2)mC(ps2)fAmCfCmUfGmCfUmUfCmUfUmCfUmGfG(ps2)mU(ps2)fU | UCACCUGCUUCUUCUGGUU |
| 17 | STS12009V17L50A | mA(ps2)fAmCfCmAfGmAfAmGfAmAfGmCfAmGfGmUfG(ps2)mA | AACCAGAAGAAGCAGGUGA |
| 18 | STS12009V17L50B | [ST23]3 ST41-fU(ps2)mCfAmCfCmUfGmCfUmUfCmUfUmCfUmGfGmU(ps2)fU | UCACCUGCUUCUUCUGGUU |
| 19 | STS12009V34L4A | mA(ps)fA(ps)mCfCmAfGmAfAmGfAmAfGmCfAmGfGmU(ps)fG(ps)mA | AACCAGAAGAAGCAGGUGA |
| 20 | STS12009V34L4B | [ST23(ps)]3 ST41(ps)-fUmCfAmCfCmUfGmCfUmUfCmUfUmCfUmGfGmU(ps2)fU | UCACCUGCUUCUUCUGGUU |
| 21 | STS12009V36L4A | mA(ps)fA(ps)mCfCmAfGmAfAmGfAmAfGmCfAmGfGmUfG(ps2)mA | AACCAGAAGAAGCAGGUGA |
| 22 | STS12009V36L4B | [ST23(ps)]3 ST41(ps)-fUmCfAmCfCmUfGmCfUmUfCmUfUmCfUmGfG(ps)mU(ps)fU | UCACCUGCUUCUUCUGGUU |
| 23 | STS12009V37L4A | mA(ps2)fAmCfCmAfGmAfAmGfAmAfGmCfAmGfGmU(ps)fG(ps)mA | AACCAGAAGAAGCAGGUGA |
| 24 | STS12009V37L4B | [ST23(ps)]3 ST41(ps)-fUmCfAmCfCmUfGmCfUmUfCmUfUmCfUmGfG(ps)mU(ps)fU | UCACCUGCUUCUUCUGGUU |

TABLE 7-continued

Summary sequence table

| SEQ ID NO: | Name | Sequence (5'-3') | Unmodified Sequence counterpart (5'-3') |
|---|---|---|---|
| 25 | STS12009V40L50A | mA(ps)fA(ps)mCfCmAfGmAfAmGfAmAfGmCfAmGfGmU(ps)fG(ps)mA | AACCAGAAGAAGCAGGUGA |
| 26 | STS12009V40L50B | [ST23]3 ST41-fU(ps2)mCfAmCfCmUfGmCfUmUfCmUfUmCfUmGfGmU(ps2)fU | UCACCUGCUUCUUCUGGUU |
| 27 | STS12009V54L50A | mA(ps)fA (ps)mCfCmAfGmAfAmGfAmAfGmCfAmGfGmUfG(ps2)mA | AACCAGAAGAAGCAGGUGA |
| 28 | STS12009V54L50B | [ST23]3 ST41-fU(ps2)mCfAmCfCmUfGmCfUmUfCmUfUmCfUmGfGmU(ps2)fU | UCACCUGCUUCUUCUGGUU |
| 29 | STS12009V55L50A | mA(ps)fA (ps)mCfCmAfGmAfAmGfAmAfGmCfAmGfGmUfG(ps2)mA | AACCAGAAGAAGCAGGUGA |
| 30 | STS12009V55L50B | [ST23]3 ST41-fUmCfAmCfCmUfGmCfUmUfCmUfUmCfUmGfGmU(ps2)fU | UCACCUGCUUCUUCUGGUU |
| 31 | STS12009V56L50A | mAfAmCfCmAfGmAfAmGfAmAfGmCfAmGfGmUfGmA | AACCAGAAGAAGCAGGUGA |
| 32 | STS12009V56L50B | [ST23]3 ST41-fUmCfAmCfCmUfGmCfUmUfCmUfUmCfUmGfGmU(ps2)fU | UCACCUGCUUCUUCUGGUU |
| 33 | STS12009V57L50A | mAfAmCfCmAfGmAfAmGfAmAfGmCfAmGfGmUfG (ps2)mA | AACCAGAAGAAGCAGGUGA |
| 34 | STS12009V57L50B | [ST23]3 ST41-fUmCfAmCfCmUfGmCfUmUfCmUfUmCfUmGfGmU(ps2)fU | UCACCUGCUUCUUCUGGUU |
| 35 | X0214A | mA(ps)fA(ps)mC fC mA fG mA fA mG fA mA fG mC fA mG fG mU fG (ps2)mA | AACCAGAAGAAGCAGGUGA |
| 36 | X0214B | [ST23]3 ST41 fU (ps2)mC fA mC fC mU fG mC fU mU fC mU fU mC fU mG fG mU(ps2)fU | UCACCUGCUUCUUCUGGUU |
| 37 | X0345A | mAfA mC fC mA fG mA fA mG fA mA fG mC fA mG fG mU fG(ps2)mA | AACCAGAAGAAGCAGGUGA |
| 38 | X0345B | [ST23]3 ST41 fU(ps2)mC fA mC fC mU fG mC fU mU fC mU fU mC fU mG fG mU(ps2)fU | UCACCUGCUUCUUCUGGUU |
| 39 | X0346A | mA(ps)fA(ps)mC fC mAfG mA fA mG fA mA fG mC fA mG fG mU fG (ps2)mA | AACCAGAAGAAGCAGGUGA |
| 40 | X0346B | [ST23(ps)]3 ST41(ps)fU mC fA mC fC mU fG mC fU mU fC mU fU mC fU mG fG mU(ps2)fU | UCACCUGCUUCUUCUGGUU |
| 41 | X0347A | mA fA mC fC mA fG mA fA mG fA mA fG mC fA mG fG mU fG(ps2)mA | AACCAGAAGAAGCAGGUGA |
| 42 | X0347B | [ST23(ps)]3 ST41(ps)fU mC fA mC fC mU fG mC fU mU fC mU fU mC fU mG fG mU(ps2)fU | UCACCUGCUUCUUCUGGUU |
| 43 | X0027A | mA (ps)fA (ps)mC fC mA fG mA fA mG fA mA fG mC fA mG fG mU(ps) fG(ps)mA | AACCAGAAGAAGCAGGUGA |
| 44 | X0027B | [ST23(ps)]3 ST41(ps)fU mC fA mC fC mU fG mC fU mU fC mU fU mC fU mG fG(ps)mU(ps)fU | UCACCUGCUUCUUCUGGUU |
| 45 | X0454A | (vp)-mU fA mC fC mA fG mA fA mG fA mA fG mC fA mG fG mU(ps) fG (ps)mA | UACCAGAAGAAGCAGGUGA |
| 46 | X0454B | Ser(GN)(ps)mU(ps)mC(ps)mA mC mC mU fG fC fU mU mC mU mU mC mU mG mG(ps)mU(ps)mA(ps)Ser(GN) | UCACCUGCUUCUUCUGGUA |
| 47 | X0456A | (vp)-mU fA mC fC mA fG mA fA mG fA mA fG mC fA mG fG mU fG (ps2)mA | UACCAGAAGAAGCAGGUGA |
| 48 | X0456B | Ser(GN)mU (ps2)mC mA mC mC mU fG fC fU mU mC mU mU mC mU mG mG mU(ps2)mA Ser(GN) | UCACCUGCUUCUUCUGGUA |

Key
Sequences ending with a "A" (as in X0456A) are first strand sequences and sequences ending with a "B" (as in X0456B )are second strand sequences.
mA, mU, mC, mG - 2'-OMe RNA
fA, fU, fC, fG - 2'-F RNA
(ps) - phosphorothioate
(ps2) - phosphorodithioate
(vp)- Vinyl-(E)-phosphonate
The sequences listed above may be disclosed with a linker or ligand, such as GalNAc or (ps)or (ps2) linkages for example. These form an optional, but preferred, part of the sequence of the sequence listing.

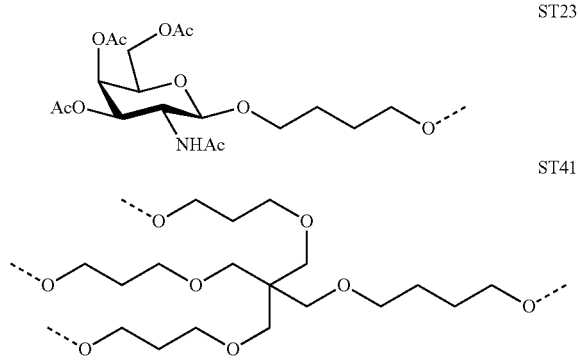

ST23

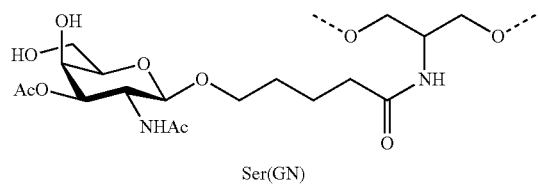

ST41

Ser(GN)

The invention claimed is:

1. A nucleic acid for inhibiting expression of a target gene in a cell, comprising at least one duplex region 17-25 nucleotides in length that comprises at least a portion of a first strand and at least a portion of a second strand that is at least partially complementary to the first strand, wherein said second strand is 17-35 nucleotides in length, wherein said first strand is 17-35 nucleotides in length and comprises a nucleotide sequence that is at least partially complementary to at least a portion of RNA transcribed from said target gene, wherein the nucleic acid comprises (a) a phosphorodithioate linkage only between the two terminal nucleotides at the 3' end of the second strand, (b) phosphorodithioate linkages only between the two terminal nucleotides at the 3' end of the first strand and the 3' end of the second strand or (c) phosphorodithioate linkages only between the two terminal nucleotides at the 3' end of the first strand, the 3' end of the second strand, and the 5' end of the second strand; and wherein the first strand comprises internucleoside linkages other than phosphorodithioate between the two, three or four terminal nucleotides at the 5' end.

2. The nucleic acid of claim 1, wherein the nucleic acid is conjugated to a ligand comprising a compound of formula (I):

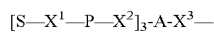

(I)

wherein:

S represents a saccharide;

$X^1$ represents $C_3$-$C_6$ alkylene or (—$CH_2$—$CH_2$—O)$_m$(—$CH_2$)$_2$— wherein m is 1, 2, or 3;

P is a phosphate or modified phosphate;

$X^2$ is alkylene or an alkylene ether of the formula (—$CH_2$)n-O—$CH_2$— where n=1-6;

A is a branching unit;

$X^3$ represents a bridging unit;

wherein a nucleic acid as defined in claim 1 is conjugated to $X^3$ via a phosphate or modified phosphate.

3. The nucleic acid of claim 1, wherein the nucleic acid is conjugated to a ligand, wherein the first RNA strand is a compound of formula (XV):

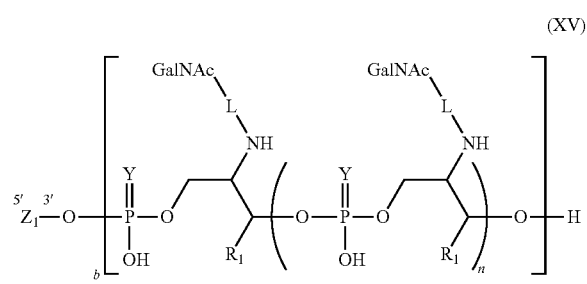

(XV)

wherein b is 0 or 1; and the second RNA strand is a compound of formula (XVI):

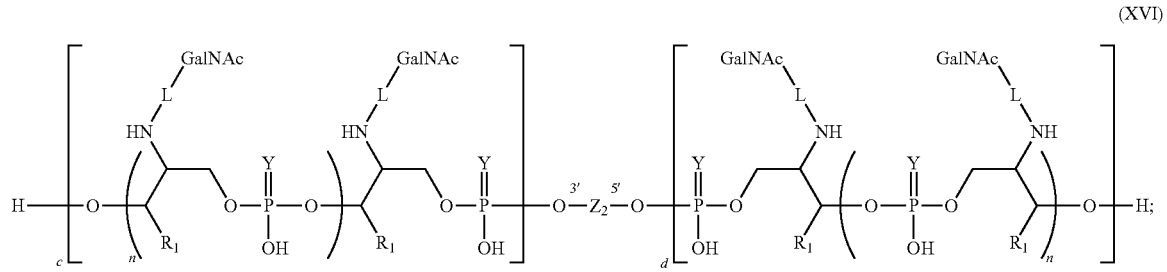

(XVI)

wherein c and d are independently 0 or 1;
wherein:
$Z_1$ and $Z_2$ are the RNA portions of the first and second RNA strands respectively;
Y is O or S;
$R_1$ is H or methyl;
n is 0, 1, 2 or 3; and
L is the same or different in formulae (XV) and (XVI) and is selected from the group consisting of:
—$(CH_2)_q$—, wherein q=2-12;
—$(CH_2)_r$—C(O)—, wherein r=2-12;
—$CH_2$—$CH_2$—O)s-$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently 1-5; and
—$(CH_2)_v$—NH—C(O)—, wherein v is 2-12; and
wherein the terminal C(O), if present, is attached to the NH group;
and wherein b+c+d is 2 or 3.

4. The nucleic acid of claim 1, wherein the first RNA strand has a terminal 5' (E)-vinylphosphonate nucleotide at its 5' end.

5. The nucleic acid of claim 1, wherein the nucleotides of the first strand are modified by a first modification on the odd numbered nucleotides, and modified with a second modification on the even numbered nucleotides, and wherein the nucleotides of the second strand are modified on the odd numbered nucleotides with the second modification and modified with the first modification on the even numbered nucleotides, wherein the first strand is numbered 5' to 3', the 5'-most nucleotide being nucleotide number 1 of the first strand and the second strand is numbered 3' to 5', the 3'-most nucleotide being nucleotide number 1 of the second strand.

6. The nucleic acid of claim 1, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

7. The nucleic acid of claim 1, wherein all the linkages between the nucleotides of both strands other than the linkage between the two terminal nucleotides at the 3' end of the first strand and the linkages between the two terminal nucleotides at the 3' end and the 5' end of the second strand, are unsubstituted phosphate linkages.

8. A pharmaceutical composition comprising a nucleic acid of claim 1 and further comprising a delivery vehicle and/or liposomes and/or a physiologically acceptable excipient and/or a carrier and/or a diluent.

9. The nucleic acid of claim 2, wherein the saccharide is N-acetyl galactosamine.

10. The nucleic acid of claim 4, wherein the terminal 5' (E)-vinylphosphonate nucleotide is linked to the second nucleotide in the first strand by a phosphodiester linkage.

11. The nucleic acid of claim 5, wherein the first modification is 2'OMe.

12. The nucleic acid of claim 5, wherein the second modification is 2' fluoro.

13. The nucleic acid of claim 5, wherein the nucleic acid is blunt ended at both ends.

14. The nucleic acid of claim 6, wherein the remaining nucleotides are modified with a 2'OMe modification.

* * * * *

SEQUENCE LISTING

<160> NUMBER OF SEQ ID NOS: 48

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
aaccagaaga agcagguga                                              19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
ucaccugcuu cuucugguu                                              19

<210> SEQ ID NO 3
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 3
aaccagaaga agcagguga                                              19

<210> SEQ ID NO 4
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 4
ucaccugcuu cuucugguu                                              19

<210> SEQ ID NO 5
<211> LENGTH: 19
<212> TYPE: RNA
<213> ORGANISM: Artificial Sequence
<220> FEATURE:

```
<223> OTHER INFORMATION: siRNA - modified_base, modified as per summary
      sequence table at the end of the description

<400> SEQUENCE: 5
aaccagaaga agcagguga                                                       19

<210> SEQ ID NO 6
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 6
ucaccugcuu cuucugguu                                                       19

<210> SEQ ID NO 7
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 7
aaccagaaga agcagguga                                                       19

<210> SEQ ID NO 8
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 8
ucaccugcuu cuucugguu                                                       19

<210> SEQ ID NO 9
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 9
aaccagaaga agcagguga                                                       19

<210> SEQ ID NO 10
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 10
ucaccugcuu cuucugguu                                                       19

<210> SEQ ID NO 11
<211> LENGTH: 19
<212> TYPE: RNA
<213> ORGANISM: Artificial Sequence
<220> FEATURE:
<223> OTHER INFORMATION: siRNA - modified_base, modified as per summary
```

-continued sequence table at the end of the description

<400> SEQUENCE: 11
aaccagaaga agcagguga                                                19

<210> SEQ ID NO 12
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 12
ucaccugcuu cuucugguu                                                19

<210> SEQ ID NO 13
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 13
aaccagaaga agcagguga                                                19

<210> SEQ ID NO 14
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 14
ucaccugcuu cuucugguu                                                19

<210> SEQ ID NO 15
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 15
aaccagaaga agcagguga                                                19

<210> SEQ ID NO 16
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 16
ucaccugcuu cuucugguu                                                19

<210> SEQ ID NO 17
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 17
aaccagaaga agcagguga                                                    19

<210> SEQ ID NO 18
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 18
ucaccugcuu cuucugguu                                                    19

<210> SEQ ID NO 19
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 19
aaccagaaga agcagguga                                                    19

<210> SEQ ID NO 20
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 20
ucaccugcuu cuucugguu                                                    19

<210> SEQ ID NO 21
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 21
aaccagaaga agcagguga                                                    19

<210> SEQ ID NO 22
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 22
ucaccugcuu cuucugguu                                                    19

<210> SEQ ID NO 23
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 23
aaccagaaga agcagguga                                                19

<210> SEQ ID NO 24
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 24
ucaccugcuu cuucugguu                                                19

<210> SEQ ID NO 25
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 25
aaccagaaga agcagguga                                                19

<210> SEQ ID NO 26
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 26
ucaccugcuu cuucugguu                                                19

<210> SEQ ID NO 27
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 27
aaccagaaga agcagguga                                                19

<210> SEQ ID NO 28
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 28
ucaccugcuu cuucugguu                                                19

<210> SEQ ID NO 29
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 29

-continued aaccagaaga agcagguga                                            19

<210> SEQ ID NO 30
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 30
ucaccugcuu cuucugguu                                            19

<210> SEQ ID NO 31
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 31
aaccagaaga agcagguga                                            19

<210> SEQ ID NO 32
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 32
ucaccugcuu cuucugguu                                            19

<210> SEQ ID NO 33
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 33
aaccagaaga agcagguga                                            19

<210> SEQ ID NO 34
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 34
ucaccugcuu cuucugguu                                            19

<210> SEQ ID NO 35
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 35
aaccagaaga agcagguga                                       19

<210> SEQ ID NO 36
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 36
ucaccugcuu cuucugguu                                       19

<210> SEQ ID NO 37
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 37
aaccagaaga agcagguga                                       19

<210> SEQ ID NO 38
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 38
ucaccugcuu cuucugguu                                       19

<210> SEQ ID NO 39
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 39
aaccagaaga agcagguga                                       19

<210> SEQ ID NO 40
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 40
ucaccugcuu cuucugguu                                       19

<210> SEQ ID NO 41
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 41
aaccagaaga agcagguga                                       19

```
<210> SEQ ID NO 42
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 42
ucaccugcuu cuucugguu                                                      19

<210> SEQ ID NO 43
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 43
aaccagaaga agcagguga                                                      19

<210> SEQ ID NO 44
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 44
ucaccugcuu cuucugguu                                                      19

<210> SEQ ID NO 45
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 45
uaccagaaga agcagguga                                                      19

<210> SEQ ID NO 46
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 46
ucaccugcuu cuucuggua                                                      19

<210> SEQ ID NO 47
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 47
uaccagaaga agcagguga                                                      19
```

```
<210> SEQ ID NO 48
<211> LENGTH: 19
<212> TYPE: RNA
<213> ORGANISM: Artificial Sequence
<220> FEATURE:
<223> OTHER INFORMATION: siRNA - modified_base, modified as per summary
      sequence table at the end of the description

<400> SEQUENCE: 48
ucaccugcuu cuucuggua                                                    19
```